US012232855B2

(12) United States Patent
Wakita et al.

(10) Patent No.: US 12,232,855 B2
(45) Date of Patent: Feb. 25, 2025

(54) MEASUREMENT DEVICE AND MEASUREMENT METHOD

(71) Applicant: SONY GROUP CORPORATION, Tokyo (JP)

(72) Inventors: Yoshihiro Wakita, Tokyo (JP); Kota Aizawa, Tokyo (JP); Takahiro Igarashi, Kanagawa (JP)

(73) Assignee: SONY GROUP CORPORATION, Tokyo (JP)

( * ) Notice: Subject to any disclaimer, the term of this patent is extended or adjusted under 35 U.S.C. 154(b) by 173 days.

(21) Appl. No.: 17/906,354

(22) PCT Filed: Mar. 11, 2021

(86) PCT No.: PCT/JP2021/009819
§ 371 (c)(1),
(2) Date: Sep. 15, 2022

(87) PCT Pub. No.: WO2021/193110
PCT Pub. Date: Sep. 30, 2021

(65) Prior Publication Data
US 2023/0035537 A1 Feb. 2, 2023

(30) Foreign Application Priority Data

Mar. 25, 2020 (JP) ................................. 2020-053785

(51) Int. Cl.
*A61B 5/026* (2006.01)
*A61B 5/00* (2006.01)

(52) U.S. Cl.
CPC .......... *A61B 5/0261* (2013.01); *A61B 5/7225* (2013.01); *A61B 2560/0209* (2013.01)

(58) Field of Classification Search
CPC ................ A61B 5/0261; A61B 5/7225; A61B 2560/0209; A61B 2562/0233; A61B 5/0285
See application file for complete search history.

(56) References Cited

U.S. PATENT DOCUMENTS

| | | | |
|---|---|---|---|
| 5,285,233 A * | 2/1994 | Yoshida | G02B 7/32 250/201.4 |
| 5,345,167 A | 9/1994 | Hasegawa | |
| 2011/0190641 A1 | 8/2011 | Tateishi | |

(Continued)

FOREIGN PATENT DOCUMENTS

| | | |
|---|---|---|
| EP | 3430984 A1 | 1/2019 |
| JP | 2001-112728 A | 4/2001 |

(Continued)

OTHER PUBLICATIONS

International Search Report and Written Opinion of PCT Application No. PCT/JP2021/009819, issued on May 25, 2021, 10 pages of ISRWO.

*Primary Examiner* — Thanh Luu
*Assistant Examiner* — Monica T Taba
(74) *Attorney, Agent, or Firm* — CHIP LAW GROUP

(57) ABSTRACT

A measurement device 100 includes a light source that irradiates a subject with light, a drive control unit that intermittently drives the light source, a light receiving element that receives scattered light of the light from the subject and generates an electric signal, and an amplifier that amplifies the electric signal with an integration circuit.

16 Claims, 49 Drawing Sheets

(56) References Cited

U.S. PATENT DOCUMENTS

| | | |
|---|---|---|
| 2014/0275852 A1 | 9/2014 | Hong |
| 2017/0055860 A1* | 3/2017 | Vermeulen ......... A61B 5/02433 |
| 2017/0142352 A1* | 5/2017 | Pang ..................... H04N 25/75 |
| 2019/0090767 A1* | 3/2019 | Sako ......................... G01J 3/42 |
| 2022/0296148 A1* | 9/2022 | Kanagaratnam ... A61N 1/36017 |

FOREIGN PATENT DOCUMENTS

| | | |
|---|---|---|
| JP | 2017-516533 A | 6/2017 |
| WO | 2010/023744 A1 | 3/2010 |
| WO | WO-2013015828 A1 | 1/2013 |
| WO | 2017/159396 A1 | 9/2017 |

\* cited by examiner

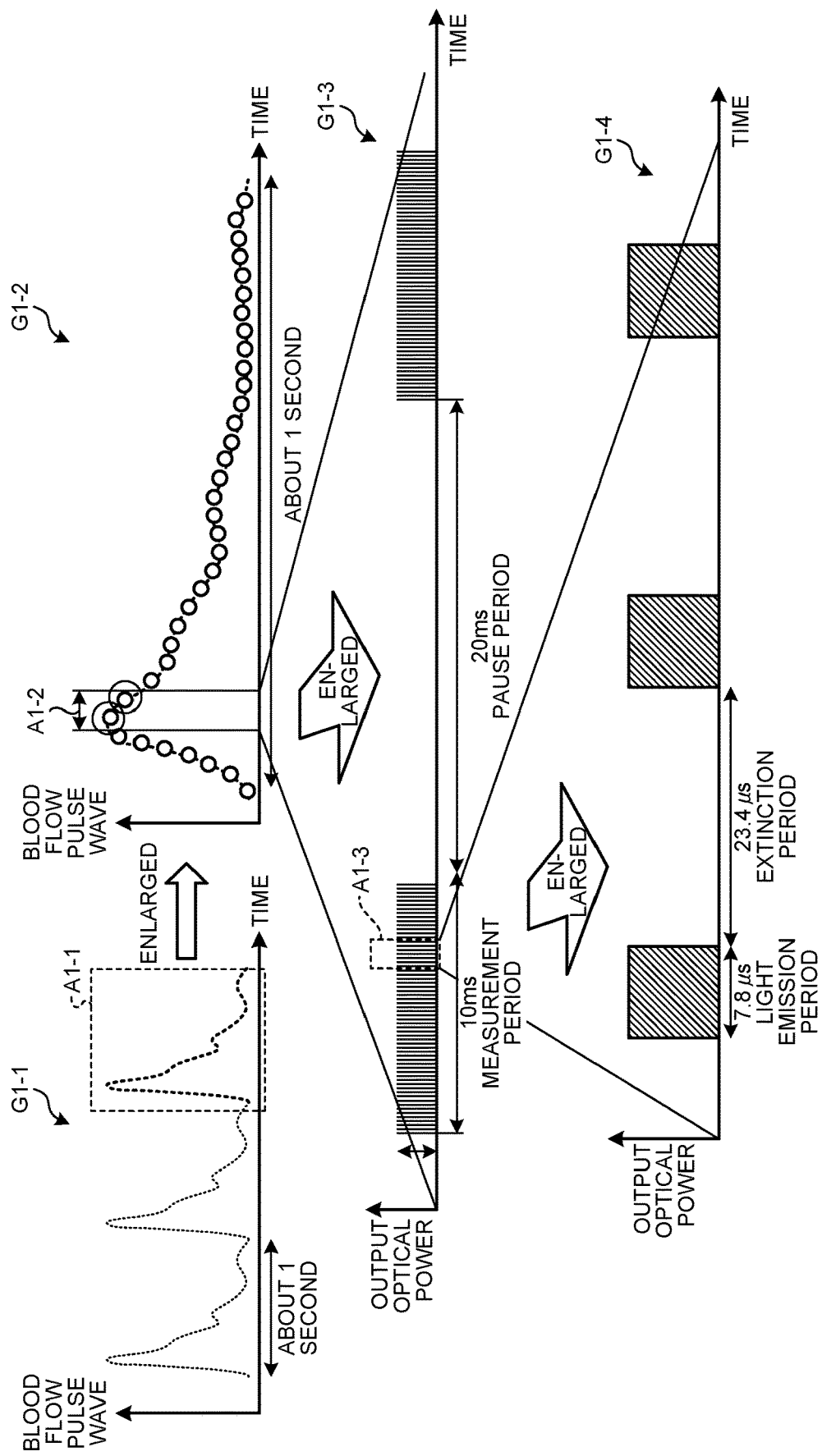

FIG.62

| SWITCH TYPE | TIME CONSTANT REDUCTION | C CHARGE RETENTION | CHARGING-REQUIRING POTENTIAL DIFFERENCE | GLITCH NOISE | LEVEL OF GLITCH NOISE | LENGTH OF GLITCH NOISE | OTHER ADVANTAGE | OTHER DRAWBACK |
|---|---|---|---|---|---|---|---|---|
| NO SWITCH (CONVENTIONAL TECHNOLOGY) | ABSENT | ABSENT | CURRENT POTENTIAL DIFFERENCE BETWEEN BOTH ENDS | PRESENT | LARGE | LONG | - | - |
| SWc1 | PRESENT | ABSENT | CURRENT POTENTIAL DIFFERENCE BETWEEN BOTH ENDS | PRESENT | LARGE | SHORT | SIMPLE CIRCUIT | - |
| SWc2 | ABSENT | PRESENT | PREVIOUS POTENTIAL DIFFERENCE BETWEEN BOTH ENDS-CURRENT POTENTIAL DIFFERENCE BETWEEN BOTH ENDS | PRESENT | SMALL | SLIGHTLY SHORT | INTEGRATED WITH PRECEDING STAGE | - |
| SWc3 | ABSENT | PRESENT | PREVIOUS POTENTIAL DIFFERENCE BETWEEN BOTH ENDS-CURRENT POTENTIAL DIFFERENCE BETWEEN BOTH ENDS | PRESENT | SMALL | SLIGHTLY SHORT | INTEGRATED WITH SUBSEQUENT STAGE | - |
| SWc2+SWc3 | ABSENT | PRESENT (ADVANCED) | PREVIOUS POTENTIAL DIFFERENCE BETWEEN BOTH ENDS-CURRENT POTENTIAL DIFFERENCE BETWEEN BOTH ENDS | PRESENT | SMALL | SLIGHTLY SHORT | SMALL DISCHARGE AMOUNT | SW ON BOTH SIDES |
| SWc1+SWc2 | PRESENT | PRESENT | PREVIOUS POTENTIAL DIFFERENCE BETWEEN BOTH ENDS-CURRENT POTENTIAL DIFFERENCE BETWEEN BOTH ENDS | PRESENT | SMALL | SHORT | - | SW ON BOTH SIDES |
| SWc1+SWc3 | PRESENT | PRESENT | PREVIOUS POTENTIAL DIFFERENCE BETWEEN BOTH ENDS-CURRENT POTENTIAL DIFFERENCE BETWEEN BOTH ENDS | ABSENT | ABSENT | ABSENT | INTEGRATED WITH SUBSEQUENT STAGE | - |
| SWc1+SWc2+SWc3 | PRESENT | PRESENT (ADVANCED) | PREVIOUS POTENTIAL DIFFERENCE BETWEEN BOTH ENDS-CURRENT POTENTIAL DIFFERENCE BETWEEN BOTH ENDS | ABSENT | ABSENT | ABSENT | INTEGRATED WITH PRECEDING STAGE, INTEGRATED WITH SUBSEQUENT STAGE, SMALL DISCHARGE AMOUNT | SW ON BOTH SIDES |

MEASUREMENT DEVICE AND MEASUREMENT METHOD

CROSS REFERENCE TO RELATED APPLICATIONS

This application is a U.S. National Phase of International Patent Application No. PCT/JP2021/009819 filed on Mar. 11, 2021, which claims priority benefit of Japanese Patent Application No. JP 2020-053785 filed in the Japan Patent Office on Mar. 25, 2020. Each of the above-referenced applications is hereby incorporated herein by reference in its entirety.

FIELD

The present invention relates to a measurement device and a measurement method.

BACKGROUND

A laser Doppler blood flowmetry (hereinafter, LDF) has been put into practical use as a device for detecting a blood flow signal such as a blood flow rate (hereinafter, blood flow signal) of a subject. For example, the LDF emits laser light from a laser diode (LD) to a body tissue such as an epidermis of the subject and receives scattered light reflected from the body tissue such as an epidermis of the subject (scattered light from blood cells and scattered light from stationary tissue) with a photodiode (PD), thereby observing Doppler beat and calculating a blood flow signal.

CITATION LIST

Patent Literature

Patent Literature 1: WO 2010/023744 A

SUMMARY

Technical Problem

However, conventional LDFs have room for improvement.

The present disclosure provides a measurement device and a measurement method capable of improving external light resistance and achieving low power consumption.
Solution to Problem

BRIEF DESCRIPTION OF DRAWINGS

FIG. 12B is a diagram for describing the relationship between a first intermittent driving, a second intermittent driving, and a blood flow pulse wave.

FIG. 62 is a diagram for describing a relationship between types and characteristics of a switch set in a rapid potential setting mechanism.

DESCRIPTION OF EMBODIMENTS

Hereinafter, embodiments of the present disclosure will be described in detail with reference to the drawings. In each of the following embodiments, the same portions are denoted by the same reference signs, and repetitive description will be omitted.

The present disclosure will be described according to the following item order.

1. Description of LDF as Comparative Example Related to First Embodiment
2. First Embodiment
2.1. Configuration of Measurement Device According to First Embodiment
2.2. Configuration of Intermittent Operation Unit According to First Embodiment
2.3. Open/Close Timing of Each Switch According to First Embodiment
2.4. Effects of Measurement Device According to First Embodiment
3. Description of LDF as Comparative Example Related to Second Embodiment
4. Second Embodiment
4.1. Configuration of Measurement Device According to Second Embodiment
4.2. Configuration of Rapid Potential Setting Mechanism According to Second Embodiment
4.3. Configuration of Low Cut Filter with Rapid Potential Setting Mechanism and Non-Inverting Amplifier Circuit According to Second Embodiment
4.4. Configuration of Low Cut Filter with Rapid Potential Setting Mechanism and Inverting Amplifier Circuit According to Second Embodiment
4.5. Open/Close Timing of Each Switch According to Second Embodiment
4.6. Coupling of Analog Filter with Rapid Potential Setting Mechanism and Differential Amplifier Circuit
4.7. Coupling of Low-Pass Filter with Rapid Potential Setting Mechanism and Non-Inverting Amplifier Circuit
4.8. Coupling of Low-Pass Filter with Rapid Potential Setting Mechanism and Inverting Amplifier Circuit
4.9. Effects of Measurement Device According to Second Embodiment
5. Third Embodiment
5.1. Configuration of Measurement Device According to Third Embodiment
5.2. Configuration of Photoelectric Conversion Unit and Initial-Stage Amplifier According to Third Embodiment
5.3. Effect of Measurement Device According to Third Embodiment
6. Conclusion

1. Description of LDF as Comparative Example Related to First Embodiment

Figure 1:
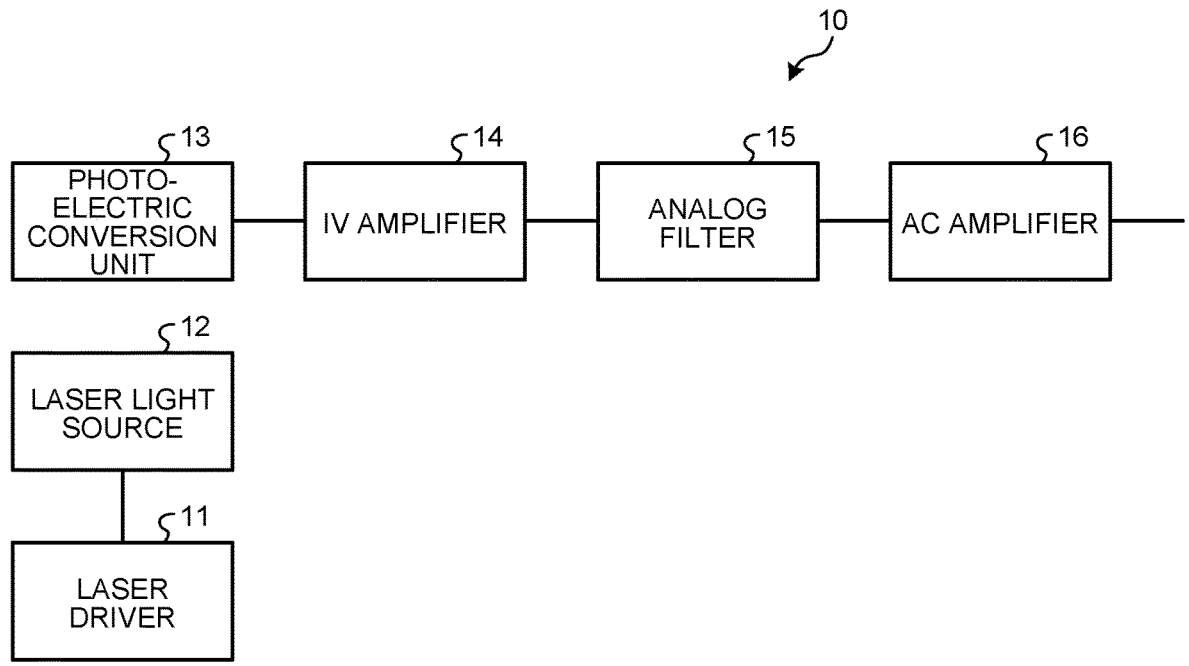
FIG. 1 is a diagram illustrating a configuration of an LDF as a comparative example.

FIG. 1 is a diagram illustrating a configuration of an LDF as a comparative example. As illustrated in FIG. 1, an LDF 10 includes a laser driver 11, a laser light source 12, a photoelectric conversion unit 13, an IV amplifier 14, an analog filter 15, and an alternate current (AC) amplifier 16.

The laser driver 11 is a device that controls power of laser light output from the laser light source 12, a driving current of the laser light source 12, and the like. The power of the laser light output from the laser light source 12 is referred to as "output optical power".

For example, the laser driver 11 causes the laser light source 12 to continuously output laser light (causes continuous light emission) in a measurement period having a length sufficient for detecting a Doppler beat. Here, in a case where the laser light source 12 is caused to continuously emit light, the laser driver 11 adjusts the output optical power so that the average of the output optical power does not exceed the upper limit of the safety standard.

In the following description, the average of the output optical power is referred to as "average power". The output optical power that is the upper limit of the safety standard is referred to as "upper limit power".

The laser light source 12 is an LD that outputs laser light under the control of the laser driver 11. The laser light source 12 outputs laser light to a body tissue such as an epidermis (in the following Examples, it is referred to as body tissue) of a subject (not illustrated). The body tissue is an example of a "test subject".

The photoelectric conversion unit 13 is a PD that receives light (scattered light) reflected when the laser light source 12 outputs laser light to the body tissue of the subject and converts the light into an electric signal. The photoelectric conversion unit 13 outputs the electric signal to the IV amplifier 14.

The IV amplifier 14 is an amplifier that amplifies the electric signal input from the photoelectric conversion unit 13. The IV amplifier 14 outputs the amplified electric signal to the analog filter 15.

The analog filter 15 is a filter that cuts off a direct current (DC) component of the electric signal input from the IV amplifier 14. The analog filter 15 outputs the electric signal obtained by cutting off the DC component to the AC amplifier 16.

The AC amplifier 16 is an amplifier that amplifies the electric signal input from the analog filter 15. The AC amplifier 16 outputs the amplified electric signal to an external device (not illustrated). The external device calculates a blood flow signal based on the Doppler beat on the basis of the electric signal output from the AC amplifier 16.

Here, a technical problem of the LDF 10 will be described. In the LDF, since the average power is set to be less than the upper limit power, when the photoelectric conversion unit 13 receives strong external light exceeding the average power, the signal-noise ratio (SN ratio) deteriorates. In addition, since the laser light source 12 has higher light emission efficiency when outputting laser light with power stronger than the average power, a loss occurs in light emission efficiency when continuously outputting laser light with the average power.

Figure 2:
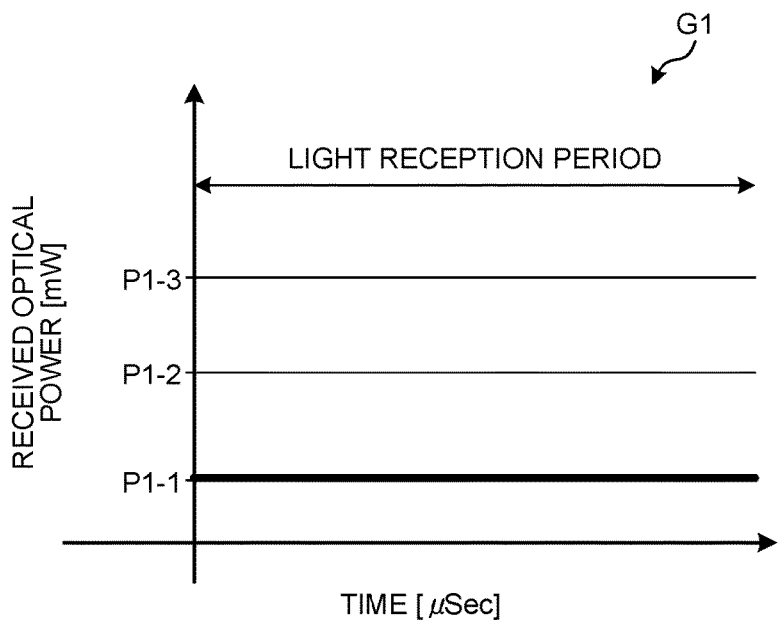
FIG. 2 is a diagram (1) for describing a technical problem of an LDF as a comparative example.

FIG. 2 is a diagram (1) for describing a technical problem of an LDF as a comparative example. FIG. 2 illustrates a state in which the amount of light becomes insufficient with respect to external light and the external light resistance becomes insufficient in continuous light emission. In Graph G1 of FIG. 2, the horizontal axis corresponds to time, and the vertical axis corresponds to received optical power of the photoelectric conversion unit 13. The power received by the photoelectric conversion unit 13 with the average power satisfying the safety standard is power P1-1. The power of external light is power P1-2. The total light reception amount obtained by adding power P1-1 and power P1-2 is a power P1-3. As illustrated in FIG. 2, when power P1-2 exceeds power P1-1, it is susceptible to noise due to modulation of external light and shot noise that increases according to the total light amount, and the accuracy decreases. In addition, when the sensitivity is adjusted with power P1-3 which is the total light reception amount, the decrease in the gain becomes large.

Figure 3:
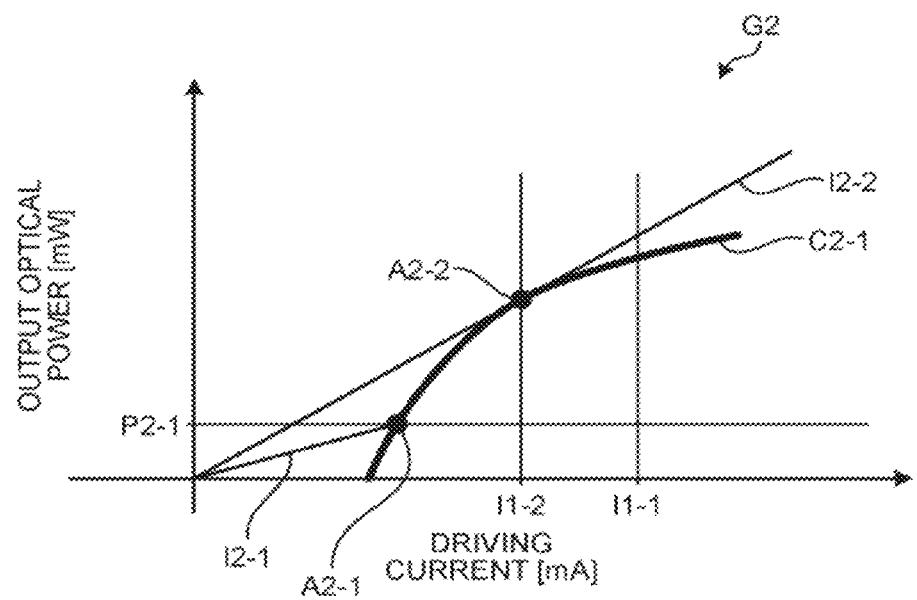
FIG. 3 is a diagram (2) for describing a technical problem of an LDF as a comparative example.

FIG. 3 is a diagram (2) for describing a technical problem of the LDF as the comparative example. In Graph G2 of FIG. 3, the horizontal axis corresponds to the driving current of the laser light source 12, and the vertical axis corresponds to the output optical power. Power P2-1 indicates the upper limit power of the safety standard. A driving current I1-1 is the upper limit of the driving current. A curve C2-1 indicates the relationship between the output optical power of the laser light source 12 and the driving current. A line connecting the origin of Graph G2 and a point on the curve C2-1 represents the light emission efficiency, and the light emission intensity per unit current increases as the inclination of the line becomes steeper.

For example, assuming that the output optical power of laser light source 12 is power P2-1, the line indicating the light emission efficiency is a line 12-1 connecting the origin and a point A2-1. The optimum point of the light emission efficiency is a point A2-2 on the curve C2-1 corresponding to the driving current I1-2, and a line connecting the origin and the point 2-2 is a line 12-2. Since the inclination of the line 12-2 is steeper than the inclination of the line 12-1, when the output optical power of the laser light source 12 is power P2-1, a loss occurs in light emission efficiency.

Figure 4:
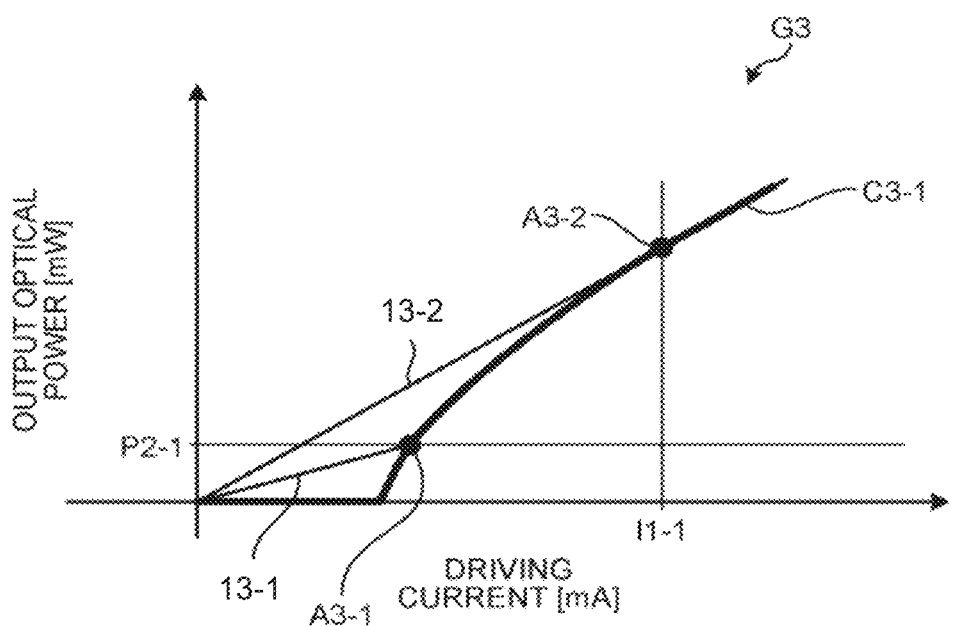
FIG. 4 is a diagram (3) for describing a technical problem of an LDF as a comparative example.

FIG. 4 is a diagram (3) for describing a technical problem of the LDF as the comparative example. The case where the optimum point of the light emission efficiency is below the upper limit of the driving current has been described with reference to FIG. 3, and a case where the optimum point of the light emission efficiency is not below the upper limit of the driving current will be described with reference to FIG. 4.

In Graph G3 of FIG. 4, the horizontal axis corresponds to the driving current of the laser light source 12, and the vertical axis corresponds to the output optical power. Power P2-1 indicates the upper limit power of the safety standard. A driving current I1-1 is the upper limit of the driving current. A curve C3-1 indicates the relationship between the output optical power of the laser light source 12 and the driving current. A line connecting the origin of Graph G3 and a point on the curve C3-1 represents the light emission efficiency, and the light emission intensity per unit current increases as the inclination of the line becomes steeper.

For example, assuming that the output optical power of the laser light source 12 is power P2-1, the line indicating the light emission efficiency is a line 13-1 connecting the origin and a point A3-1. The optimum point of the light emission efficiency is a point A3-2, and a line connecting the origin and the point 3-2 is a line 13-2. Since the inclination of the line 13-2 is steeper than the inclination of the line 13-1, even in a case where the optimum point of the light emission efficiency is not equal to or less than the upper limit of the driving current, when the output optical power of the laser light source 12 is power P2-1, a loss occurs in light emission efficiency.

Here, to increase the light emission efficiency of the laser light source 12, it is conceivable to intermittently drive the laser light source 12 to increase the output optical power. However, when the laser light source 12 is simply intermittently driven for the LDF 10, strong ringing occurs in the IV amplifier 14.

Figure 5:
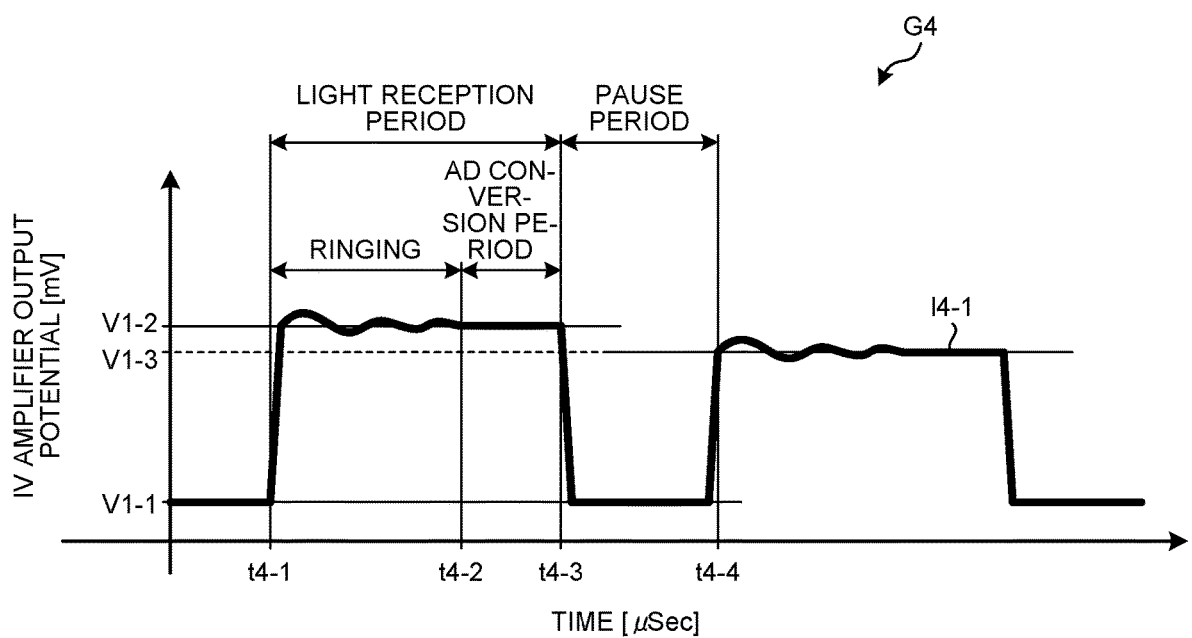
FIG. 5 is a diagram (4) for describing a technical problem of an LDF as a comparative example.

FIG. 5 is a diagram (4) for describing a technical problem of the LDF as the comparative example. In Graph G4 of FIG. 5, the horizontal axis corresponds to time, and the vertical axis corresponds to the output potential of the IV amplifier 14. A period from a time t4-1 to a time t4-3 corresponds to a period in which the photoelectric conversion unit 13 receives reflected light of intermittent light emission of the light source 12, and a period from a time t4-3 to a time t4-4 corresponds to a period in which the light source 12 is pausing light emission. The reference potential of the IV amplifier 14 is a V1-1. When the laser light source 12 is intermittently driven, the output potential of the IV amplifier 14 becomes a rectangular wave-shaped drive waveform 14-1, and for example, the output potential changes as V1-1, V1-2, V1-1, V1-3, and V1-1.

When the laser light source 12 is intermittently driven, ringing occurs in the output potential of the IV amplifier 14 at a period from the time t4-1 to the time t4-2, for example. When AD conversion is executed in an external device (not illustrated), since the potential needs to stabilize during the AD conversion period, AD conversion cannot be executed during the ringing occurrence period from the time t4-1 to the time t4-2. When AD conversion is executed after the ringing stabilizes, the laser light source 12 needs to maintain light emission between the static period and the AD conversion period. For example, assuming that the AD conversion period is from the time t2 to the time t3, the light emission of the laser light source 12 is maintained from the time t4-1 to the time t4-3, and it is difficult to increase the intermittent driving duty ratio. In addition, since the output potential of the IV amplifier 14 has an intermittent waveform, the output potential greatly fluctuates between V1-1 and V1-2. If the output potential is amplified by the analog amplifier as it is, the output amplitude becomes too large, and a clipping phenomenon occurs. In addition, the output signal includes many noise components of the intermittent drive cycle and harmonics of the intermittent drive cycle.

2. First Embodiment

<<2.1. Configuration of Measurement Device According to First Embodiment>>

Figure 6:
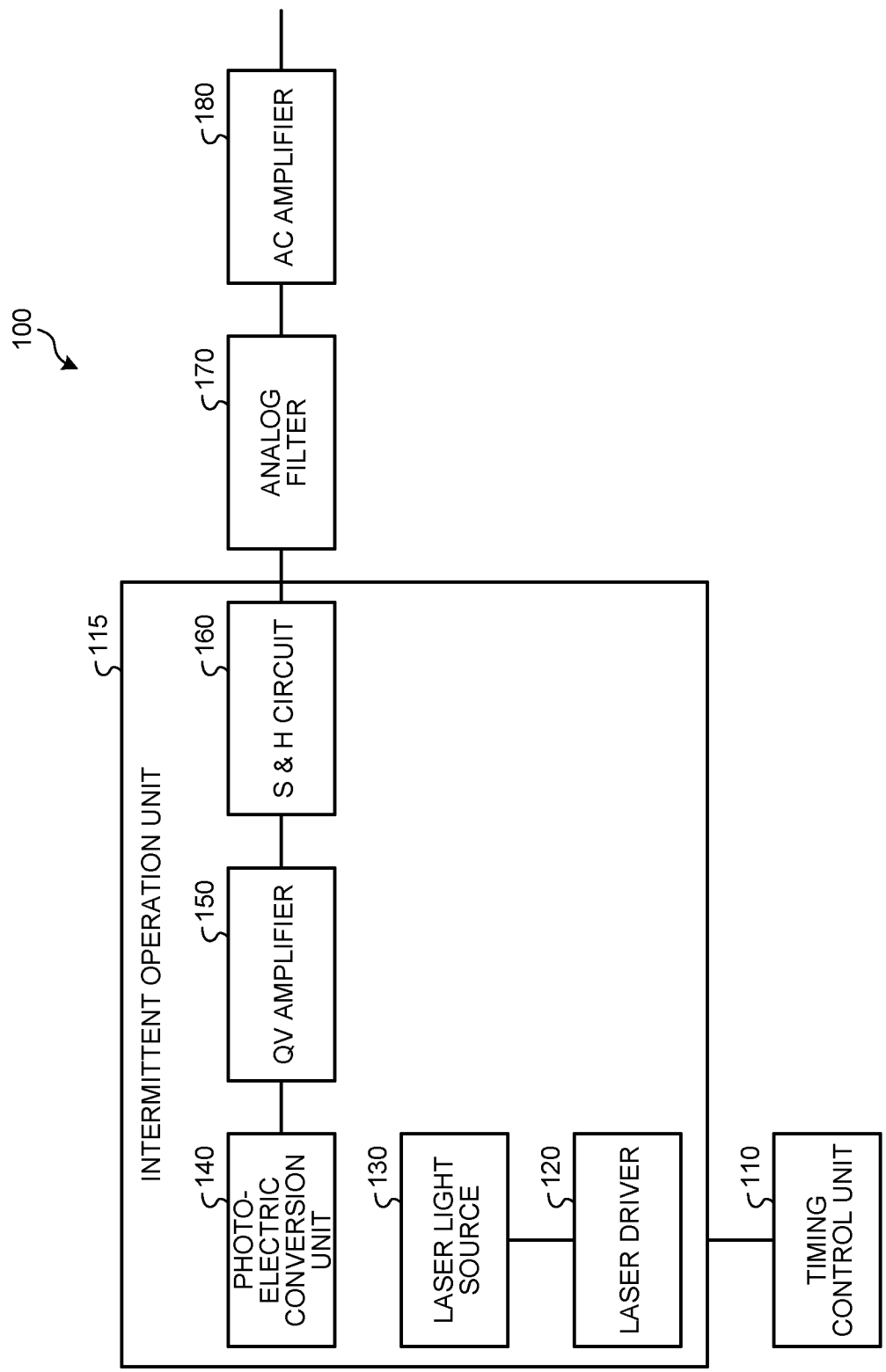
FIG. 6 is a diagram illustrating a configuration example of a measurement device according to a first embodiment.

Next, a configuration example of a measurement device according to a first embodiment will be described. FIG. 6 is a diagram illustrating a configuration example of the measurement device according to the first embodiment. As illustrated in FIG. 6, a measurement device 100 includes a timing control unit 110, an intermittent driving laser driver 120, a laser light source 130, a photoelectric conversion unit 140, a QV amplifier 150, an S & H circuit 160, an analog filter 170, and an AC amplifier 180.

The intermittent driving laser driver 120, the laser light source 130, the photoelectric conversion unit 140, the QV amplifier 150, and the S & H circuit 160 are collectively referred to as an intermittent operation unit 115.

The timing control unit 110 is a processing unit that controls a timing at which the intermittent operation unit 115 is intermittently operated (intermittently driven). The timing control unit 110 is an example of a "drive control unit". For example, the timing control unit 110 outputs each SW control signal to the intermittent driving laser driver 120, the QV amplifier 150, and the S & H circuit 160 of the intermittent operation unit 115. In the intermittent operation (intermittent driving), pause and driving are repeatedly performed.

The intermittent driving laser driver 120 is a device that controls output optical power of the laser light source 130, a driving current of the laser light source 130, and the like. The intermittent driving laser driver 120 intermittently outputs laser light from the laser light source 130 based on the SW control signal output from the timing control unit 110. Here, when intermittently operating the laser light source 130, the intermittent driving laser driver 120 intermittently outputs laser light from the laser light source 130 with an upper limit power larger than the upper limit power limited by continuous light emission (intermittent light emission).

In the following description, the output optical power that is the upper limit on the safety standard in the case of continuous light emission is referred to as "first upper limit power". The output optical power that is the upper limit on the safety standard in the case of intermittent light emission is referred to as "second upper limit power".

Figure 7:
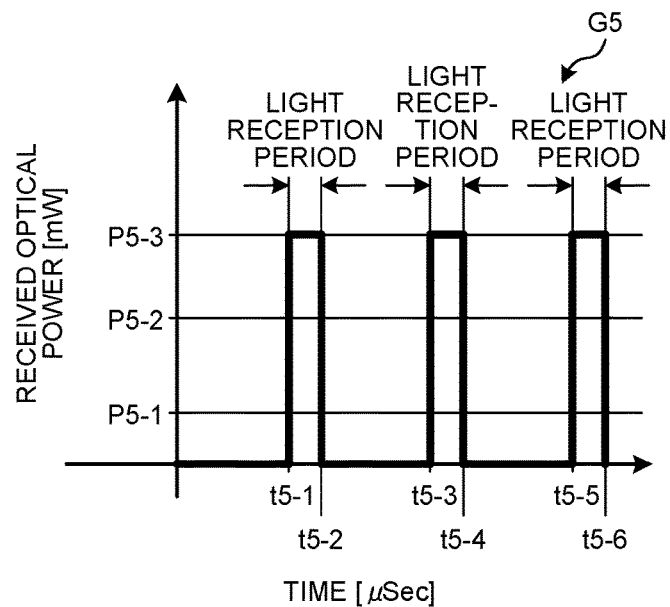
FIG. 7 is a diagram illustrating an example of intermittent light emission of a laser light source according to the first embodiment.

FIG. 7 is a diagram illustrating an example of intermittent light emission of the laser light source 130 according to the first embodiment. FIG. 7 illustrates a state in which external light resistance is improved by intermittent light emission and intermittent light reception. In Graph G5 of FIG. 7, the horizontal axis corresponds to time, and the vertical axis corresponds to the received optical power of the photoelectric conversion unit 13. The light reception period of the photoelectric conversion unit 13 is set to t5-1 to t5-2, t5-3 to t5-4, and t5-5 to t5-6. The first upper limit power is power P5-1. The power of external light is power P5-2. The second upper limit power is power P5-3.

As illustrated in FIG. 7, the intermittent light emission is limited by the first upper limit power or the second upper limit power far exceeding the power of the external light. Therefore, the influence of an increase in shot noise due to external light can be reduced. In addition, even when a sensitivity adjustment is executed with the total light reception amount obtained by adding power P5-2 of the external light and the second upper limit power P5-3, the decrease in the gain becomes small. Further, when the laser light source 130 intermittently emits light, the intermittent driving laser driver 120 can improve the light emission efficiency by adjusting the driving current to the driving current I1-2 illustrated in FIG. 3 (alternatively, the drive current I1-1 illustrated in FIG. 4).

The description returns to FIG. 6. The laser light source 130 is an example of a "light source" that intermittently outputs laser (intermittently emits light) based on the control of the intermittent driving laser driver 120, and is an LD here. The laser light source 130 outputs laser to a body tissue of a subject (not illustrated).

The photoelectric conversion unit 140 is an example of a "light receiving element" that receives (intermittently receives) light (scattered light) reflected when the laser light source 130 intermittently outputs laser to the body tissue of the subject and converts the light into an electric signal, and is a PD here. The photoelectric conversion unit 140 outputs a charge (electric signal) corresponding to the amount of light to the QV amplifier 150.

The QV amplifier 150 is an example of an "amplifier that amplifies a charge with an integration circuit" that accumulates a charge corresponding to the amount of light input from the photoelectric conversion unit 140 with an integration circuit and converts the charge into a potential difference. The QV amplifier 150 outputs the amplified electric signal to the S & H circuit 160. The QV amplifier 150 can reduce power consumption by intermittently operating based on the SW control signal output from the timing control unit 110. In addition, since the output voltage (electric signal) of the QV amplifier 150 changes to a sawtooth wave-shaped drive waveform, ringing is less likely to occur as compared with the rectangular wave-based electric signal output from the IV amplifier of the comparative example, and it is suitable for minute signal amplification.

The QV amplifier 150 is a QV amplifier with an electronic shutter. While the laser light source 130 is not emitting light, the photoelectric conversion unit 140 and the QV amplifier 150 are temporarily separated from each other by the electronic shutter. This can discard charges generated by external light other than light emission and improve external light resistance. The electronic shutter is an example of a "disconnection unit" that disconnects from the photoelectric conversion unit 140.

The sample and hold (S & H) circuit 160 is a circuit that fixes an output potential of an electric signal output from the QV amplifier 150. The S & H circuit 160 outputs the electric signal to the analog filter 170 while fixing the output potential of the electric signal. The S & H circuit 160 is an example of a "potential retention circuit".

Figure 8:
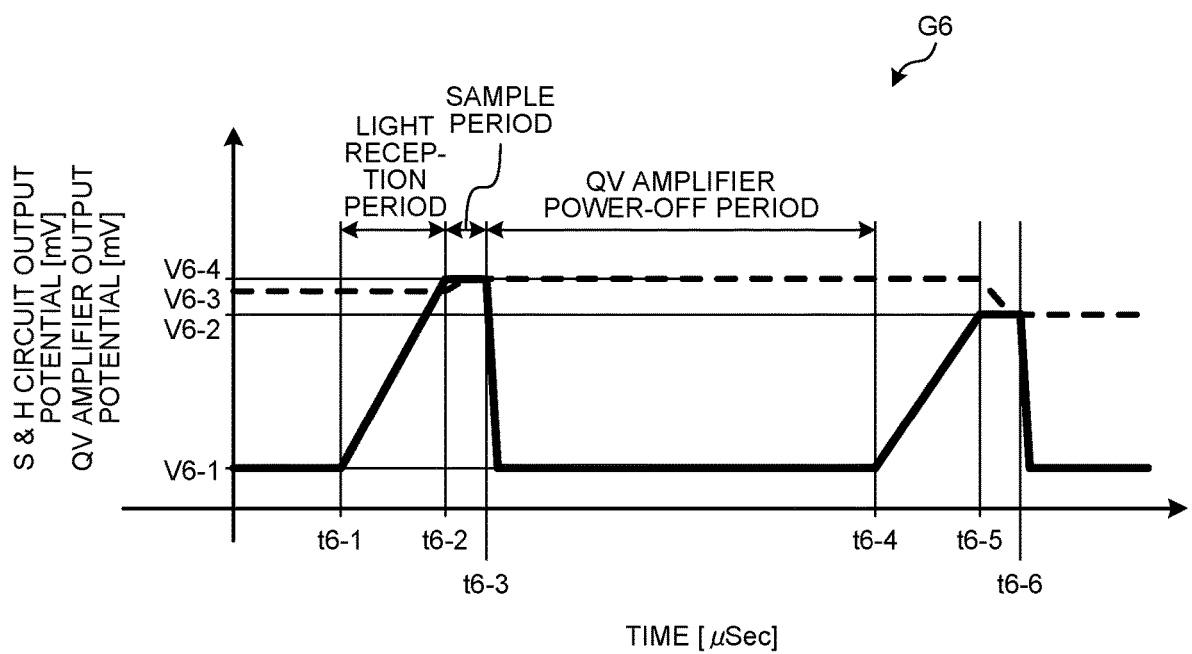
FIG. 8 is a diagram illustrating temporal changes of an output potential of a QV amplifier and an output potential of an S & H circuit according to the first embodiment.

Here, the output potential of the QV amplifier 150 and the output potential of the S & H circuit 160 when the photoelectric conversion unit 140 intermittently receives light will be described. FIG. 8 is a diagram illustrating temporal changes of the output potential of the QV amplifier 150 and the output potential of the S & H circuit 160 according to the first embodiment. In Graph G6 of FIG. 8, the horizontal axis corresponds to time, and the vertical axis corresponds to the output potential of the QV amplifier 150 or the output potential of the S & H circuit 160. A period from time t6-1 to time t6-2 is set as a light reception period of the photoelectric conversion unit 140. A period from time t6-2 to t6-3 is defined a sample period of the S & H circuit 160. A period from time t6-3 to t6-4 is a QV amplifier power-off period. The reference potential of the QV amplifier is V6-1. The output potential of the S & H circuit 160 before time t6-1 is V6-3.

When the light reception period of the photoelectric conversion unit 140 is started at time t6-1, the output potential of the QV amplifier 150 gradually increases, and the output potential becomes V6-4 at time t6-2. In the sample period from time t6-2 to t6-3, the output potential of the S & H circuit 160 is fixed to V6-4. In the pause period from time t6-3 to time t6-4, the output potential of the QV amplifier 150 is V6-1, but the output potential of the S & H circuit 160 is V6-4.

When the light reception period of the photoelectric conversion unit 140 is started at time t6-4, the output potential of the QV amplifier 150 gradually increases, and the output potential becomes V6-2 at time t6-5. In the sample period from time t6-5 to t6-6, the output potential of the S & H circuit 160 is fixed to V6-2.

As illustrated in FIG. 8, since the output potential of the QV amplifier 150 has a sawtooth wave-shaped drive waveform, ringing is extremely small. The ringing occurring in the QV amplifier 150 is only ringing due to differential discontinuity. QV amplifier 150 can shift to the sample period immediately after the light reception period. Since the QV amplifier 150 is an amplifier that performs amplification with the integration circuit, the output potential can be maintained even when the photoelectric conversion unit 140 and the QV amplifier 150 are separated at the time of completion of light emission. In addition, due to the characteristics of the QV amplifier 150, the light emission period and the light reception period can be freely set, and unnecessary external light reception can be prevented.

Further, since the output potential of the S & H circuit 160 is continuously changed, the electric signal of the S & H circuit can be amplified as an AC signal by the AC amplifier 180 after being processed by the analog filter 170.

The description returns to FIG. 6. The analog filter 170 is a filter that cuts off a DC component of the electric signal input from the S & H circuit 160. The analog filter 170 outputs the electric signal obtained by cutting off the DC component to the AC amplifier 180. The analog filter 170 may be an RC filter.

The AC amplifier 180 is an amplifier that amplifies the electric signal input from the analog filter 170. The AC amplifier 180 outputs the amplified electric signal to an external device (not illustrated). The external device calculates a blood flow signal based on the Doppler beat on the basis of the electric signal output from the AC amplifier 180. The AC amplifier 180 is an example of a "subsequent-stage amplifier".

<<2.2. Configuration of Intermittent Operation Unit According to First Embodiment>>

Figure 9:
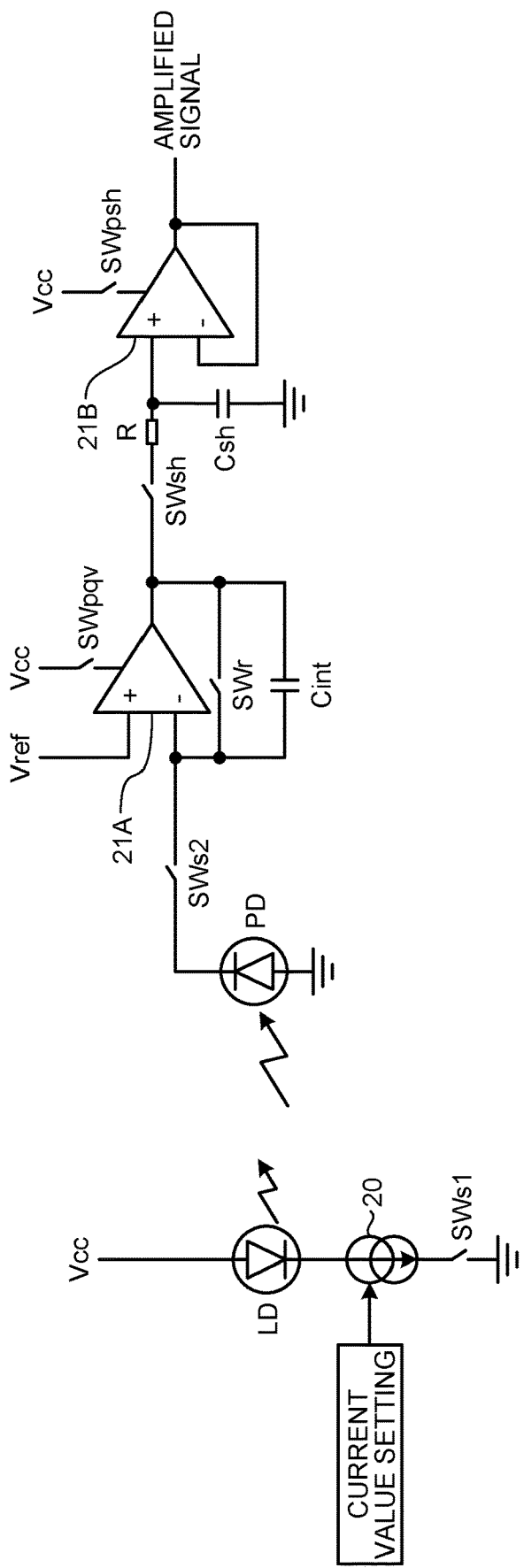
FIG. 9 is a diagram illustrating a configuration of an intermittent operation unit according to the first embodiment.

FIG. 9 is a diagram illustrating a configuration of the intermittent operation unit 115 according to the first embodiment. For example, in FIG. 9, a current source 20 to which the current is set and switch SWs1 correspond to the intermittent driving laser driver 120. The LD corresponds to the laser light source 130.

The PD in FIG. 9 corresponds to the photoelectric conversion unit 140. Operational amplifier 21A, switch SWs2, switch SWpqv, switch SWr, and capacitor Cint correspond to the QV amplifier 150. Switch SWs2 corresponds to an electronic shutter. Operational amplifier 21B, switch SWsh, switch SWpsh, resistor R, and capacitor Csh correspond to the S & H circuit 160. The amplified signal output from operational amplifier 21B corresponds to the electric signal output from the S & H circuit 160.

Opening and closing of switches SWs1, SWs2, SWpqv, SWr, SWsh, and SWpsh illustrated in FIG. 9 is controlled by the SW control device output from the timing control unit 110. When switch SWs1 is turned on, the LD emits laser light, and when switch SWs1 is turned off, the LD stops emitting laser light. When switch SWs2 is turned on, electric charges generated in the PD are transferred to the QV amplifier 150, and when switch SWs2 is turned off, the electric charges are blocked. When switch SWpqv is turned on, the QV amplifier 150 is powered on, and when switch SWpqv is turned off, the QV amplifier 150 is cut off. When switch SWr is turned on, the integration operation is stopped, and the accumulated charge is discarded, and when switch SWr is turned off, the integration operation is executed. When switch SWsh is turned on, the output of the QV amplifier 150 is sampled and, and when switch SWsh is turned off, the output of the QV amplifier 150 is held. When switch SWpsh is turned on, the S & H circuit 160 is powered on, and switch SWpsh is turned off, the S & H circuit 160 is powered off.

<<2.3. Open/Close Timing of Each Switch According to First Embodiment>>

Figure 10:
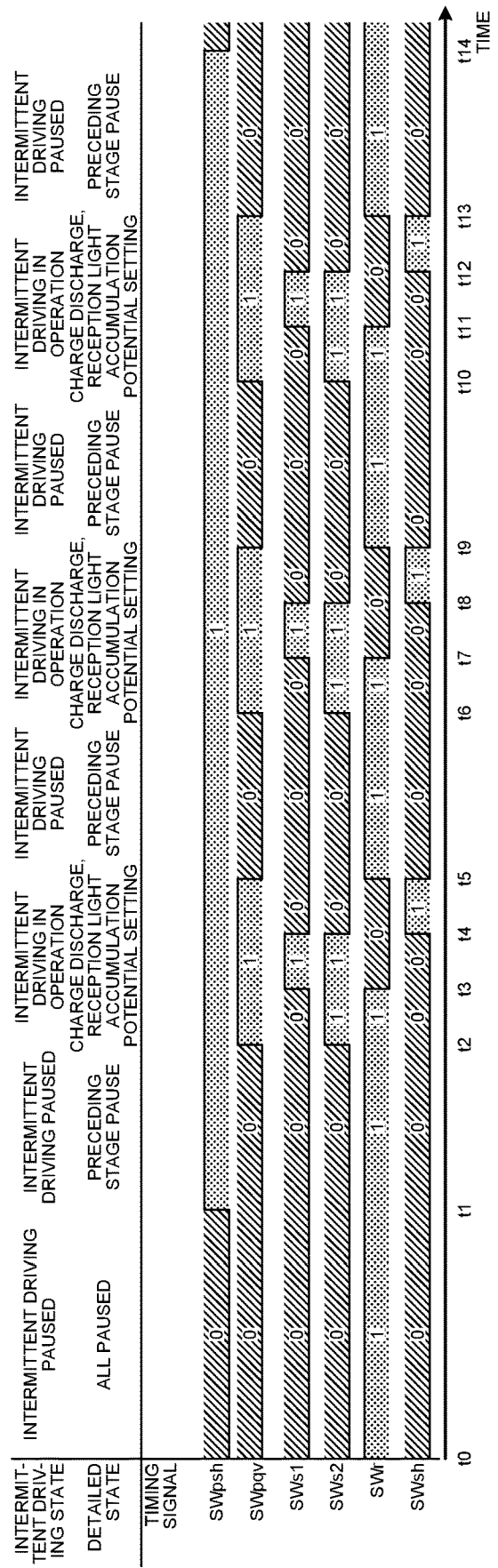
FIG. 10 is a diagram for describing an example of opening/closing timing of each switch according to the first embodiment.

FIG. 10 is a diagram for describing an example of opening/closing timing of each switch according to the first embodiment. In FIG. 10, a section having a value "0" indicates that the switch is open, and a section having a value "1" indicates that the switch is closed. The horizontal axis in FIG. 10 corresponds to time. A section before time t1 and a section after time t14 indicate pause periods during which measurement is not performed, where the intermittent operation unit 115 pauses its operation. A section from time t1 to time t14 indicates a measurement period in which measurement is performed, where the intermittent operation unit 115 repeats a series of measurements while intermittently pausing laser emission and amplification of electric signals. FIG. 10 illustrates an example in which measurement is continuously executed three times for the sake of simplicity. However, it is effective that measurement is continuously repeated several 100 times or more in an actual measurement period.

The opening/closing timing of switch SWpsh will be described. Switch SWpsh is in an open state during a pause period of from time t0 to time t1. Switch SWpsh is in a closed state during a measurement period of from time t1 to time t14. Switch SWpsh is in an open state after time t14 which is a pause period. Although not illustrated, switch SWpsh may repeat the opening/closing timing illustrated in FIG. 10 to start the measurement period again after time t14.

The opening/closing timing of switch SWpqv will be described. Switch Wpqv is in an open state during a pause period of from time t0 to time t1. Switch Wpqv maintains the open state between times t1 and t2 when the measurement period starts. Switch SWpqv is in a closed state between times t2 and t5. Switch SWpqv is in an open state between times t5 and t6. Switch SWpqv is in a closed state between times t6 and t9. Switch SWpqv is in an open state between times t9 and t10. Switch SWpqv is in a closed state between times t10 and t13. Switch SWpqv is in an open state between times t13 and t14. Switch SWpqv maintains the open state after time t14 which is a pause period. Although not illustrated, switch SWpqv may repeat the opening/closing timing illustrated in FIG. 10 to start the measurement period again after time t14.

The opening/closing timing of switch SWs1 will be described. Switch SWs1 is in an open state during a pause period of from time t0 to time t1. Switch SWs1 maintains the open state between times t1 and t3 when the measurement period starts. Switch SWs1 is in a closed state between times t3 and t4. Switch SWs1 is in an open state between times t4 and t7. Switch SWs1 is in a closed state between times t7 and t8. Switch SWs1 is in an open state between times t8 and t11. Switch SWs1 is in a closed state between times t11 and t12. Switch SWs1 is in an open state between times t12 and t14. Switch SWs1 maintains the open state after time t14 which is a pause period. Although not illustrated, switch SWs1 may repeat the opening/closing timing illustrated in FIG. 10 to start the measurement period again after time t14.

The opening/closing timing of switch SWs2 will be described. Switch SWs2 is in an open state during a pause period of from time t0 to time t1. Switch SWs2 maintains the open state between times t1 and t2 when the measurement period starts. Switch SWs2 is in a closed state between times t2 and t4. Switch SWs2 is in an open state between times t4 and t6. Switch SWs2 is a closed state between times t6 and t8. Switch SWs2 is in an open state between times t8 and t10. Switch SWs2 is in a closed state between times t10 and t12. Switch SWs2 is in an open state between times t12 and t14. Switch SWs2 maintains the open state after time t14 which is a pause period. Although not illustrated, the switch SWs2 may repeat the opening/closing timing illustrated in FIG. 10 to start the measurement period again after time t14.

The opening/closing timing of switch SWr will be described. Switch SWr is in a closed state during a pause period of from time t0 to time t1. Switch SWr maintains the closed state between times t1 and t3 when the measurement period starts. Switch SWr is in an open state between times t3 and t5. Switch SWr is a closed state between times t5 and t7. Switch SWr is in an open state between times t7 and t9. Switch SWr is a closed state between times t9 and t11. Switch SWr is in an open state between times t11 and t13. Switch SWr is in a closed state between times t13 and t14. Switch SWr maintains the closed state after time t14 which is a pause period. Switch SWr may repeat the opening/closing timing illustrated in FIG. 10 to start the measurement period again after time t14.

The opening/closing timing of switch SWsh will be described. Switch SWsh is in an open state during a pause period of from time t0 to time t1. Switch SWsh maintains the open state between times t1 and t4 when the measurement period starts. Switch SWsh is in a closed state between times t4 and t5. Switch SWsh is in an open state between times t5 and t8. Switch SWsh is in a closed state between times t8 and t9. Switch SWsh is in an open state between times t9 and t12. Switch SWsh is in a closed state between times t12 and t13. Switch SWsh is in an open state between times t13 and t14. Switch SWsh maintains the open state after time t14 which is a pause period. Although not illustrated, switch SWsh may repeat the opening/closing timing illustrated in FIG. 10 to start the measurement period again after time t14.

In the times from t2 to t5, t6 to t9, and t10 to t13 in FIG. 10, the laser light source 130 (LD) emits light, and the photoelectric conversion unit 140 (PD) receives the light. The QV amplifier 150 accumulates charges in Cint, and the S & H circuit 160 fixes the potential of the electric signal output from the QV amplifier 150 and outputs the amplified signal to the analog filter 170.

<<2.4. Effects of Measurement Device According to First Embodiment>>

The measurement device 100 according to the first embodiment intermittently drives the laser light source 130 to enhance the output optical power at the time of light emission while satisfying the safety standard, which can intermittently drive the laser light source with the driving current having the maximum light emission efficiency and can minimize the power consumption of the laser light source.

The QV amplifier 150 of the measurement device 100 is a QV amplifier with an electronic shutter. While the laser light source 130 is not emitting light, the photoelectric conversion unit 140 and the QV amplifier 150 are temporarily separated from each other by the electronic shutter (switch SWs2). This can discard an electric signal due to external light other than light emission and improve external light resistance. Note that the electronic shutter can be omitted in the case of a configuration that can suppress mixing of external light with another method.

The measurement device 100 combines the QV amplifier 150 and the S & H circuit 160, increases the potential with the integration circuit of the QV amplifier 150, and fixes the increased potential with the S & H circuit 160. This can stably amplify a minute signal of 1/1000 or less of the DC signal and can suppress generation of noise even when intermittent driving is performed.

The measurement device 100, which intermittently drives the QV amplifier 150, can suppress power consumption.

3. Description of LDF as Comparative Example Related to Second Embodiment

Figure 11A:
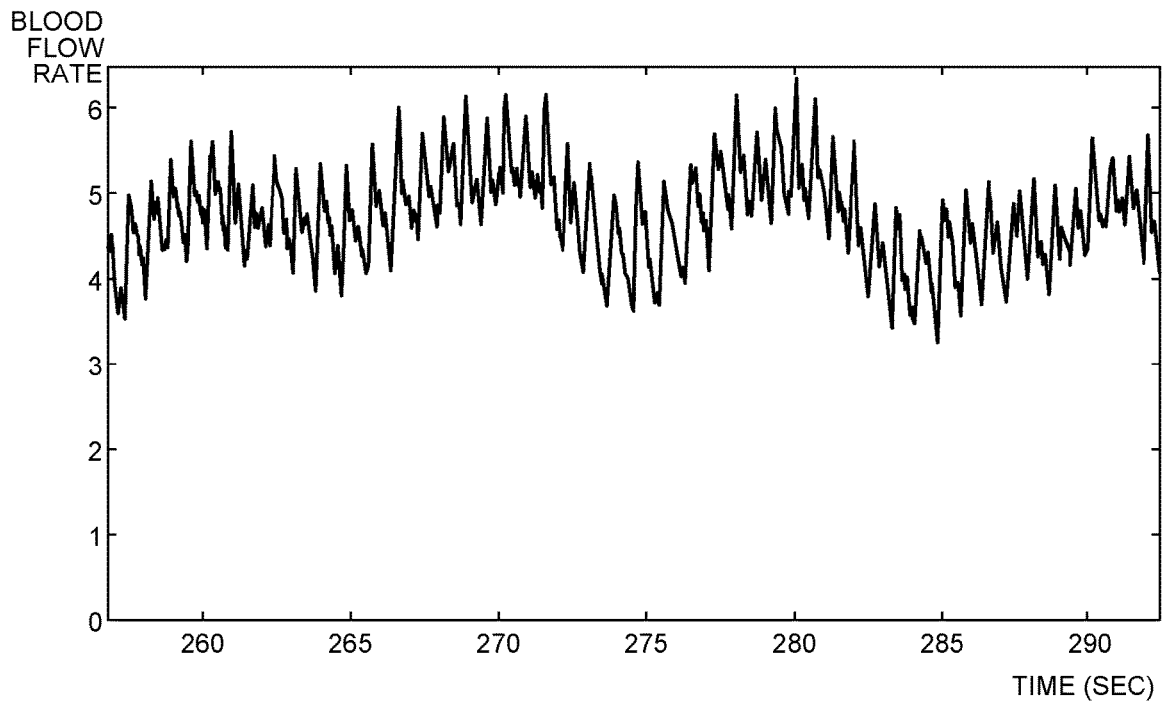
FIG. 11A is a diagram illustrating an example of a blood flow rate change.

First, characteristics of the blood flow signal will be described. FIG. 11A is a diagram illustrating an example of a change in blood flow rate, which is a type of blood flow signal. The horizontal axis of the graph of FIG. 11A corresponds to time (seconds), and the vertical axis corresponds to blood flow rate. For example, the blood flow change illustrated in FIG. 11A corresponds to the blood flow signal. The blood flow signal includes a pulse signal that beats at a frequency of about once per second. The blood flow signal includes change information associated with respiration that varies at intervals of several seconds to several tens of seconds. The blood flow signal also includes change information associated with blood pressure variation associated with an autonomic nerve that varies at a time constant of ten-plus seconds to several tens of seconds.

In view of the characteristics of the blood flow information, it is desirable to measure the blood flow information at a frequency of about 30 sps or more to obtain information regarding the pulse when acquiring physical condition information at a certain time point. In addition, to obtain information regarding respiration and autonomic nerve activity, it is desirable to measure a series of blood flow signals having a length of several tens of seconds.

Here, description will be made assuming that a series of blood flow signals for 1 minute (60 seconds) is measured. The sampling frequency of the Doppler beat signal detection when measuring the blood flow signal is assumed to be 32 kHz.

Here, in a case where the LDF 10 as the comparative example described in FIG. 1 is intermittently operated at a frequency of about 33 sps, the time constant of the analog filter 15 is relatively large. Therefore, it takes 10 msec or more until the output potential of the preceding-stage amplifier (IV amplifier 14) reaches a plateau after being set, which interrupts reduction in power consumption due to power-off of the preceding-stage amplifier. The preceding-stage amplifier (pre-stage circuit) described herein refers to a circuit that is located in a preceding stage of the analog filter and outputs an electric signal to the analog filter. The preceding-stage amplifier does not indicate only an amplifier circuit of an electric signal, but indicates a general active circuit that outputs an analog electric signal. An active circuit that is located at a subsequent stage of the analog filter and receives an electric signal output from the analog filter will be referred to as a subsequent-stage amplifier (subsequent-stage circuit). The subsequent-stage amplifier does not indicate only an amplifier circuit of an electric signal, but indicates a general active circuit that receives an input of an analog electric signal.

Figure 11B:
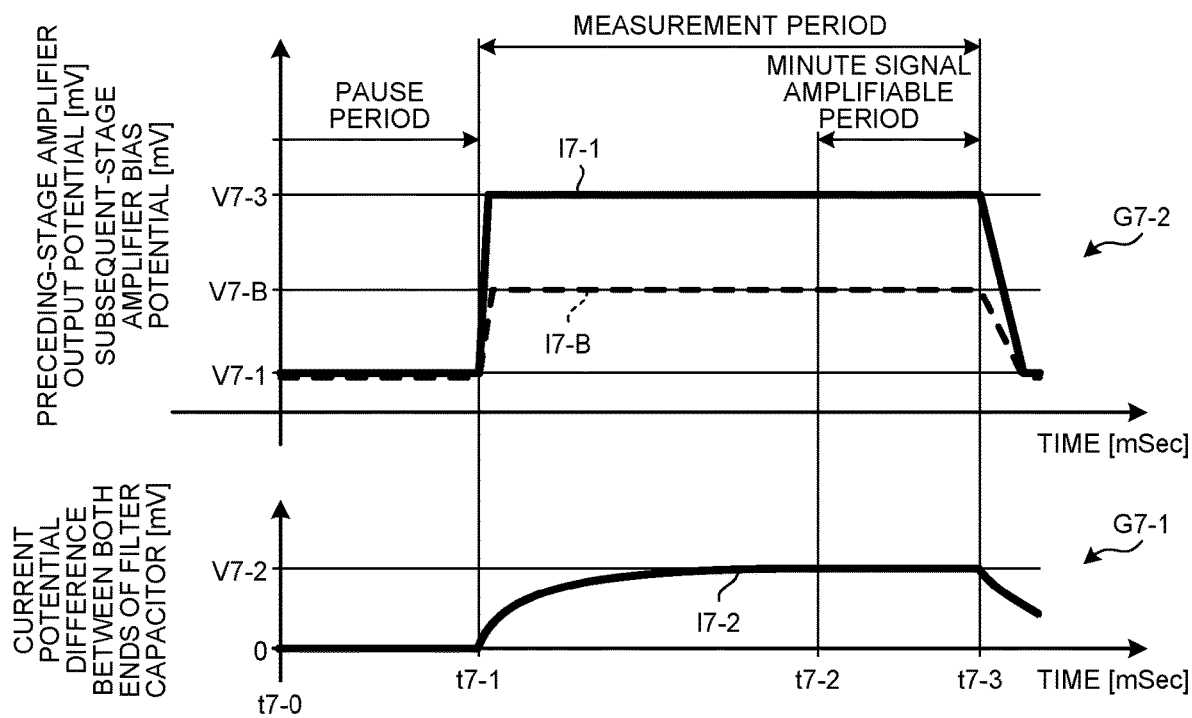
FIG. 11B is a diagram (5) for describing a technical problem of an LDF as a comparative example.

FIG. 11B is a diagram (5) for describing a technical problem of the LDF as the comparative example. In Graphs G7-1 and G7-2 of FIG. 11B, the horizontal axis corresponds to time. In Graph G7-2, the vertical axis corresponds to the output potential of the preceding-stage amplifier (IV amplifier 14). In Graph G7-1, the vertical axis corresponds to the potential difference between both ends of a filter capacitor. The filter capacitor is a capacitor included in the analog filter 15. A period from time t7-0 to t7-1 is a pause period. A period from time t7-1 to t7-3 is a measurement period (operation period).

The output signal of the preceding-stage amplifier and the pause potential of a BIAS potential of the subsequent-stage circuit are V7-1. The DC potential at the time of measuring the output signal of the preceding-stage amplifier is V7-3. The BIAS potential at the time of measuring the subsequent-stage circuit is V7-B. A potential obtained by subtracting the BIAS potential at the time of measuring the subsequent-stage circuit from the DC potential at the time of measuring the output signal of the preceding-stage amplifier is V7-2. The relationship between the time and the preceding-stage amplifier output potential is line 17-1. The relationship between the time and the BIAS potential of the subsequent-stage circuit is line 17-B. The relationship between the time and the potential difference between both ends of the filter capacitor is line 17-2. In FIG. 11B, since it takes time until the potential of an analog filter 270 stabilizes, a minute signal amplifiable period is from time t7-2 to time t7-3.

As illustrated in FIG. 11B, the output potential of the preceding-stage amplifier and the BIAS potential of the subsequent-stage circuit can rise at a speed corresponding to the sampling frequency of the sensor. Here, since the analog filter 15 has a time constant corresponding to the cutoff frequency, it takes time for the output potential to converge to the BIAS potential of the subsequent-stage circuit. For example, when the cutoff frequency is 100 Hz, the time constant is about 1.6 msec, and it takes about 11 msec to stabilize to $\frac{1}{1000}$ of the DC amplitude. When the length of the measurement period of the intermittent operation is not sufficiently longer than 11 msec, power loss corresponding to the stabilization time occurs. Assuming that the necessary measurement period is 10 msec, operation of 21 msec is required, and the operation efficiency is ½ or less. Therefore, a method for shortening the time until the DC value of the analog filter 15 stabilizes is required.

4. Second Embodiment

<<4.1. Configuration of Measurement Device According to Second Embodiment>>

Figure 12A:
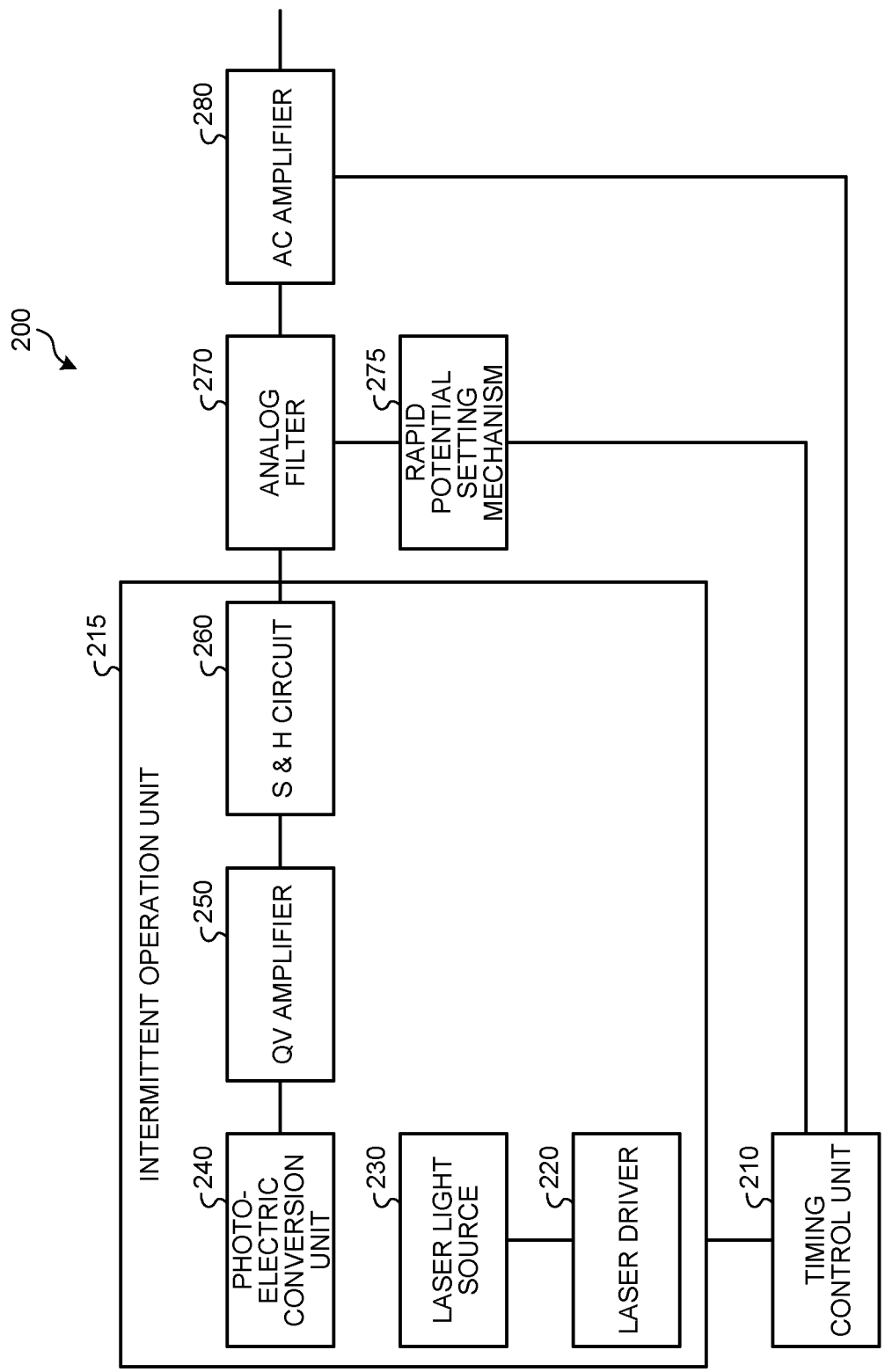
FIG. 12A is a diagram illustrating a configuration example of a measurement device according to a second embodiment.

Next, a configuration describing of a measurement device according to a second embodiment will be described. FIG. 12A is a diagram illustrating a configuration example of the measurement device according to the second embodiment. As illustrated in FIG. 12A, a measurement device 200 includes a timing control unit 210, an intermittent driving laser driver 220, a laser light source 230, a photoelectric conversion unit 240, a QV amplifier 250, an S & H circuit 260, an analog filter 270, a rapid potential setting mechanism 275, and an AC amplifier 280.

The intermittent driving laser driver 220, the laser light source 230, the photoelectric conversion unit 240, the QV amplifier 250, and the S & H circuit 260 are collectively referred to as an intermittent operation unit 215.

The timing control unit 210 is a processing unit that controls the timing of intermittently operating the intermittent operation unit 215 and the AC amplifier 280. The timing control unit 210 is an example of a "drive control unit". The timing control unit 210 controls a switch of the rapid potential setting mechanism. For example, the timing control unit 210 outputs each SW control signal to the intermittent driving laser driver 220, the QV amplifier 250, and the S & H circuit 260, the rapid potential setting mechanism 275, and the AC amplifier 280 of the intermittent operation unit 215.

The description of the intermittent driving laser driver 220, the laser light source 230, the photoelectric conversion unit 240, the QV amplifier 250, and the S & H circuit 260 is the same as the description of the intermittent driving laser driver 120, the laser light source 130, the photoelectric conversion unit 140, the QV amplifier 150, and the S & H circuit 160 described in the first embodiment.

The analog filter 270 is a filter that cuts off the DC component of the electric signal input from the S & H circuit 260. The analog filter 270 outputs the electric signal obtained by cutting off the DC component to the AC amplifier 280. As described later, the analog filter 270 is connected to the rapid potential setting mechanism 275, and the potential rapidly stabilizes. The rapid potential setting mechanism 275 is an example of a "potential setting mechanism unit".

The rapid potential setting mechanism 275 rapidly stabilizes the potential of the analog filter 270 by closing a switch that shortens the time constant of the analog filter 270 in synchronization with the return from the pause on the basis of the SW control signal output from the timing control unit 210. For example, when the switch is closed, the rapid potential setting mechanism 275 connects a potential setting resistor to a resistor of the analog filter 270 in parallel to temporarily decrease the time constant and rapidly stabilize the potential.

Here, the timing control unit 210 causes the intermittent operation unit 215 to perform a first intermittent driving and causes the intermittent operation unit 215 and the AC amplifier 280 to perform a second intermittent driving. FIG. 12B is a diagram for describing the relationship between the first intermittent driving, the second intermittent driving, and a blood flow pulse wave. Graph G1-1 in FIG. 12B is a graph illustrating the relationship between the blood flow pulse wave and time. Graph G1-2 is an enlarged graph of a portion A1-1 of Graph G1-1. The vertical axis of Graphs G1-1 and G1-2 corresponds to the blood flow pulse wave, and the horizontal axis corresponds to time.

Graph G1-3 is a graph indicating the timing of the second intermittent drive. The vertical axis of Graph G1-3 corresponds to the output optical power, and the horizontal axis corresponds to time. In the second intermittent driving, a measurement period and a pause period are repeated. For example, the measurement period is 10 ms, and the pause period is 20 ms (about 33 Hz).

Graph G1-4 is a graph illustrating the timing of the first intermittent drive. Graph G1-4 is an enlarged view of a portion A1-3 of Graph G1-3. The vertical axis of Graph G1-4 corresponds to the output optical power, and the horizontal axis corresponds to time. In the first intermittent driving, a light emission period and an extinction period are repeated. For example, the emission period is 7.8 µs and the extinction period is 23.4 µs. At this time, the light emission cycle is 31.2 µs, and the sampling frequency is about 32 kHz.

For example, in the example illustrated in FIG. 12B, since the measurement frequency is 33% and the light emission rate is 25%, the light emission duty ratio is about 8.3% (33%×25%).

Figure 13:
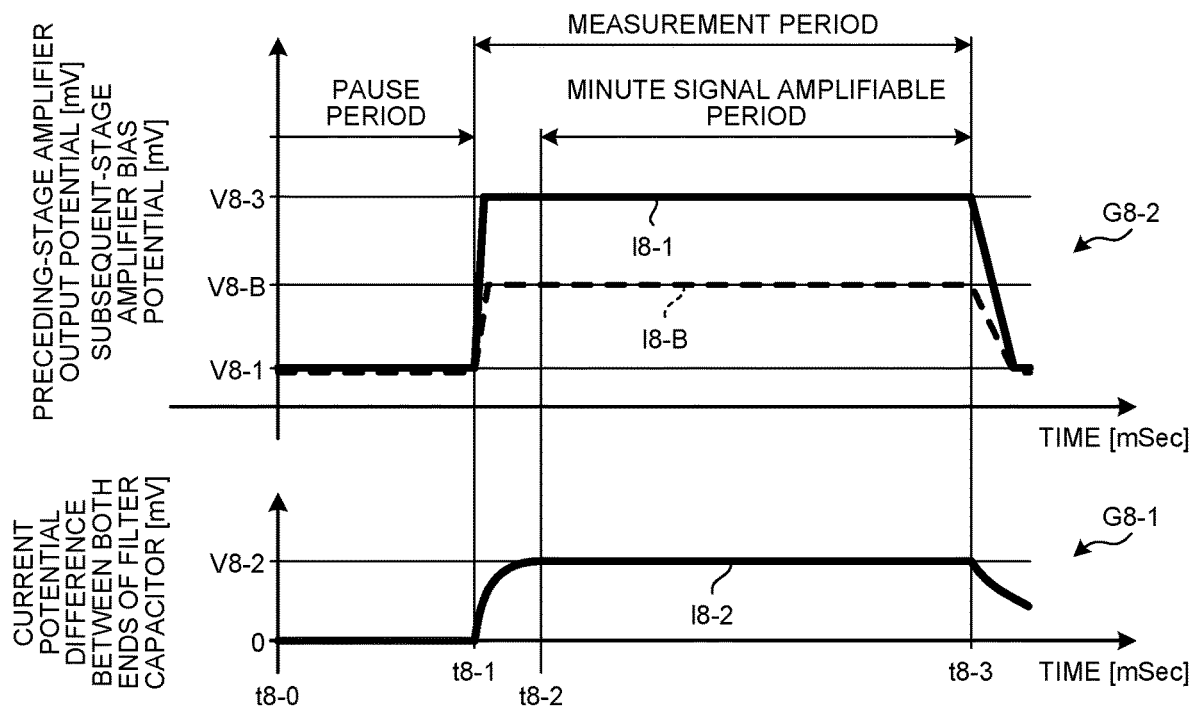
FIG. 13 is a diagram (1) for describing the relationship between a rising of an output of a preceding-stage amplifier and an output of an analog filter.

FIG. 13 is a diagram (1) for describing the relationship between the rising of the output of the preceding-stage amplifier and the output of the analog filter 270. In Graphs G8-1 and G8-2 of FIG. 13, the horizontal axis corresponds to time. In Graph 8-2, the vertical axis corresponds to the output potential of the preceding-stage amplifier (S & H circuit 260). In Graph G8-1, the vertical axis corresponds to the potential difference between both ends of a filter capacitor. The filter capacitor is a capacitor included in the analog filter 270. A period from time t8-0 to t8-1 is a pause period. A period from time t8-1 to t8-3 is a measurement period. For example, the pause period is a pause period of the second intermittent driving, and the preceding-stage amplifier is in a pause state. For example, the measurement period is a measurement period of the second intermittent driving, and the preceding-stage amplifier is in an operation state and outputs a measurement value.

The potential of the output terminal during the pause period of the output signal of the preceding-stage amplifier and the BIAS potential of the subsequent-stage circuit is V8-1. The DC potential at the time of measuring the output signal of the preceding-stage amplifier during the measurement period is V8-3. The BIAS potential at the time of measuring the subsequent-stage circuit is V8-B. A potential obtained by subtracting the BIAS potential at the time of measuring the subsequent-stage circuit from the DC potential at the time of measuring the output signal of the preceding-stage amplifier is V8-2. The relationship between the time and the preceding-stage amplifier output potential is line 18-1. The relationship between the time and the BIAS potential of the subsequent-stage circuit is line 18-B. The relationship between the time and the potential between both ends of the filter capacitor is line 18-2. The rapid potential setting mechanism 275 closes a switch that shortens the time constant of the analog filter 270 in synchronization with the return from the pause period. For example, the rapid potential setting mechanism 275 shortens the filter time constant until the output potential of the analog filter 270 converges to the BIAS potential. When the time constant of the analog filter 270 is set to $\frac{1}{10}$, the time until the output potential of the filter converges becomes $\frac{1}{10}$. This sufficiently shortens the setup time of the BIAS potential as compared with the measurement period. In FIG. 13, the time until the potential of the analog filter 270 stabilizes is shorter than the stabilization time in FIG. 11B, and the minute signal amplifiable period is from time t8-2 to time t8-3.

While the switch that shortens the time constant of the analog filter 270 is closed by the rapid potential setting mechanism 275, the electric signal up to a higher frequency passes, but the part is discarded as the electric signal, and there is no problem.

Meanwhile, the rapid potential setting mechanism 275 can also maintain the potentials at both ends of the filter capacitor of the analog filter 270 by providing a cutoff switch at both ends of the filter capacitor of the analog filter 270, performing cutting off with the cutoff switch before the power supply of the preceding-stage amplifier is turned off, and connecting the cutoff switch after the potential of the preceding-stage amplifier is stabilized.

Figure 14:
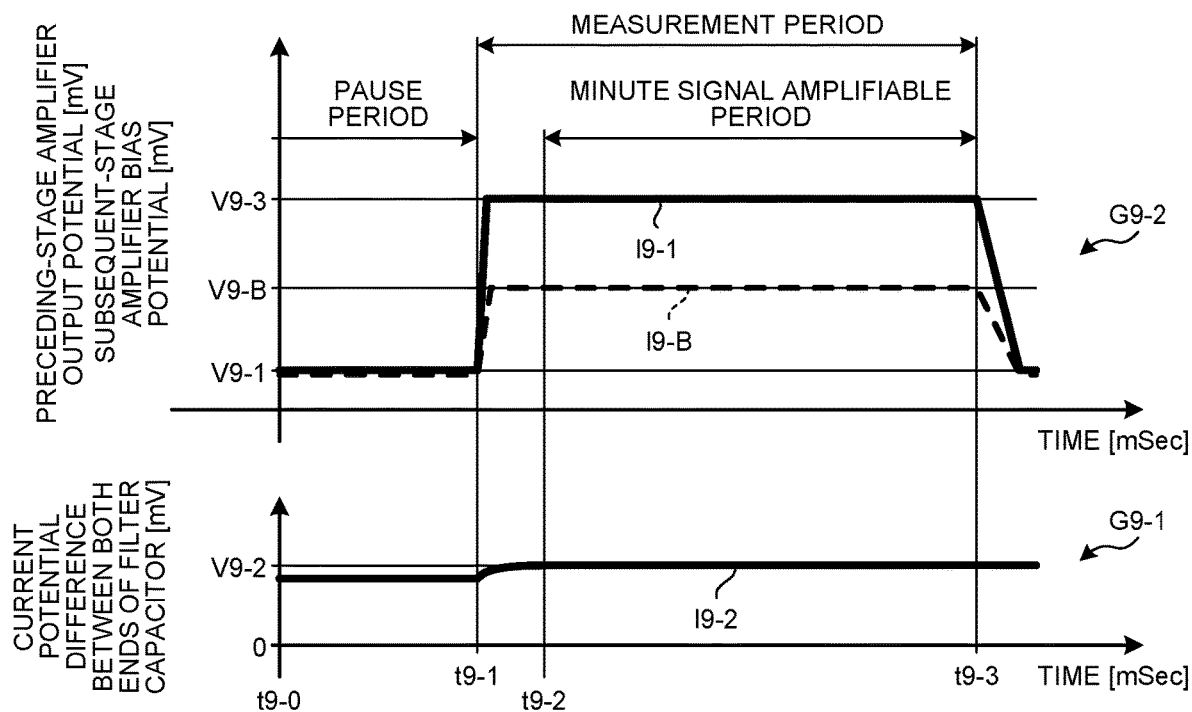
FIG. 14 is a diagram (2) for describing the relationship between the rising of the output of the preceding-stage amplifier and the output of the analog filter.

FIG. 14 is a diagram (2) for describing the relationship between the rising of the output of the preceding-stage amplifier and the output of the analog filter 270. In Graphs G9-1 and G9-2 of FIG. 14, the horizontal axis corresponds to time. In Graph G9-2, the vertical axis corresponds to the output potential of the preceding-stage amplifier (S & H circuit 260). In Graph G9-1, the vertical axis corresponds to the potential difference between both ends of the filter capacitor. The filter capacitor is a capacitor included in the analog filter 270. A period from time t9-0 to t9-1 is a pause period. A period from time t9-1 to t9-3 is a measurement period.

The output signal of the preceding-stage amplifier and the pause potential of a BIAS potential of the subsequent-stage circuit are V9-1. The DC potential at the time of measuring the output signal of the preceding-stage amplifier during the measurement period is V9-3. The BIAS potential at the time of measuring the subsequent-stage circuit is V9-B. The BIAS potential at the time of measuring the subsequent-stage circuit is V9-B. A potential obtained by subtracting the BIAS potential at the time of measuring the subsequent-stage circuit from the DC potential at the time of measuring the output signal of the preceding-stage amplifier is V9-2. The relationship between the time and the preceding-stage amplifier output potential is line 19-1. The relationship between the time and the BIAS potential of the subsequent-stage circuit is line 19-B. The relationship between the time and the potential difference between both ends of the filter capacitor is line 19-2. The rapid potential setting mechanism 275 cuts off the circuit to the filter capacitor in synchronization with the circuit pause period to retain the potential difference between both ends of the filter capacitor. Then, the rapid potential setting mechanism 275 connects the circuit after the pause is released and the output potential of the S & H circuit 260 at the preceding stage and the input BIAS potential of the AC amplifier 280 at the subsequent stage are stabilized. As a result, since the potential difference between both ends of the filter capacitor is kept constant by the same effect as that of the S & H circuit 260, the difference between the output potential of the analog filter 270 and the BAIS potential generated at the time of circuit connection is only about the potential difference of the samples of the electric signal, and the electric signal in the potential range that can be amplified by the AC amplifier 280 is immediately output from the analog filter 270.

In the following description, the rapid potential setting mechanism 275 described with reference to FIG. 13 will be referred to as a "rapid potential setting mechanism 275A" in a case where distinction is particularly made. The rapid potential setting mechanism 275 described with reference to FIG. 14 is referred to as a "rapid potential setting mechanism 275B". The rapid potential setting mechanism 275 having both the characteristics of the rapid potential setting mechanism 275A and the rapid potential setting mechanism 275B is referred to as a "rapid potential setting mechanism 275C".

The description returns to FIG. 12A. The AC amplifier 280 is an amplifier that amplifies the electric signal input from the analog filter 270. The AC amplifier 280 outputs the amplified electric signal to an external device (not illustrated). The external device calculates a blood flow signal based on the Doppler beat on the basis of the electric signal output from the AC amplifier 280. The AC amplifier 280 intermittently operates based on the SW control signal output from the timing control unit 210. The AC amplifier 280 corresponds to the subsequent-stage amplifier when viewed from the analog filter 270.

Here, description of the second intermittent driving described with reference to FIGS. 12A and 12B and effects thereof will be described. The number of samples required to calculate the blood flow signal at a certain time point is determined according to, for example, a window width used in a Fourier transform executed in a subsequent process (not illustrated). The period of continuous measurement required for calculating the blood flow signal can be shortened to, for example, about 10 msec by devising an algorithm.

If the measurement is performed at a frequency of about 30 [sps] or more, information on the pulse wave can be obtained from the blood flow signal. Therefore, if 30 sets of Doppler beat measurement data can be obtained per second, a necessary and sufficient blood flow signal can be acquired. In consideration of these, for example, if the second intermittent driving is performed such that the operation is performed for 10 msec, the series of Doppler beat signals is measured, and the circuit is paused for 20 msec to reduce the power consumption, the circuit can be paused for $\frac{2}{3}$ of the measurement period of 60 seconds, and the power consumption can be reduced to about $\frac{1}{3}$. A state of measurement when such an operation is realized is illustrated in FIG. 12B described above.

On the other hand, in the LDF 10 as the comparative example, when the laser light source 12, the IV amplifier 14, and the analog filter 15 are stopped, the output potential of the IV amplifier 14 converges to, for example, a ground potential or the like, and is greatly different from the output potential in the measurement period. That is, as described with reference to FIG. 11B, after the laser light source 12, the IV amplifier 14, and the analog filter 15 are returned, the output potential of the IV amplifier 14 is quickly returned, but it takes about 11 msec for the output potential of analog filter 15 to converge to the AC amplifiable range, for example, at a cutoff frequency of 150 Hz. That is, even when the second intermittent driving is simply applied to the LDF 10, the waiting time until the measurement becomes possible is 11 msec, and the waiting time becomes too long with respect to 10 ms which is the measurement period length of a series of Doppler beat signals necessary for calculating the blood flow signal.

When the Doppler beat can be instantaneously measured, the operation is performed for 10 msec to obtain a pause period of 20 msec. However, in a case where the measurement is performed after waiting for 11 msec convergence, the operation is performed for 21 msec, and thus the pause period can be obtained only for 9 msec. In addition, in a case where the cutoff frequency is set to be lower, a pause period cannot be obtained, and continuous operation is required.

<<4.2. Configuration of Rapid Potential Setting Mechanism According to Second Embodiment>>

Figure 15:
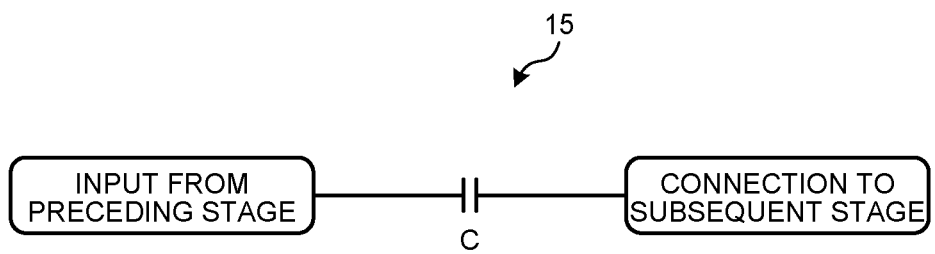
FIG. 15 is a diagram illustrating a basic configuration of an analog filter as a comparative example.

Before describing the configuration of the rapid potential setting mechanism according to the second embodiment, a basic structure of the analog filter 15 of an LDF as a comparative example will be described. FIG. 15 is a diagram illustrating a basic configuration of an analog filter as a comparative example. The analog filter 15 corresponds to capacitor C. The analog filter 15 receives an input of an electric signal from the IV amplifier 14 at the preceding stage. The analog filter outputs an electric signal obtained by cutting off the DC component to the AC amplifier 16 at the subsequent stage.

Hereinafter, various basic configurations of the rapid potential setting mechanism according to the second embodiment will be described.

Figure 16:
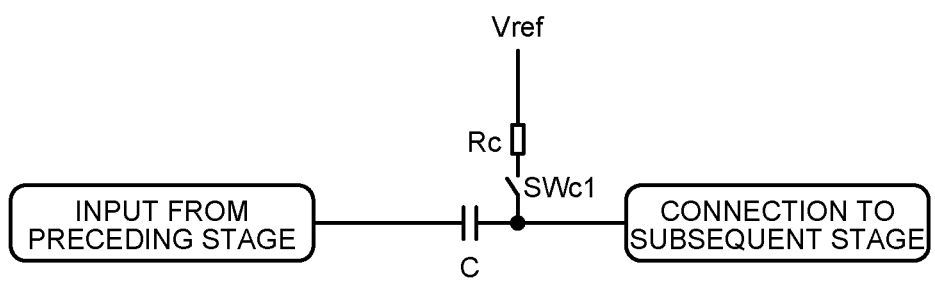
FIG. 16 is a diagram (1) illustrating a basic configuration of a rapid potential setting mechanism according to the second embodiment.

FIG. 16 is a diagram (1) illustrating a basic configuration of the rapid potential setting mechanism according to the second embodiment. In FIG. 16, the analog filter 270 corresponds to capacitor C. Switch SWc1 and resistor Rc correspond to the rapid potential setting mechanism 275A. Vref is a voltage source corresponding to the BIAS potential of the subsequent-stage amplifier. The rapid potential setting mechanism 275A is connected to the potential Vref. The analog filter 270 receives an input of an electric signal from the preceding-stage amplifier. The analog filter 270 outputs the electric signal obtained by cutting off the DC component to the subsequent-stage amplifier.

In FIG. 16, the rapid potential setting mechanism 275A temporarily decreases the time constant (in the transition period until the potential stabilizes) and rapidly stabilizes the potential toward Vref by closing switch SWc1 in synchronization with the return from the pause on the basis of the SW control signal output from the timing control unit 210.

Figure 17:
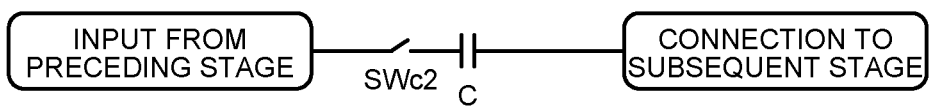
FIG. 17 is a diagram (2) illustrating a basic configuration of the rapid potential setting mechanism according to the second embodiment.

FIG. 17 is a diagram (2) illustrating a basic configuration of the rapid potential setting mechanism according to the second embodiment. In FIG. 17, the analog filter 270 corresponds to capacitor C. Switch SWc2 corresponds to the rapid potential setting mechanism 275B. The analog filter 270 receives an input of an electric signal from the preceding-stage amplifier. The analog filter 270 outputs the electric signal obtained by cutting off the DC component to the subsequent-stage amplifier.

In FIG. 17, the rapid potential setting mechanism 275B turns off switch SWc2 in synchronization with the pause periods of the preceding-stage amplifier and the subsequent-stage amplifier on the basis of the SW control signal output from the timing control unit 210, and retains the accumulated charge of capacitor C. Then, the rapid potential setting mechanism 275B turns on switch SWc2 after the pause is released and the potentials of the preceding-stage amplifier and the subsequent-stage amplifier are stabilized.

Figure 18:
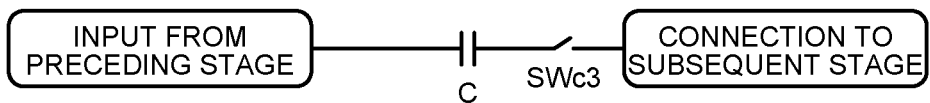
FIG. 18 is a diagram (3) illustrating a basic configuration of the rapid potential setting mechanism according to the second embodiment.

FIG. 18 is a diagram (3) illustrating a basic configuration of the rapid potential setting mechanism according to the second embodiment. In FIG. 18, the analog filter 270 corresponds to capacitor C. Switch SWc3 corresponds to the rapid potential setting mechanism 275B. The analog filter 270 receives an input of an electric signal from the preceding-stage amplifier. The analog filter 270 outputs the electric signal obtained by cutting off the DC component to the subsequent-stage amplifier.

In FIG. 18, the rapid potential setting mechanism 275B turns off switch SWc3 in synchronization with the pause periods of the preceding-stage amplifier and the subsequent-stage amplifier on the basis of the SW control signal output from the timing control unit 210, and retains the accumulated charge of capacitor C. Then, the rapid potential setting mechanism 275B turns on switch SWc3 after the pause is released and the potentials of the preceding-stage amplifier and the subsequent-stage amplifier are stabilized.

Figure 19:
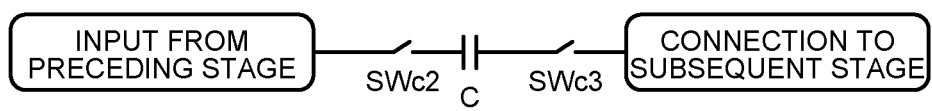
FIG. 19 is a diagram (4) illustrating a basic configuration of the rapid potential setting mechanism according to the second embodiment.

FIG. 19 is a diagram (4) illustrating a basic configuration of the rapid potential setting mechanism according to the second embodiment. In FIG. 19, the analog filter 270 corresponds to capacitor C. Switch SWc2 and switch SWc3 correspond to the rapid potential setting mechanism 275B. The analog filter 270 receives an input of an electric signal from the preceding-stage amplifier. The analog filter 270 outputs the electric signal obtained by cutting off the DC component to the subsequent-stage amplifier.

In FIG. 19, the rapid potential setting mechanism 275B turns off switch SWc2 and switch SWc3 in synchronization with the pause periods of the preceding-stage amplifier and the subsequent-stage amplifier on the basis of the SW control signal output from the timing control unit 210 and retains the accumulated charge of capacitor C. Then, the rapid potential setting mechanism 275B turns on switch SWc3 and switch SWc3 after the pause is released and the potentials of the preceding-stage amplifier and the subsequent-stage amplifier are stabilized.

Figure 20:
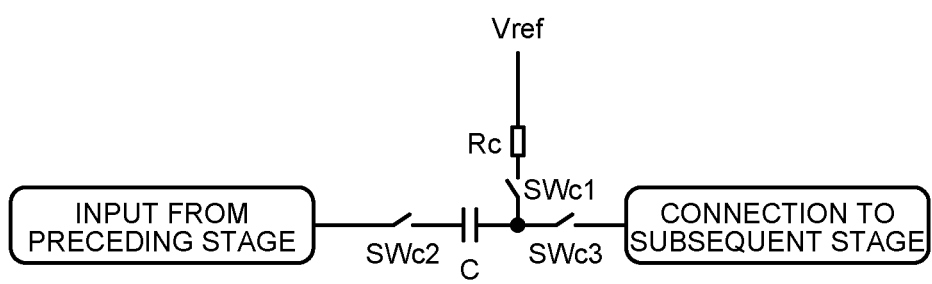
FIG. 20 is a diagram (5) illustrating a basic configuration of the rapid potential setting mechanism according to the second embodiment.

FIG. 20 is a diagram (5) illustrating a basic configuration of the rapid potential setting mechanism according to the second embodiment. In FIG. 20, the analog filter 270 corresponds to capacitor C. Switches SWc1 to SWc3 and resistor Rc correspond to the rapid potential setting mechanism 275C. The analog filter 270 receives an input of an electric signal from the preceding-stage amplifier. The analog filter 270 outputs the electric signal obtained by cutting off the DC component to the subsequent-stage amplifier.

The rapid potential setting mechanism 275C temporarily decreases the time constant by closing switch SWc1 in synchronization with the return from the pause based on the SW control signal output from the timing control unit 210.

In addition, the rapid potential setting mechanism 275C turns off switch SWc2 and switch SWc3 in synchronization with the pause periods of the preceding-stage amplifier and the subsequent-stage amplifier on the basis of the SW control signal output from the timing control unit 210 and retains the accumulated charge of capacitor C. Then, the rapid potential setting mechanism 275B turns on switch SWc2 and switch SWc3 after the pause is released and the potentials of the preceding-stage amplifier and the subsequent-stage amplifier are stabilized.

Figure 21:
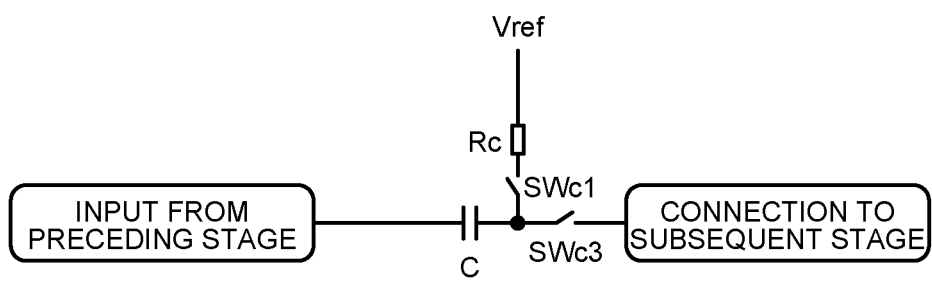
FIG. 21 is a diagram (6) illustrating a basic configuration of the rapid potential setting mechanism according to the second embodiment.

FIG. 21 is a diagram (6) illustrating a basic configuration of the rapid potential setting mechanism according to the second embodiment. In FIG. 21, the analog filter 270 corresponds to capacitor C. Switch SWc1, switch SWc3, and resistor Rc correspond to the rapid potential setting mechanism 275C. The analog filter 270 receives an input of an electric signal from the preceding-stage amplifier. The analog filter 270 outputs the electric signal obtained by cutting off the DC component to the subsequent-stage amplifier.

The rapid potential setting mechanism 275C temporarily decreases the time constant by closing switch SWc1 in synchronization with the return from the pause based on the SW control signal output from the timing control unit 210.

In addition, the rapid potential setting mechanism 275C turns off switch SWc3 in synchronization with the pause period of the subsequent-stage amplifier on the basis of the SW control signal output from the timing control unit 210 and retains the accumulated charge of capacitor C. Then, the rapid potential setting mechanism 275B turns on switch SWc3 after the pause is released and the potential of the subsequent-stage amplifier is stabilized.

Figure 22:
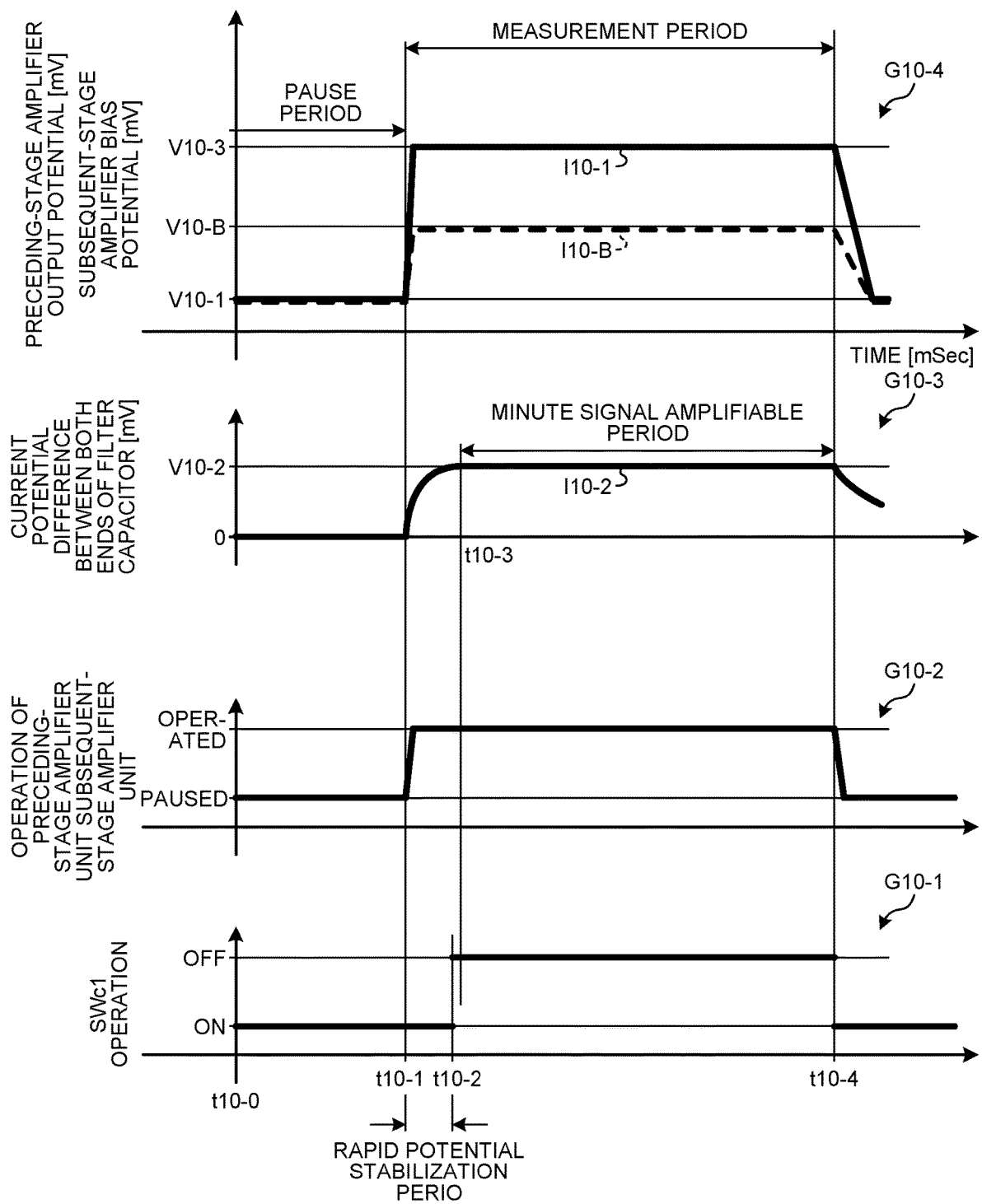
FIG. 22 is a diagram for describing a change in output potential according to the basic configuration of the rapid potential setting mechanism described with reference to FIG. 16.

FIG. 22 is a diagram for describing a change in output potential according to the basic configuration of the rapid potential setting mechanism described with reference to FIG. 16. Graph G10-1 is a graph illustrating opening/closing timing of switch SWc1. The horizontal axis of Graph G10-1 corresponds to time. The vertical axis of Graph G10-1 corresponds to the operation of switch SWc1, and is on or off. For example, switch SWc1 is in a state of "ON" between times t10-0 and t10-2. Switch SWc1 is in a state of "OFF" between times t10-2 and t10-4. Switch SWc1 is in a state of "OFF" for a certain period from time t10-4. A period from time t10-1 to time t10-2 is a rapid potential stabilization period.

Graph G10-2 is a graph illustrating the timing of the intermittent operation of the preceding-stage amplifier (S & H circuit 260) and the subsequent-stage circuit (AC amplifier 280). The horizontal axis of Graph G10-2 corresponds to time. The vertical axis of Graph G10-2 corresponds to the operations of the preceding-stage amplifier and the subsequent-stage circuit, and is pause or operation. For example, the preceding-stage amplifier is "paused" between times t10-0 and t10-1. The pre-stage amplifier is "operated" between times t10-1 and t10-4. The preceding-stage amplifier is "paused" for a certain period from time t10-4.

The relationship between the rising of the output of the preceding-stage amplifier and the output of the analog filter will be described with reference to Graphs G10-3 and G10-4. The horizontal axis of Graph G10-3 corresponds to time, and the vertical axis corresponds to the potential difference between both ends of the filter capacitor. The filter capacitor is a capacitor included in the analog filter 270. The horizontal axis of Graph G10-4 corresponds to time, and the vertical axis corresponds to the output potential of the preceding-stage amplifier (S & H circuit 260) and the BIAS potential of the subsequent-stage circuit (AC amplifier 280).

The output terminal potential of the preceding-stage amplifier during the pause period is V10-1. The output DC potential of the preceding-stage amplifier during the measurement period is V10-3. A potential obtained by subtracting the BIAS potential of the subsequent-stage circuit from the output DC potential of the preceding-stage amplifier during the measurement period is V10-2. The relationship between time and the preceding-stage amplifier output potential is a line 110-1. The relationship between time and the potential difference between both ends of the filter capacitor is a line 110-2. A period from time t10-3 to time t10-4 is a minute signal amplification period.

Figure 23:
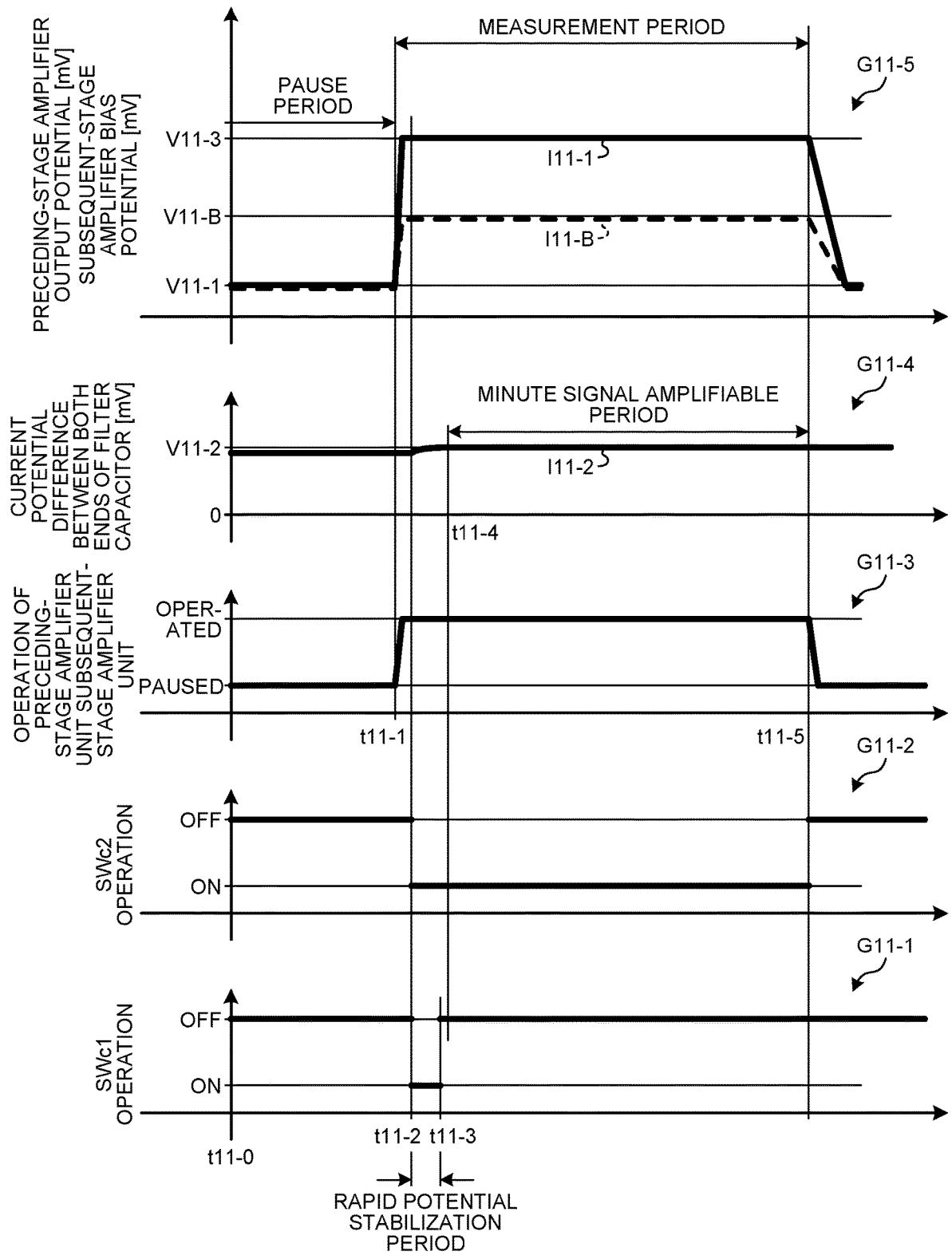
FIG. 23 is a diagram for describing a change in output potential according to a basic configuration in which the rapid potential setting mechanism of FIG. 16 and the rapid potential setting mechanism of FIG. 17 are combined.

FIG. 23 is a diagram for describing a change in output potential according to a basic configuration in which the rapid potential setting mechanism of FIG. 16 and the rapid potential setting mechanism of FIG. 17 are combined. Graph G11-1 is a graph illustrating opening/closing timing of switch SWc1. The horizontal axis of Graph G11-1 corresponds to time. The vertical axis of Graph G11-1 corresponds to the operation of switch SWc1, and is on or off. For example, switch SWc1 is in a state of "OFF" between times t11-0 and t11-2. Switch SWc1 is in a state of "ON" between times t11-2 and t11-3. Switch SWc1 is in a state of "OFF" for a certain period from time t11-3. A period from time t11-2 to time t11-3 is a rapid potential stabilization period.

Graph G11-2 is a graph illustrating opening/closing timing of switch SWc2. The horizontal axis of Graph G11-2 corresponds to time. The vertical axis of Graph G11-2 corresponds to the operation of switch SWc2, and is on or off. For example, switch SWc2 is in a state of "OFF" between times t11-0 and t11-2. Switch SWc2 is in a state of "ON" between times t11-2 and t11-5. Switch SWc2 is in a state of "OFF" for a certain period from time t11-5.

Graph G11-3 is a graph illustrating the timing of the intermittent operation of the preceding-stage amplifier (QV amplifier 250) and the subsequent-stage amplifier (AC amplifier 280). The horizontal axis of Graph G11-3 corresponds to time. The vertical axis of Graph G11-3 corresponds to the operations of the preceding-stage amplifier and the subsequent-stage amplifier, and is pause or operation. For example, the preceding-stage amplifier and the subsequent-stage amplifier are "paused" between times t11-0 and t11-1. The pre-stage amplifier and the post-stage amplifier are "operated" between times t11-1 and t11-5. The preceding-stage amplifier and the subsequent-stage amplifier are "paused" for a certain period from time t11-5.

The relationship between the rising of the output of the preceding-stage amplifier and the output of the analog filter 270 will be described with reference to Graphs G11-4 and G11-5. The horizontal axis of Graph G11-4 corresponds to time, and the vertical axis corresponds to the potential difference between both ends of the filter capacitor. The horizontal axis of Graph G11-5 corresponds to time, and the vertical axis corresponds to the output potential of the preceding-stage amplifier (S & H circuit 260) and the BIAS potential of the subsequent-stage circuit (AC amplifier 280). A period from time t11-0 to t11-1 is a pause period. A period from time t11-1 to time t11-5 is a measurement period of the preceding stage (operation period of the QV amplifier 250). The BIAS potential of the subsequent-stage circuit during the measurement period is V11-B.

The pause potential of the preceding-stage amplifier is V11-1. The DC potential of the preceding-stage amplifier is V11-3. A potential obtained by subtracting the BIAS potential from the DC potential is V11-2. The relationship between time and the preceding-stage amplifier output potential is a line 111-1. The relationship between time and the potential difference between both ends of the filter capacitor is a line 111-2. A period from time t11-4 to time t11-5 is a minute signal amplification period.

Figure 24:
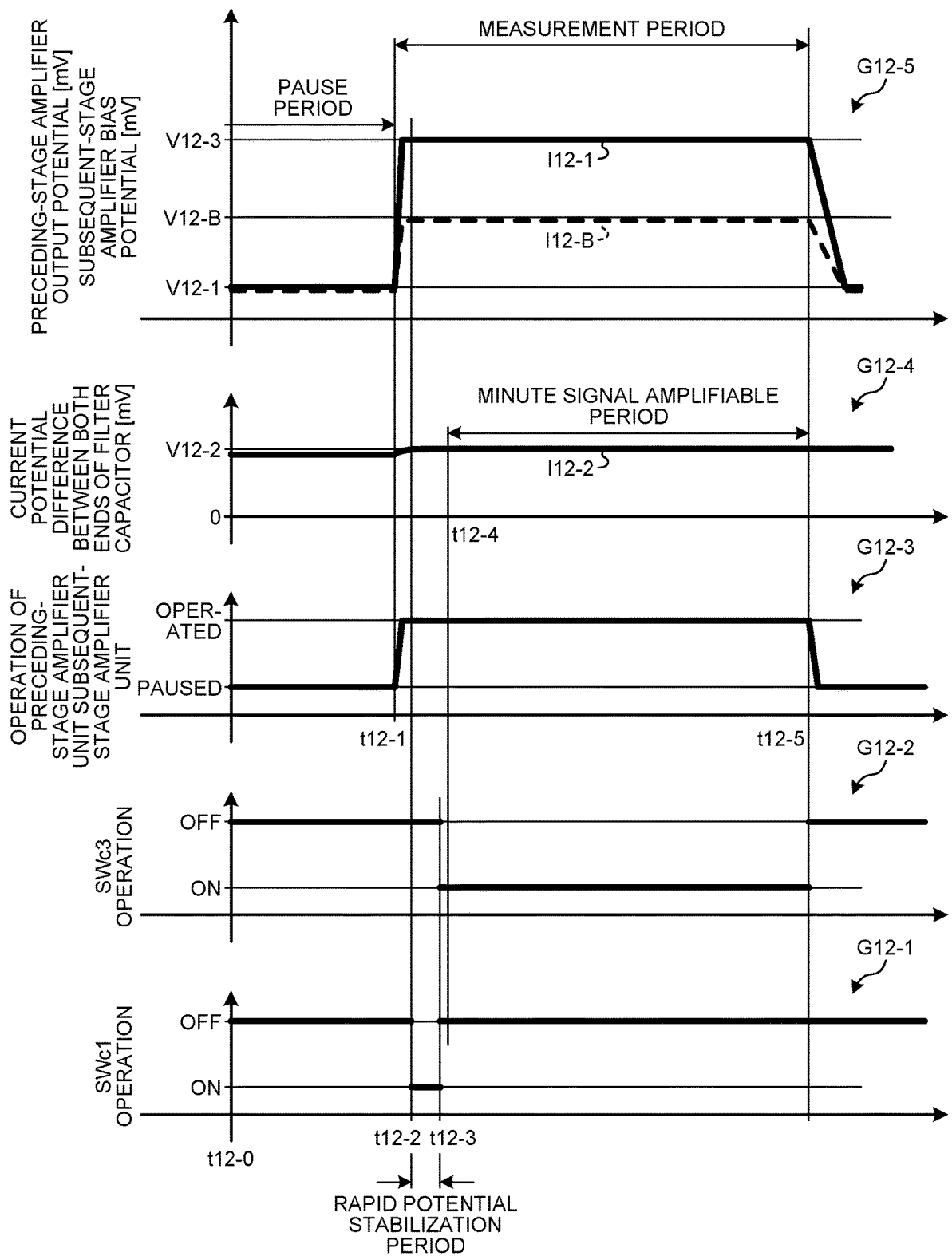
FIG. 24 is a diagram for describing a change in output potential according to the basic configuration of the rapid potential setting mechanism described with reference to FIG. 21.

FIG. 24 is a diagram for describing a change in output potential according to the basic configuration of the rapid potential setting mechanism described with reference to FIG. 21. Graph G12-1 is a graph illustrating opening/closing timing of switch SWc1. The horizontal axis of Graph G12-1 corresponds to time. The vertical axis of Graph G12-1 corresponds to the operation of switch SWc1, and is on or off. For example, switch SWc1 is in a state of "OFF" between times t12-0 and t12-2. Switch SWc1 is in a state of "ON" between times t12-2 and t12-3. Switch SWc1 is in a state of "OFF" for a certain period from time t12-3. A period from time t12-2 to time t12-3 is a rapid potential stabilization period.

Graph G12-2 is a graph illustrating opening/closing timing of switch SWc3. The horizontal axis of Graph G12-2 corresponds to time. The vertical axis of Graph G12-2 corresponds to the operation of switch SWc3, and is on or off. For example, switch SWc3 is in a state of "OFF" between times t12-0 and t12-3. Switch SWc3 is in a state of "ON" between times t12-3 and t12-5. Switch SWc3 is in a state of "OFF" for a certain period from time t11-5.

Graph G12-3 is a graph illustrating the timing of the intermittent operation of the preceding-stage amplifier (QV amplifier 250) and the subsequent-stage amplifier (AC amplifier 280). The horizontal axis of Graph G12-3 corresponds to time. The vertical axis of Graph G12-3 corresponds to the operations of the preceding-stage amplifier and the subsequent-stage amplifier, and is pause or operation. For example, the preceding-stage amplifier and the subsequent-stage amplifier are "paused" between times t12-0 and t12-1. The pre-stage amplifier and the post-stage amplifier are "operated" between times t12-1 and t12-5. The preceding-stage amplifier and the subsequent-stage amplifier are "paused" for a certain period from time t12-5.

The relationship between the rising of the output of the preceding-stage amplifier and the output of the analog filter 270 will be described with reference to Graphs G12-4 and G12-5. The horizontal axis of Graph G12-4 corresponds to time, and the vertical axis corresponds to the potential difference between both ends of the filter capacitor. The horizontal axis of Graph G12-5 corresponds to time, and the vertical axis corresponds to the output potential of the preceding-stage amplifier (S & H circuit 260) and the BIAS potential of the subsequent-stage circuit (AC amplifier 280). A period from time t12-0 to t12-1 is a pause period. A period from time t12-1 to time t12-5 is a measurement period of the preceding stage (operation period of the QV amplifier 250). The BIAS potential of the subsequent-stage circuit during the measurement period is V12-B.

The pause potential of the preceding-stage amplifier is V12-1. The DC potential of the preceding-stage amplifier is V12-3. A potential obtained by subtracting the BIAS potential from the DC potential is V12-2. The relationship between time and the preceding-stage amplifier output potential is a line 112-1. The relationship between time and the potential difference between both ends of the filter capacitor is a line 112-2. A period from time t12-4 to time t12-5 is a minute signal amplification period.

Figure 25:
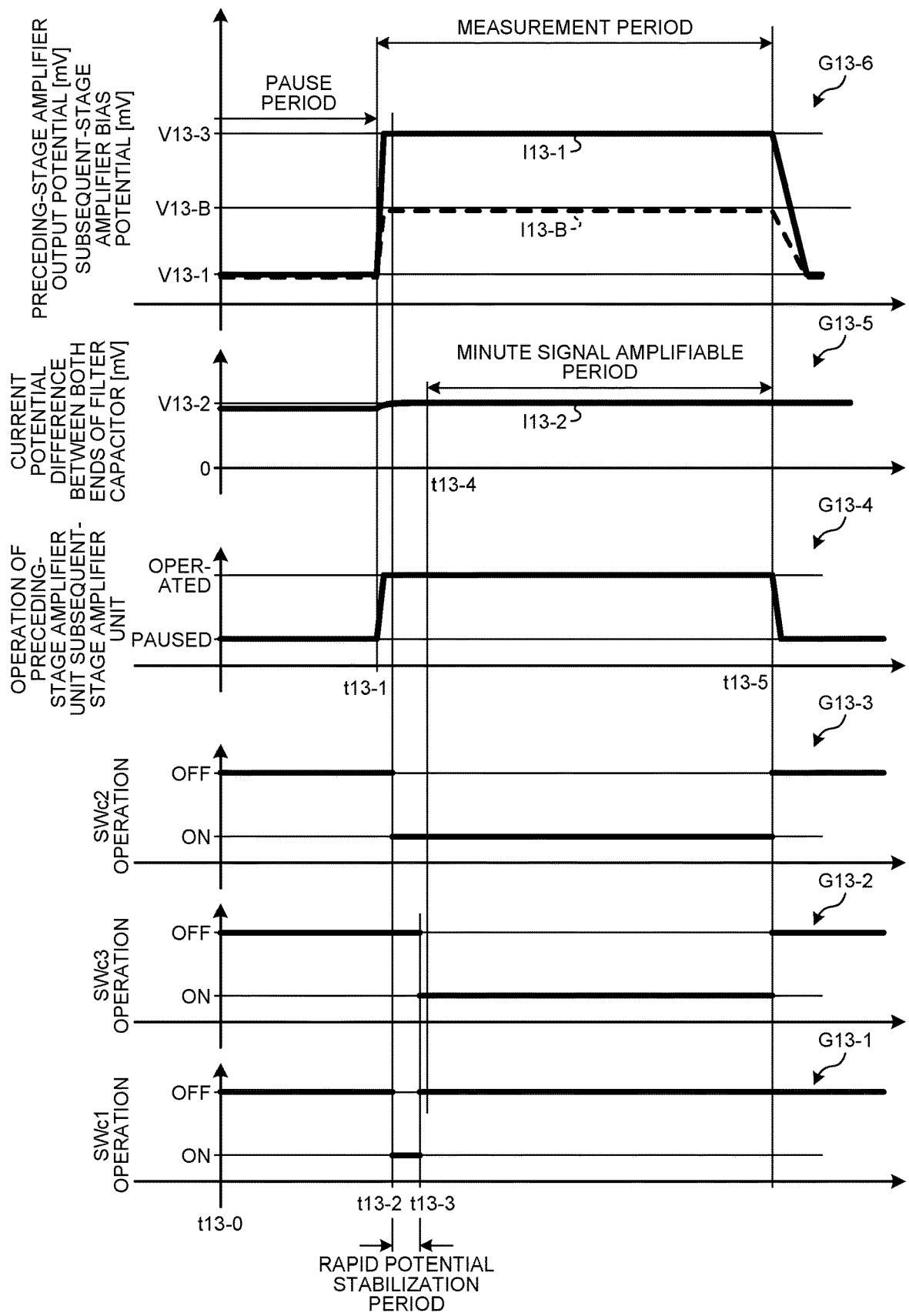
FIG. 25 is a diagram for describing a change in output potential according to the basic configuration of the rapid potential setting mechanism described with reference to FIG. 20.

FIG. 25 is a diagram for describing a change in output potential according to the basic configuration of the rapid potential setting mechanism described with reference to FIG. 20. Graph G13-1 is a graph illustrating opening/closing timing of switch SWc1. The horizontal axis of Graph G13-1 corresponds to time. The vertical axis of Graph G13-1 corresponds to the operation of switch SWc1, and is on or off. For example, switch SWc1 is in a state of "OFF" between times t13-0 and t13-2. Switch SWc1 is in a state of "ON" between times t13-2 and t13-3. Switch SWc1 is in a state of "OFF" for a certain period from time t13-3. A period from time t13-2 to time t13-3 is a rapid potential stabilization period.

Graph G13-2 is a graph illustrating opening/closing timing of switch SWc3. The horizontal axis of Graph G13-2 corresponds to time. The vertical axis of Graph G13-2 corresponds to the operation of switch SWc3, and is on or off. For example, switch SWc3 is in a state of "OFF" between times t13-0 and t13-3. Switch SWc3 is in a state of "ON" between times t13-3 and t13-5. Switch SWc3 is in a state of "OFF" for a certain period from time t13-5.

Graph G13-3 is a graph illustrating opening/closing timing of switch SWc2. The horizontal axis of Graph G13-3 corresponds to time. The vertical axis of Graph G13-3 corresponds to the operation of switch SWc2, and is on or off. For example, switch SWc2 is in a state of "OFF" between times t13-0 and t13-2. Switch SWc2 is in a state of "ON" between times t13-3 and t13-5. Switch SWc2 is in a state of "OFF" for a certain period from time t13-5.

Graph G13-4 is a graph illustrating the timing of the intermittent operation of the preceding-stage amplifier (QV amplifier 250) and the subsequent-stage amplifier (AC amplifier 280). The horizontal axis of Graph G13-4 corresponds to time. The vertical axis of Graph G13-4 corresponds to the operations of the preceding-stage amplifier and the subsequent-stage amplifier, and is pause or operation. For example, the preceding-stage amplifier and the subsequent-stage amplifier are "paused" between times t13-0 and t13-1. The pre-stage amplifier and the post-stage amplifier are "operated" between times t13-1 and t13-5. The preceding-stage amplifier and the subsequent-stage amplifier are "paused" for a certain period from time t13-5.

The relationship between the rising of the output of the preceding-stage amplifier and the output of the analog filter 270 will be described with reference to Graphs G13-5 and G13-6. The horizontal axis of Graph G12-5 corresponds to time, and the vertical axis corresponds to the potential difference between both ends of the filter capacitor. The horizontal axis of Graph G12-6 corresponds to time, and the vertical axis corresponds to the output potential of the preceding-stage amplifier (S & H circuit 260) and the BIAS potential of the subsequent-stage circuit (AC amplifier 280). A period from time t13-0 to t13-1 is a pause period. A period from time t13-1 to time t13-5 is a measurement period of the preceding stage (operation period of the QV amplifier 250). The BIAS potential of the subsequent-stage circuit during the measurement period is V13-B.

The pause potential of the preceding-stage amplifier is V13-1. The DC potential of the preceding-stage amplifier is V13-3. A potential obtained by subtracting the BIAS potential from the DC potential is V13-2. The relationship between time and the preceding-stage amplifier output potential is a line 113-1. The relationship between time and the potential difference between both ends of the filter capacitor is a line 113-2. A period from time t13-4 to time t13-5 is a minute signal amplification period.

<<4.3. Configuration of Low Cut Filter with Rapid Potential Setting Mechanism and Non-Inverting Amplifier Circuit According to Second Embodiment>>

Figure 26:
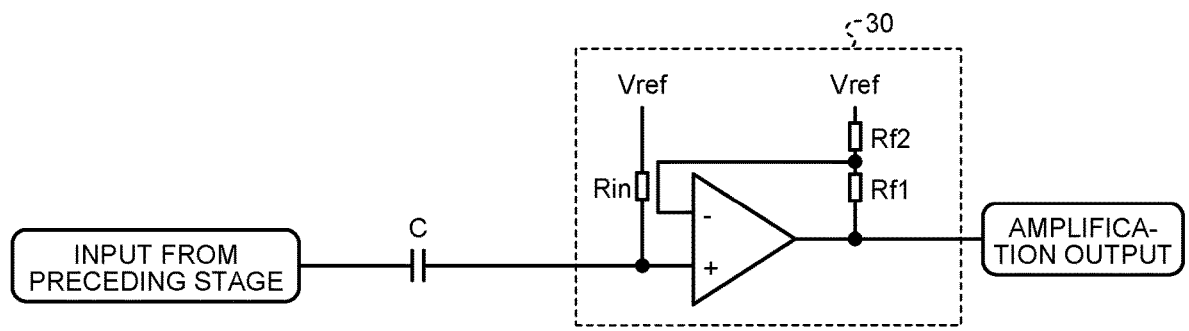
FIG. 26 is a diagram illustrating a configuration including an analog filter and an AC amplifier (non-inverting amplifier circuit) of an LDF as a comparative example.

Before describing a configuration including an analog filter with a rapid potential setting mechanism and a non-inverting amplifier circuit according to the second embodiment, a configuration including an analog filter and an AC amplifier (non-inverting amplifier circuit) of an LDF as a comparative example will be described. FIG. 26 illustrates a configuration including an analog filter and an AC amplifier (non-inverting amplifier circuit) of an LDF as a comparative example. In FIG. 26, capacitor C corresponds to the analog filter 15 (low cut filter), and a non-inverting amplifier circuit 30 corresponds to the AC amplifier 16. The non-inverting amplifier circuit 30 has resistors Rin, Rf1, and Rf2 and is connected to Vref. Although resistor Rin is included in the non-inverting amplifier circuit 30 as an input resistor that applies a BIAS potential to the input end of the non-inverting amplifier circuit 30, resistor Rin constitutes an analog low-cut filter integrated with capacitor C, and is also a part of the analog filter 15.

The analog filter 15 receives an input of an electric signal from the IV amplifier 14 at the preceding stage and accumulates charges in capacitor C. The analog filter 15 outputs the electric signal obtained by cutting off the DC component to the non-inverting amplifier circuit 30 at the subsequent stage. The non-inverting amplifier circuit 30 outputs the amplified electric signal.

Figure 27:
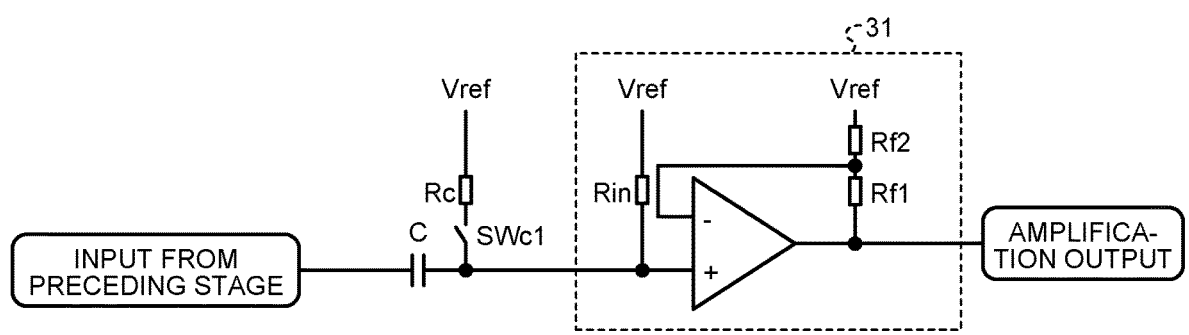
FIG. 27 is a diagram (1) illustrating a configuration including an analog filter with a rapid potential setting mechanism and an AC amplifier (non-inverting amplifier circuit).

FIG. 27 is a diagram (1) illustrating a configuration including an analog filter with a rapid potential setting mechanism and an AC amplifier (non-inverting amplifier circuit). In the example illustrated in FIG. 27, a non-inverting amplifier circuit 31 is connected to the basic configuration of the rapid potential setting mechanism and the analog filter described in FIG. 16. The non-inverting amplifier circuit 31 corresponds to the AC amplifier 280. Although resistor Rin is included in the non-inverting amplifier circuit 31 as an input resistor that applies a BIAS potential to the input end of the non-inverting amplifier circuit 31, resistor Rin constitutes an analog low cut filter integrated with capacitor C, and is also a part of the analog filter 15. Although not described in FIG. 27, it is assumed that a switch for intermittent operation is set in the non-inverting amplifier circuit 31. The non-inverting amplifier circuit 31 outputs the amplified electric signal.

Figure 28:
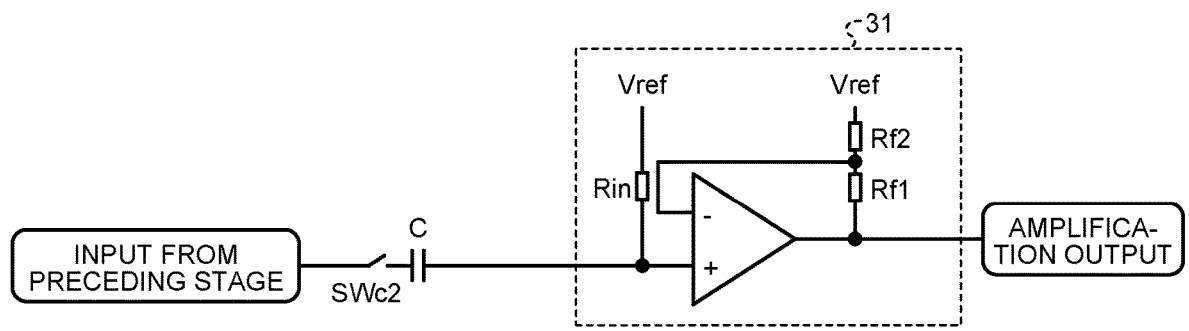
FIG. 28 is a diagram (2) illustrating a configuration including the analog filter with a rapid potential setting mechanism and the AC amplifier (non-inverting amplifier circuit).

FIG. 28 is a diagram (2) illustrating a configuration including the analog filter with a rapid potential setting mechanism and the AC amplifier (non-inverting amplifier circuit). In the example illustrated in FIG. 28, the non-inverting amplifier circuit 31 is connected to the basic configuration of the rapid potential setting mechanism and the analog filter described in FIG. 17. The non-inverting amplifier circuit 31 corresponds to the AC amplifier 280. Although resistor Rin is included in the non-inverting amplifier circuit 31 as an input resistor that applies a BIAS potential to the input end of the non-inverting amplifier circuit 31, resistor Rin constitutes an analog low cut filter integrated with capacitor C, and is also a part of the analog filter 15. Although not described in FIG. 28, it is assumed that a switch for intermittent operation is set in the non-inverting amplifier circuit 31. The non-inverting amplifier circuit 31 outputs the amplified electric signal.

Figure 29:
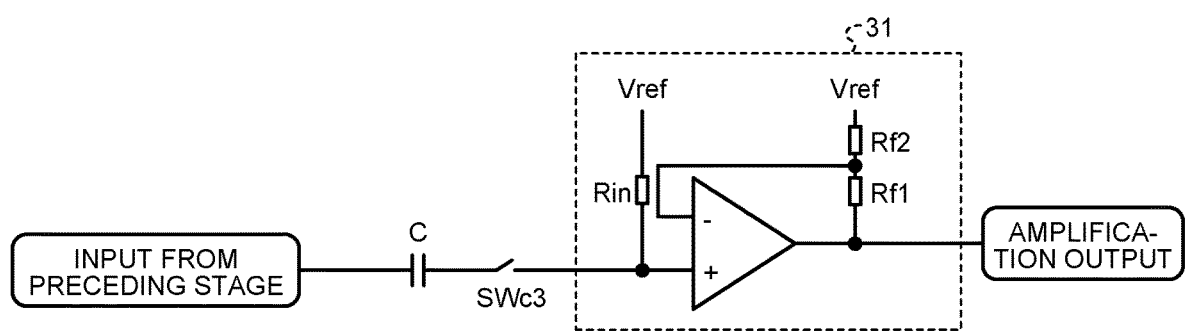
FIG. 29 is a diagram (3) illustrating a configuration including the analog filter with a rapid potential setting mechanism and the AC amplifier (non-inverting amplifier circuit).

FIG. 29 is a diagram (3) illustrating a configuration including the analog filter with a rapid potential setting mechanism and the AC amplifier (non-inverting amplifier circuit). In the example illustrated in FIG. 29, the non-inverting amplifier circuit 31 is connected to the basic configuration of the rapid potential setting mechanism and the analog filter described in FIG. 18. The non-inverting amplifier circuit 31 corresponds to the AC amplifier 280. Although resistor Rin is included in the non-inverting amplifier circuit 31 as an input resistor that applies a BIAS potential to the input end of the non-inverting amplifier circuit 31, resistor Rin constitutes an analog low cut filter integrated with capacitor C, and is also a part of the analog filter 15. Although not described in FIG. 29, it is assumed that a switch for intermittent operation is set in the non-inverting amplifier circuit 31. The non-inverting amplifier circuit 31 outputs the amplified electric signal.

Figure 30:
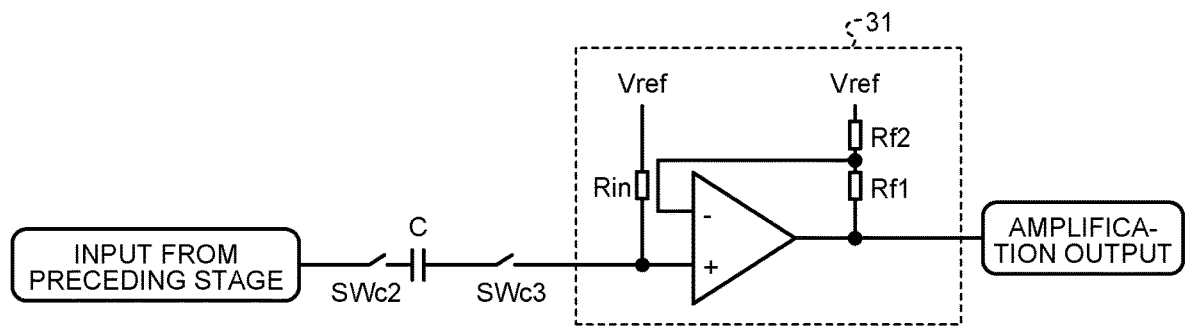
FIG. 30 is a diagram (4) illustrating a configuration including the analog filter with a rapid potential setting mechanism and the AC amplifier (non-inverting amplifier circuit).

FIG. 30 is a diagram (4) illustrating a configuration including the analog filter with a rapid potential setting mechanism and the AC amplifier (non-inverting amplifier circuit). In the example illustrated in FIG. 30, the non-inverting amplifier circuit 31 is connected to the basic configuration of the rapid potential setting mechanism and the analog filter described in FIG. 19. The non-inverting amplifier circuit 31 corresponds to the AC amplifier 280. Although resistor Rin is included in the non-inverting amplifier circuit 31 as an input resistor that applies a BIAS potential to the input end of the non-inverting amplifier circuit 31, resistor Rin constitutes an analog low cut filter integrated with capacitor C, and is also a part of the analog filter 15. Although not described in FIG. 30, it is assumed that a switch for intermittent operation is set in the non-inverting amplifier circuit 31. The non-inverting amplifier circuit 31 outputs the amplified electric signal.

Figure 31:
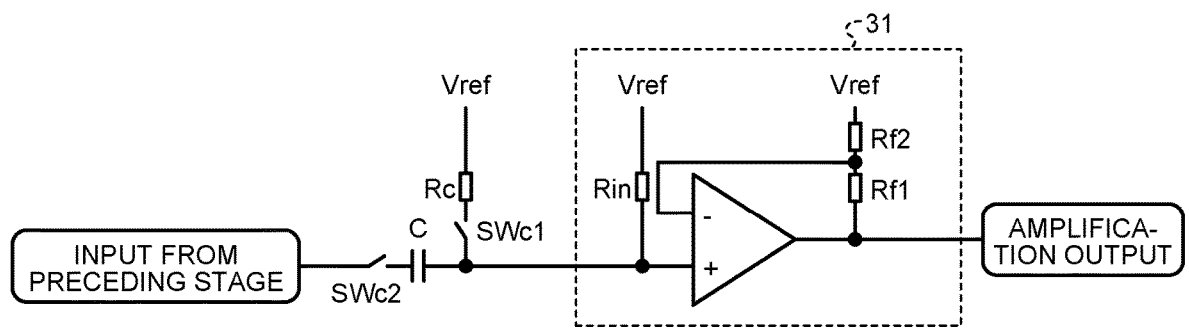
FIG. 31 is a diagram (5) illustrating a configuration including the analog filter with a rapid potential setting mechanism and the AC amplifier (non-inverting amplifier circuit).

FIG. 31 is a diagram (5) illustrating a configuration including the analog filter with a rapid potential setting mechanism and the AC amplifier (non-inverting amplifier circuit). In the example illustrated in FIG. 31, the rapid potential setting mechanism corresponds to switch SWc1, switch SWc2, and resistor Rc. The analog filter corresponds to capacitor C. The non-inverting amplifier circuit 31 is connected to the rapid potential setting mechanism and the analog filter. The non-inverting amplifier circuit 31 corresponds to the AC amplifier 280. Although resistor Rin is included in the non-inverting amplifier circuit 31 as an input resistor that applies a BIAS potential to the input end of the non-inverting amplifier circuit 31, resistor Rin constitutes an analog low cut filter integrated with capacitor C, and is also a part of the analog filter 15. Although not described in FIG. 31, it is assumed that a switch for intermittent operation is set in the non-inverting amplifier circuit 31. The non-inverting amplifier circuit 31 outputs the amplified electric signal.

Figure 32:
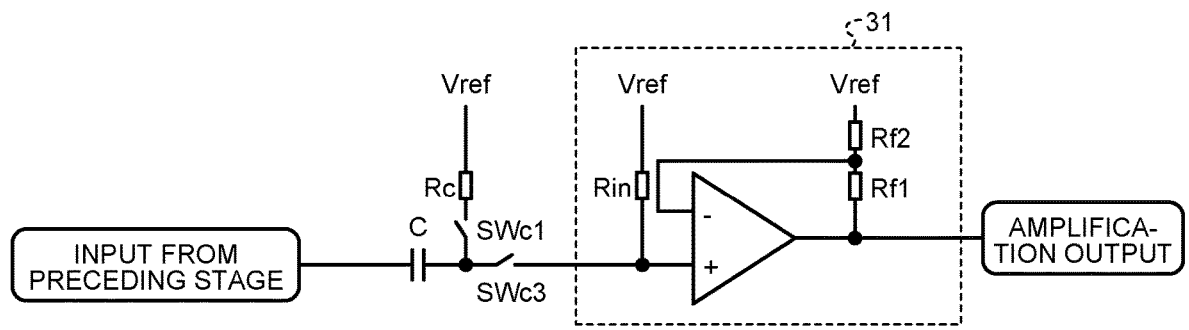
FIG. 32 is a diagram (6) illustrating a configuration including the analog filter with a rapid potential setting mechanism and the AC amplifier (non-inverting amplifier circuit).

FIG. 32 is a diagram (6) illustrating a configuration including the analog filter with a rapid potential setting mechanism and the AC amplifier (non-inverting amplifier circuit). In the example illustrated in FIG. 32, the non-inverting amplifier circuit 31 is connected to the basic configuration of the rapid potential setting mechanism and the analog filter described in FIG. 21. The non-inverting amplifier circuit 31 corresponds to the AC amplifier 280. Although resistor Rin is included in the non-inverting amplifier circuit 31 as an input resistor that applies a BIAS potential to the input end of the non-inverting amplifier circuit 31, resistor Rin constitutes an analog low cut filter integrated with capacitor C, and is also a part of the analog filter 15. Although not described in FIG. 32, it is assumed that a switch for intermittent operation is set in the non-inverting amplifier circuit 31. The non-inverting amplifier circuit 31 outputs the amplified electric signal.

Figure 33:
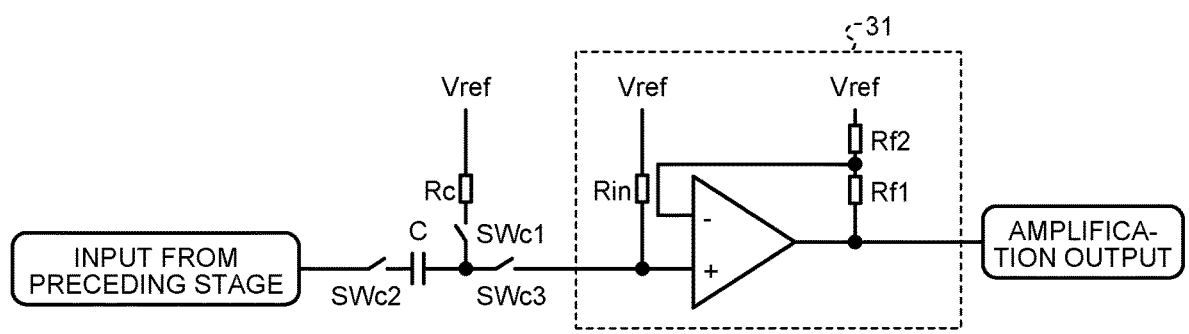
FIG. 33 is a diagram (7) illustrating a configuration including the analog filter with a rapid potential setting mechanism and the AC amplifier (non-inverting amplifier circuit).

FIG. 33 is a diagram (7) illustrating a configuration including the analog filter with a rapid potential setting mechanism and the AC amplifier (non-inverting amplifier circuit). In the example illustrated in FIG. 33, the non-inverting amplifier circuit 31 is connected to the basic configuration of the rapid potential setting mechanism and the analog filter described in FIG. 20. The non-inverting amplifier circuit 31 corresponds to the AC amplifier 280. Although resistor Rin is included in the non-inverting amplifier circuit 31 as an input resistor that applies a BIAS potential to the input end of the non-inverting amplifier circuit 31, resistor Rin constitutes an analog low cut filter integrated with capacitor C, and is also a part of the analog filter 15. Although not described in FIG. 33, it is assumed that a switch for intermittent operation is set in the non-inverting amplifier circuit 31. The non-inverting amplifier circuit 31 outputs the amplified electric signal.

<<4.4. Configuration of Low Cut Filter with Rapid Potential Setting Mechanism and Inverting Amplifier Circuit According to Second Embodiment>>

Figure 34:
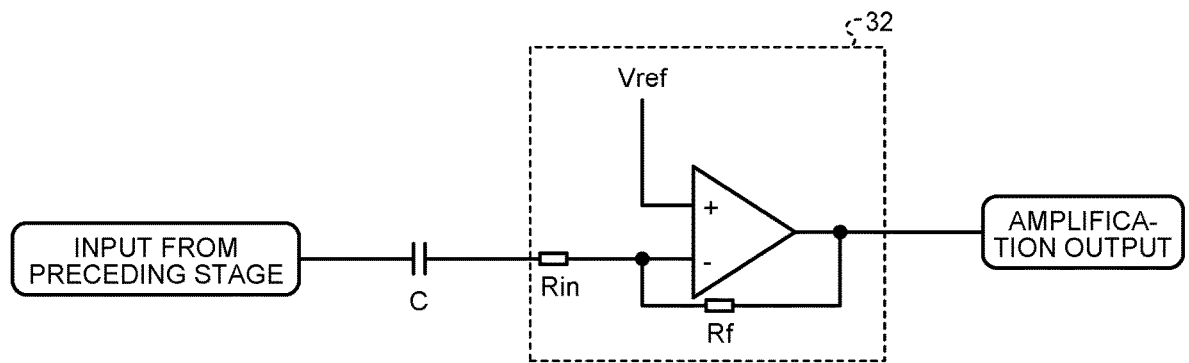
FIG. 34 is a diagram illustrating a configuration including an analog filter and an AC amplifier (inverting amplifier circuit) of an LDF as a comparative example.

In the second embodiment, an inverting amplifier circuit may be used as the AC amplifier 280 instead of the non-inverting amplifier circuit. Before describing a configuration including an analog filter with a rapid potential setting mechanism and an inverting amplifier circuit according to the second embodiment, a configuration including an analog filter and an AC amplifier (non-inverting amplifier circuit) of an LDF as a comparative example will be described. FIG. 34 illustrates configurations of an analog filter and an AC amplifier (inverting amplifier circuit) of an LDF as a comparative example. In FIG. 34, capacitor C corresponds to the analog filter 15 (low cut filter), and an inverting amplifier circuit 32 corresponds to the AC amplifier 16. The inverting amplifier circuit 32 has resistors Rin and Rf2 and is connected to Vref. Although resistor Rin is included in the inverting amplifier circuit 32 as an input resistor that determines the amplification factor of the inverting amplifier circuit 32, resistor Rin constitutes an analog low cut filter integrated with capacitor C, and is also a part of the analog filter 15.

The analog filter 15 receives an input of an electric signal from the IV amplifier 14 at the preceding stage and accumulates charges in capacitor C. The analog filter 15 outputs the electric signal obtained by cutting off the DC component to the inverting amplifier circuit 32 at the subsequent stage. The inverting amplifier circuit 32 outputs the amplified electric signal.

Figure 35:
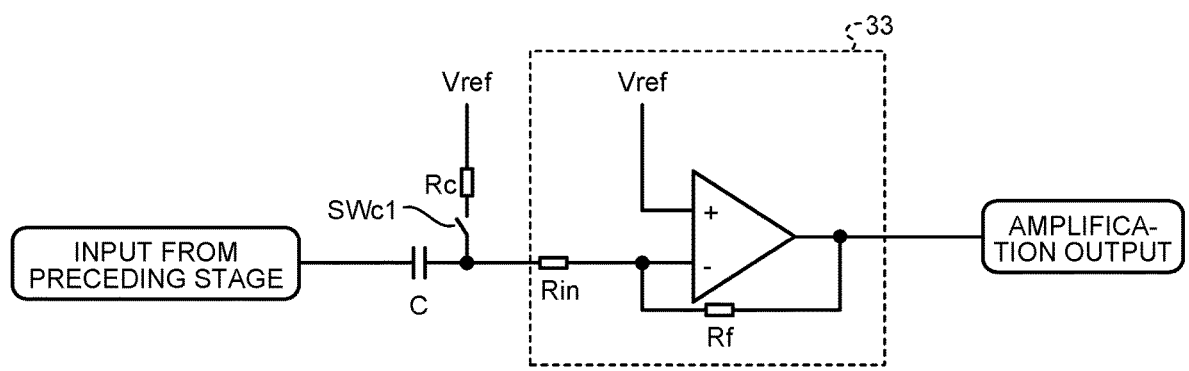
FIG. 35 is a diagram (1) illustrating a configuration including an analog filter with a rapid potential setting mechanism and an AC amplifier (inverting amplifier circuit).

FIG. 35 is a diagram (1) illustrating a configuration including an analog filter with a rapid potential setting mechanism and an AC amplifier (inverting amplifier circuit). In the example illustrated in FIG. 35, an inverting amplifier circuit 33 is connected to the basic configuration of the rapid potential setting mechanism and the analog filter described in FIG. 16. The inverting amplifier circuit 33 corresponds to the AC amplifier 280. Although resistor Rin is included in the inverting amplifier circuit 33 as an input resistor that determines the amplification factor of the inverting amplifier circuit 33, resistor Rin constitutes an analog low cut filter integrated with capacitor C, and is also a part of the analog filter 15. Although not described in FIG. 35, it is assumed that a switch for intermittent operation is set in the inverting amplifier circuit 33. The inverting amplifier circuit 33 outputs the amplified electric signal.

Figure 36:
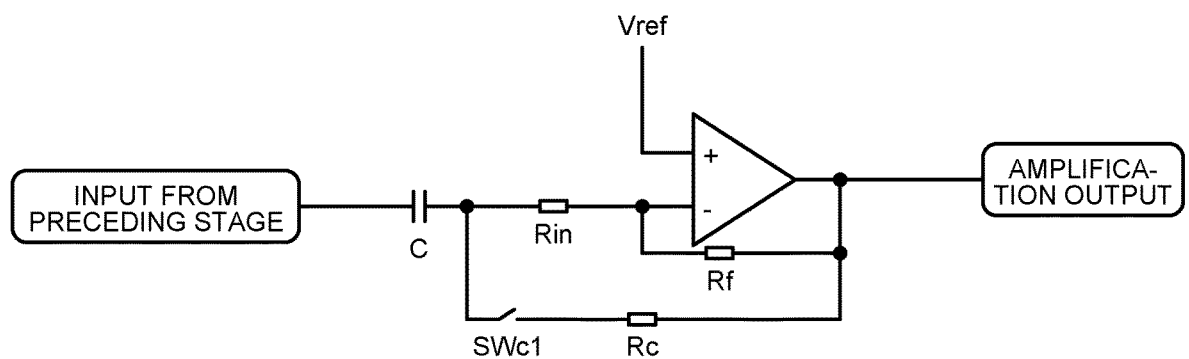
FIG. 36 is a diagram (1) illustrating a configuration in which the analog filter with a rapid potential setting mechanism and the inverting amplifier circuit are coupled.

When the analog filter with a rapid potential setting mechanism described in FIG. 35 and the inverting amplifier circuit are coupled, the configuration illustrated in FIG. 36 can be taken. FIG. 36 is a diagram (1) illustrating a configuration in which the analog filter with a rapid potential setting mechanism and the inverting amplifier circuit are coupled. In the configuration illustrated in FIG. 36, the output offset of the operational amplifier is less likely to adversely affect the rapid potential setting than in the configuration illustrated in FIG. 36.

Figure 37:
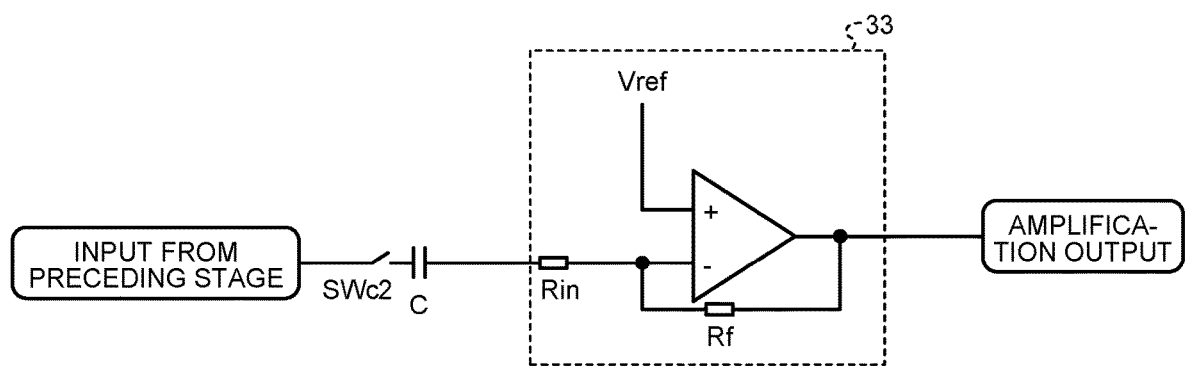
FIG. 37 is a diagram (2) illustrating a configuration including the analog filter with a rapid potential setting mechanism and the AC amplifier (inverting amplifier circuit).

FIG. 37 is a diagram (2) illustrating a configuration including the analog filter with a rapid potential setting mechanism and the AC amplifier (inverting amplifier circuit). In the example illustrated in FIG. 37, the inverting amplifier circuit 33 is connected to the basic configuration of the rapid potential setting mechanism and the analog filter described in FIG. 17. The inverting amplifier circuit 33 corresponds to the AC amplifier 280. Although resistor Rin is included in the inverting amplifier circuit 33 as an input resistor that determines the amplification factor of the inverting amplifier circuit 33, resistor Rin constitutes an analog low cut filter integrated with capacitor C, and is also a part of the analog filter 15. Although not described in FIG. 37, it is assumed that a switch for intermittent operation is set in the inverting amplifier circuit 33. The inverting amplifier circuit 33 outputs the amplified electric signal.

Figure 38:
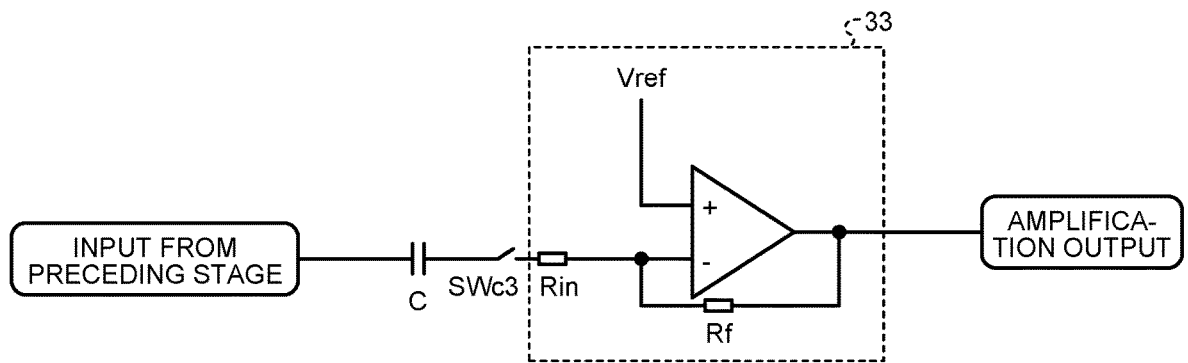
FIG. 38 is a diagram (3) illustrating a configuration including the analog filter with a rapid potential setting mechanism and the AC amplifier (inverting amplifier circuit).

FIG. 38 is a diagram (3) illustrating a configuration including the analog filter with a rapid potential setting mechanism and the AC amplifier (inverting amplifier circuit). In the example illustrated in FIG. 38, the inverting amplifier circuit 33 is connected to the basic configuration of the rapid potential setting mechanism and the analog filter described in FIG. 18. The inverting amplifier circuit 33 corresponds to the AC amplifier 280. Although resistor Rin is included in the inverting amplifier circuit 33 as an input resistor that determines the amplification factor of the inverting amplifier circuit 33, resistor Rin constitutes an analog low cut filter integrated with capacitor C, and is also a part of the analog filter 15. Although not described in FIG. 38, it is assumed that a switch for intermittent operation is set in the inverting amplifier circuit 33. The inverting amplifier circuit 33 outputs the amplified electric signal.

Figure 39:
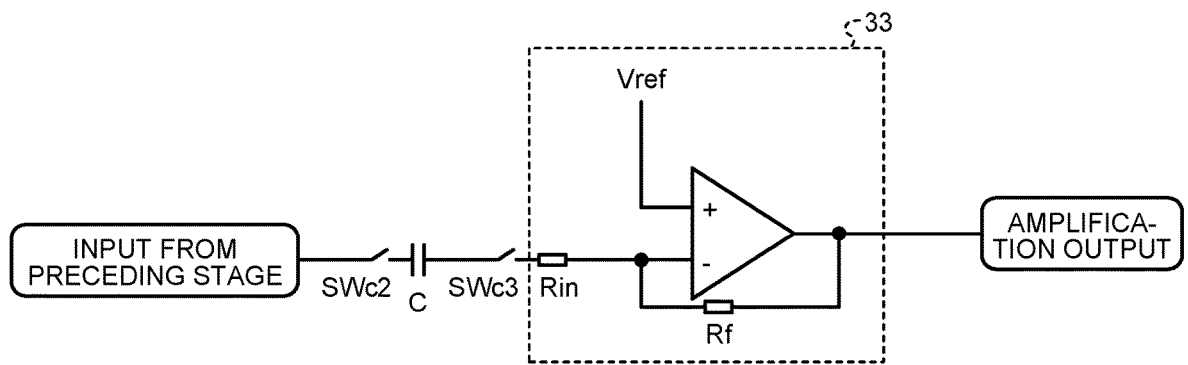
FIG. 39 is a diagram (4) illustrating a configuration including the analog filter with a rapid potential setting mechanism and the AC amplifier (inverting amplifier circuit).

FIG. 39 is a diagram (4) illustrating a configuration including the analog filter with a rapid potential setting mechanism and the AC amplifier (inverting amplifier circuit). In the example illustrated in FIG. 39, the inverting amplifier circuit 33 is connected to the basic configuration of the rapid potential setting mechanism and the analog filter described in FIG. 19. The inverting amplifier circuit 33 corresponds to the AC amplifier 280. Although resistor Rin is included in the inverting amplifier circuit 33 as an input resistor that determines the amplification factor of the inverting amplifier circuit 33, resistor Rin constitutes an analog low cut filter integrated with capacitor C, and is also a part of the analog filter 15. Although not described in FIG. 39, it is assumed that a switch for intermittent operation is set in the inverting amplifier circuit 33. The inverting amplifier circuit 33 outputs the amplified electric signal.

Figure 40:
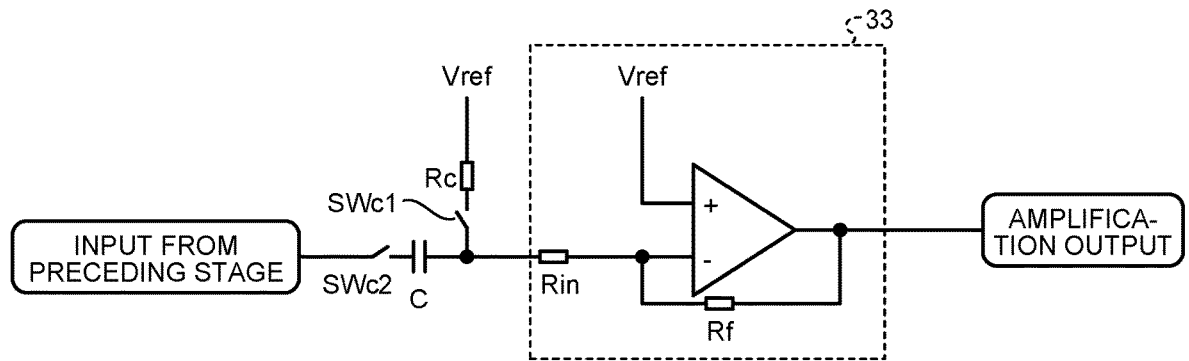
FIG. 40 is a diagram (5) illustrating a configuration including the analog filter with a rapid potential setting mechanism and the AC amplifier (inverting amplifier circuit).

FIG. 40 is a diagram (5) illustrating a configuration including the analog filter with a rapid potential setting mechanism and the AC amplifier (inverting amplifier circuit). In the example illustrated in FIG. 40, the rapid potential setting mechanism corresponds to switch SWc1, switch SWc2, and resistor Rc. The analog filter corresponds to capacitor C. The inverting amplifier circuit 33 is connected to the rapid potential setting mechanism and the analog filter. The inverting amplifier circuit 33 corresponds to the AC amplifier 280. Although resistor Rin is included in the inverting amplifier circuit 33 as an input resistor that determines the amplification factor of the inverting amplifier circuit 33, resistor Rin constitutes an analog low cut filter integrated with capacitor C, and is also a part of the analog filter 15. Although not described in FIG. 40, it is assumed that a switch for intermittent operation is set in the inverting amplifier circuit 33. The inverting amplifier circuit 33 outputs the amplified electric signal.

Figure 41:
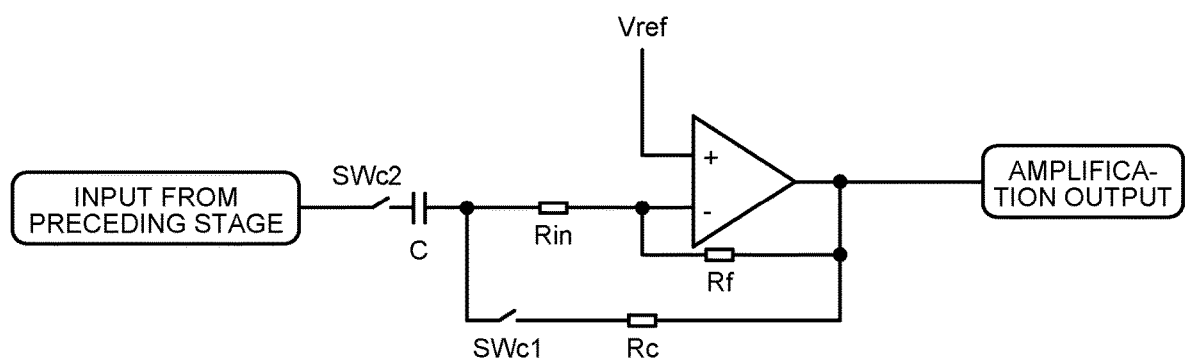
FIG. 41 is a diagram (2) illustrating a configuration in which the analog filter with a rapid potential setting mechanism and the inverting amplifier circuit are coupled.

When the analog filter with a rapid potential setting mechanism and the inverting amplifier circuit described in FIG. 40 are coupled, the configuration illustrated in FIG. 41 is obtained. FIG. 41 is a diagram (2) illustrating a configuration in which the analog filter with a rapid potential setting mechanism and the inverting amplifier circuit are coupled. In the configuration illustrated in FIG. 41, the output offset of the operational amplifier is less likely to adversely affect the rapid potential setting than in the configuration illustrated in FIG. 40.

Figure 42:
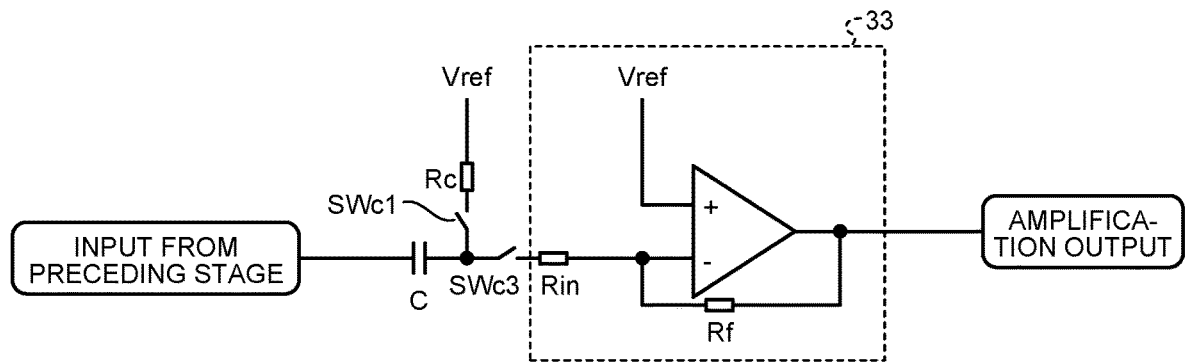
FIG. 42 is a diagram (6) illustrating a configuration including the analog filter with a rapid potential setting mechanism and the AC amplifier (inverting amplifier circuit).

FIG. 42 is a diagram (6) illustrating a configuration including the analog filter with a rapid potential setting mechanism and the AC amplifier (inverting amplifier circuit). In the example illustrated in FIG. 42, the inverting amplifier circuit 33 is connected to the basic configuration of the rapid potential setting mechanism and the analog filter described in FIG. 21. The inverting amplifier circuit 33 corresponds to the AC amplifier 280. Although resistor Rin is included in the inverting amplifier circuit 33 as an input resistor that determines the amplification factor of the inverting amplifier circuit 33, resistor Rin constitutes an analog low cut filter integrated with capacitor C, and is also a part of the analog filter 15. Although not described in FIG. 42, it is assumed that a switch for intermittent operation is set in the inverting amplifier circuit 33. The inverting amplifier circuit 33 outputs the amplified electric signal.

Figure 43:
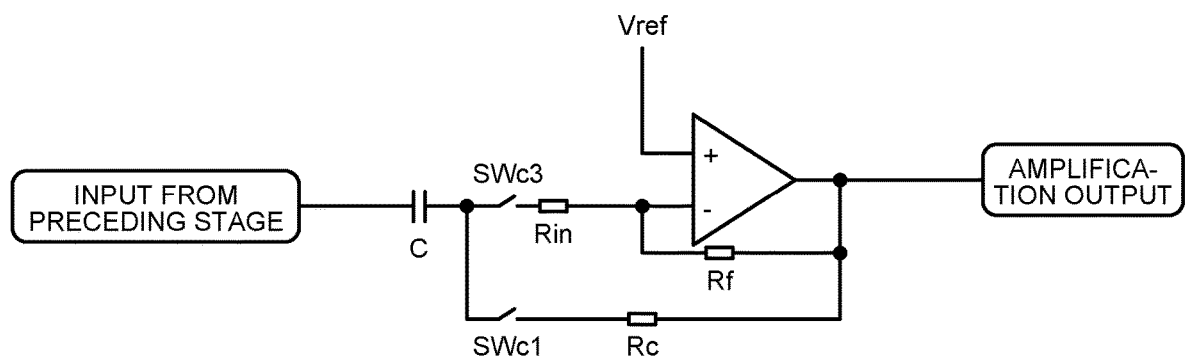
FIG. 43 is a diagram (3) illustrating a configuration in which the analog filter with a rapid potential setting mechanism and the inverting amplifier circuit are coupled.

When the analog filter with a rapid potential setting mechanism and the inverting amplifier circuit described in FIG. 42 are coupled, the configuration illustrated in FIG. 43 is obtained. FIG. 43 is a diagram (3) illustrating a configuration in which the analog filter with a rapid potential setting mechanism and the inverting amplifier circuit are coupled. In the configuration illustrated in FIG. 43, the output offset of the operational amplifier is less likely to adversely affect the rapid potential setting than in the configuration illustrated in FIG. 42.

Figure 44:
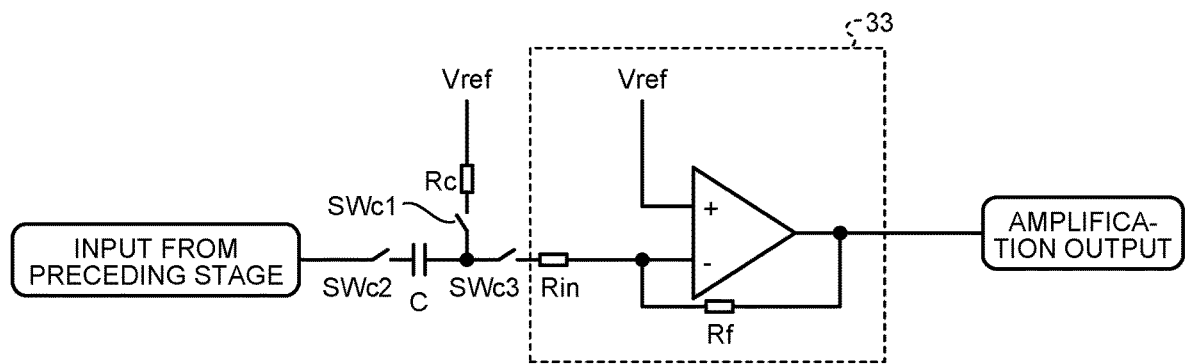
FIG. 44 is a diagram (7) illustrating a configuration including the analog filter with a rapid potential setting mechanism and the AC amplifier (inverting amplifier circuit).

FIG. 44 is a diagram (7) illustrating a configuration including the analog filter with a rapid potential setting mechanism and the AC amplifier (inverting amplifier circuit). In the example illustrated in FIG. 44, the inverting amplifier circuit 33 is connected to the basic configuration of the rapid potential setting mechanism and the analog filter described in FIG. 20. The inverting amplifier circuit 33 corresponds to the AC amplifier 280. Although resistor Rin is included in the inverting amplifier circuit 33 as an input resistor that determines the amplification factor of the inverting amplifier circuit 33, resistor Rin constitutes an analog low cut filter integrated with capacitor C, and is also a part of the analog filter 15. Although not described in FIG. 44, it is assumed that a switch for intermittent operation is set in the inverting amplifier circuit 33. The inverting amplifier circuit 33 outputs the amplified electric signal.

Figure 45:
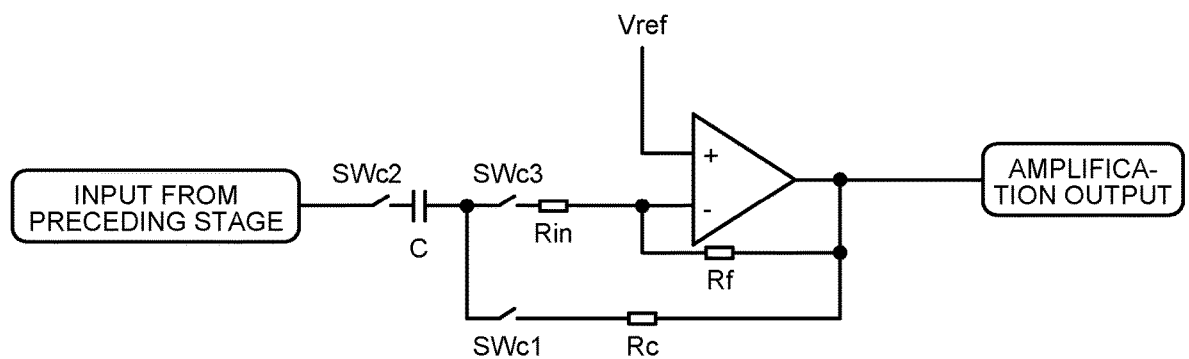
FIG. 45 is a diagram (4) illustrating a configuration in which the analog filter with a rapid potential setting mechanism and the inverting amplifier circuit are coupled.

When the analog filter with a rapid potential setting mechanism and the inverting amplifier circuit described in FIG. 44 are coupled, the configuration illustrated in FIG. 45 is obtained. FIG. 45 is a diagram (4) illustrating a configuration in which the analog filter with a rapid potential setting mechanism and the inverting amplifier circuit are coupled. In the configuration illustrated in FIG. 45, the output offset of the operational amplifier is less likely to adversely affect the rapid potential setting than in the configuration illustrated in FIG. 44.

<<4.5. Open/Close Timing of Each Switch According to Second Embodiment>>

Figure 46:
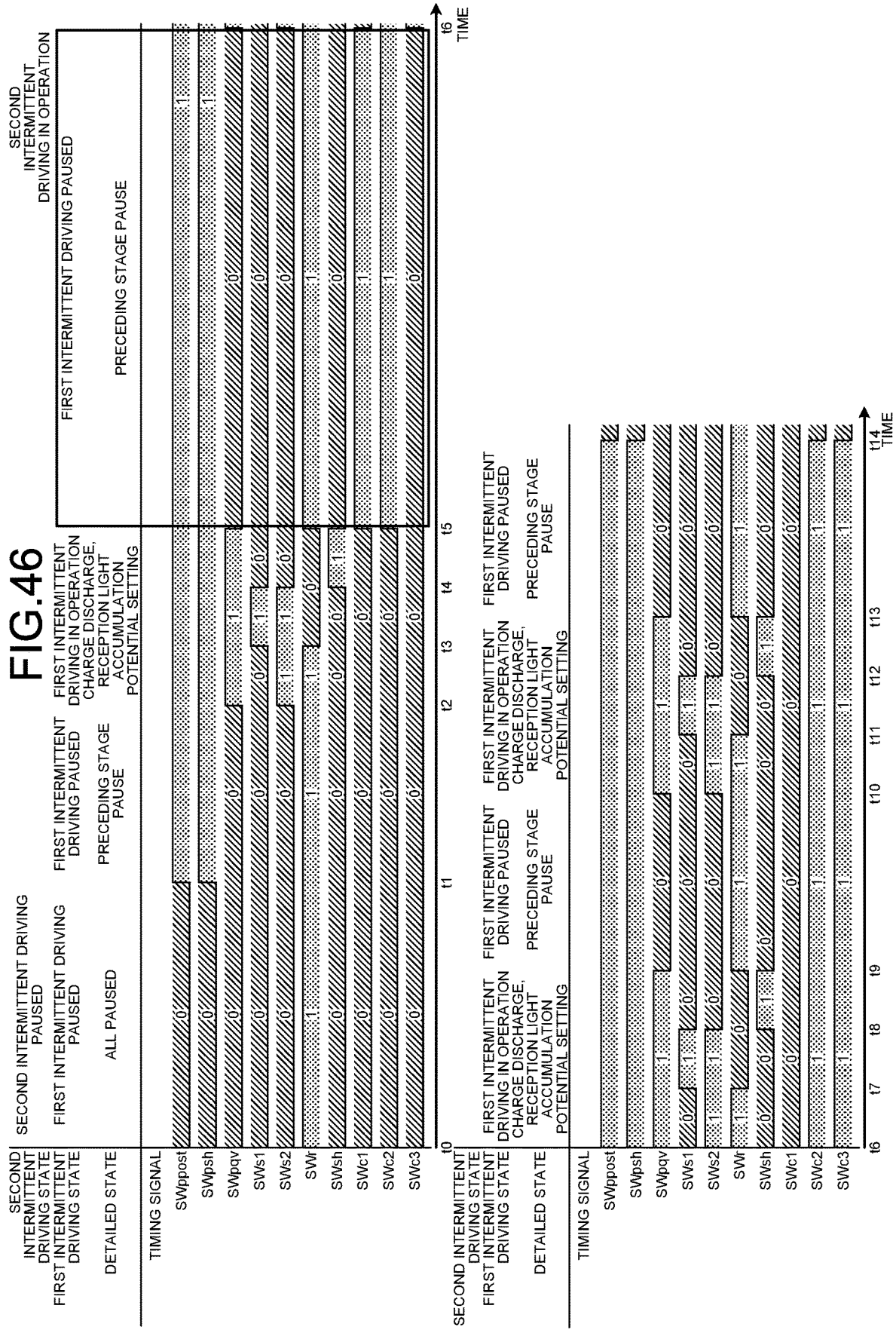
FIG. 46 is a diagram (1) for describing an example of opening/closing timing of each switch according to the second embodiment.

FIG. 46 is a diagram (1) for describing an example of opening/closing timing of each switch according to the second embodiment. In FIG. 46, a section having a value "0" indicates that the switch is closed, and a section having a value "1" indicates that the switch is open. The horizontal axis in FIG. 46 corresponds to time.

The opening/closing timing of switch SWppost will be described. Switch SWppost is a switch that switches between a pause and an operation of the AC amplifier 280. When switch SWppost is in the closed state, the AC amplifier 280 operates, and when switch SWppost is in the open state, the AC amplifier 280 pauses. Switch SWppost is in an open state between times t0 and t1. Switch SWppost is in a closed state between times t1 and t14. Switch SWppost is in an open state after time t14. Although not illustrated, switch SWpost repeats the opening/closing timing illustrated in FIG. 46 to periodically perform measurement after time t14. The opening/closing timing of switch SWppost corresponds to the timing of the "second intermittent driving".

The opening/closing timing of switch SWpsh will be described. Switch SWpsh corresponds to Switch SWpsh illustrated in FIG. 9. Switch SWpsh is in an open state between times t0 and t1. Switch SWpsh is in a closed state between times t1 and t14. Switch SWpsh is in an open state after time t14. Although not illustrated, switch SWpsh repeats the opening/closing timing illustrated in FIG. 46 to periodically perform measurement after time t14. The opening/closing timing of switch SWpsh corresponds to the timing of the "second intermittent driving".

The opening/closing timing of switch SWpqv will be described. Switch SWpqv corresponds to switch SWpqv illustrated in FIG. 9. Switch SWpqv is in an open state between times t0 and t2. Switch Wpqv is in a closed state between times t2 and t5. Switch SWpqv is in an open state between times t5 and t6. Switch SWpqv is in a closed state between times t6 and t9. Switch SWpqv is in an open state between times t9 and t10. Switch SWpqv is in a closed state between times t10 and t13. Switch SWpqv is in an open state between times t13 and t14. Switch SWpqv maintains the open state after time t14. Although not illustrated, switch SWpqv repeats the opening/closing timing illustrated in FIG. 46 to periodically perform measurement after time t14. The opening/closing timing of switch SWpqv corresponds to the timing of the "first intermittent driving".

The opening/closing timing of switch SWs1 will be described. Switch SWs1 corresponds to switch SWs1 illustrated in FIG. 9. Switch SWs1 is in an open state between times t0 and t3. Switch SWs1 is in a closed state between times t3 and t4. Switch SWs1 is in an open state between times t4 and t7. Switch SWs1 is in a closed state between times t7 and t8. Switch SWs1 is in an open state between times t8 and t11. Switch SWs1 is in a closed state between times t11 and t12. Although not illustrated, switch SWs1 becomes in an open state for a while after time t12 and then repeats the opening/closing timing illustrated in FIG. 46.

The opening/closing timing of switch SWs2 will be described. Switch SWs2 corresponds to switch SWs2 illustrated in FIG. 9. Switch SWs2 is in an open state between times t0 and t2. Switch SWs2 is in a closed state between times t2 and t4. Switch SWs2 is in an open state between times t4 and t6. Switch SWs2 is a closed state between times t6 and t8. Switch SWs2 is in an open state between times t8 and t10. Switch SWs2 is in a closed state between times t10 and t12. Switch SWs2 becomes in an open state for a while after time t12 and then repeats the opening/closing timing illustrated in FIG. 46.

The opening/closing timing of switch SWr will be described. Switch SWr corresponds to switch SWr illustrated in FIG. 9. Switch SWr is in a closed state between times t0 and t3. Switch SWr is in an open state between times t3 and t5. Switch SWr is a closed state between times t5 and t7. Switch SWr is in an open state between times t7 and t9. Switch SWr is a closed state between times t9 and t11. Switch SWr is in an open state between times t11 and t13. Switch SWr becomes in a closed state for a while after time t13 and then repeats the opening/closing timing illustrated in FIG. 46.

The opening/closing timing of switch SWsh will be described. Switch SWsh corresponds to switch SWr illustrated in FIG. 9. Switch SWsh is in an open state between times t0 and t4. Switch SWsh is in a closed state between times t4 and t5. Switch SWsh is in an open state between times t5 and t8. Switch SWsh is in a closed state between times t8 and t9. Switch SWsh is in an open state between times t9 and t12. Switch SWsh is in a closed state between times t12 and t13. Switch SWsh becomes in an open state for a while after time t13 and then repeats the opening/closing timing illustrated in FIG. 46.

Next, opening/closing timings of switches SWc1, SWc2, and SWc3 will be described. For example, switches SWc1, SWc2, and SWc3 correspond to switches SWc1, SWc2, and SWc3 illustrated in FIG. 20.

Switch SWc1 is in an open state between times t0 and t5. Switch SWc1 is in a closed state between times t5 and t6. Switch SWc1 becomes in an open state for a while after time t6 and then repeats the opening/closing timing illustrated in FIG. 46.

Switch SWc2 is in an open state between times t0 and t5. Switch SWc2 is in a closed state between times t5 and t14. Switch SWc2 becomes in an open state for a while after time t14 and then repeats the opening/closing timing illustrated in FIG. 46.

Switch SWc3 is in an open state between times t0 and t6. Switch SWc3 is in a closed state between times t6 and t14. Switch SWc3 becomes in an open state for a while after time t14 and then repeats the opening/closing timing illustrated in FIG. 46.

In the example illustrated in FIG. 46, the potential setting can be performed without consuming unnecessary power by extending the pause period before the operation of measuring one sample up to the time required for the rapid potential setting in a period of time t5 to time t6.

Figure 47:
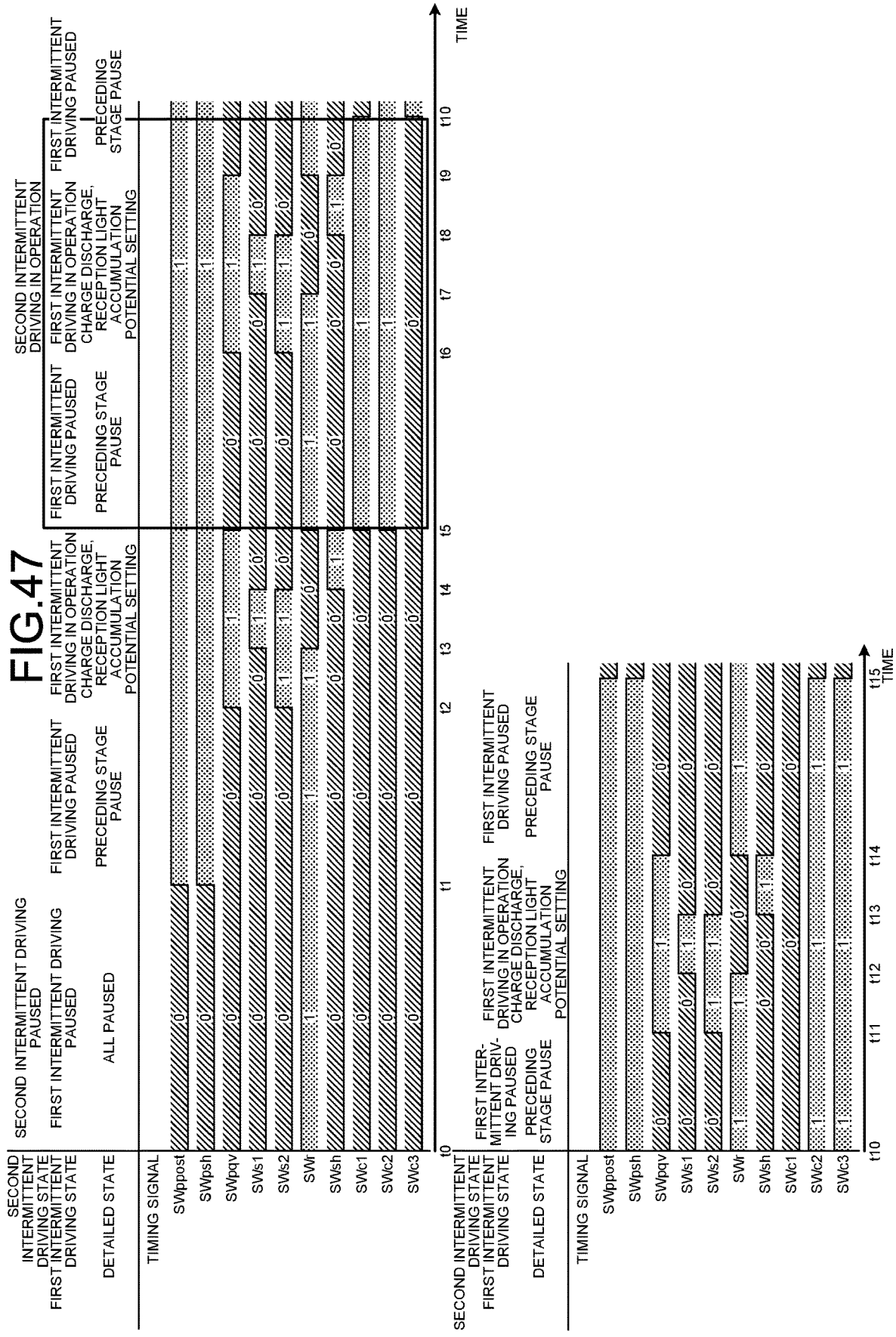
FIG. 47 is a diagram (2) for describing an example of opening/closing timing of each switch according to the second embodiment.

FIG. 47 is a diagram (2) for describing an example of opening/closing timing of each switch according to the second embodiment.

The opening/closing timing of switch SWppost will be described. Switch SWppos is a switch that switches between a pause and an operation of the AC amplifier 280. When switch SWppost is in the closed state, the AC amplifier 280 operates, and when switch SWppost is in the open state, the AC amplifier 280 pauses. Switch SWppost is in an open state between times t0 and t1. Switch SWppost is in a closed state between times t1 and t15. Switch SWppost becomes in an open state for a while after time t15 and then repeats the opening/closing timing illustrated in FIG. 47. The opening/closing timing of switch SWppost corresponds to the timing of the "second intermittent driving".

The opening/closing timing of switch SWpsh will be described. Switch SWpsh corresponds to Switch SWpsh illustrated in FIG. 9. Switch SWpsh is in an open state between times t0 and t1. Switch SWpsh is in a closed state between times t1 and t15. Although not illustrated, switch SWpsh becomes in an open state for a while after time t15 and then repeats the opening/closing timing illustrated in FIG. 47. The opening/closing timing of switch SWpsh corresponds to the timing of the "second intermittent driving".

The opening/closing timing of switch SWpqv will be described. Switch SWpqv corresponds to switch SWpqv illustrated in FIG. 9. Switch SWpqv is in an open state between times t0 and t2. Switch Wpqv is in a closed state between times t2 and t5. Switch SWpqv is in an open state between times t5 and t6. Switch SWpqv is in a closed state between times t6 and t9. Switch SWpqv is in an open state between times t9 and t11. Switch SWpqv is in a closed state between times t11 and t14. Although not illustrated, switch SWpqv becomes in an open state for a while after time t14 and then repeats the opening/closing timing illustrated in FIG. 47. The opening/closing timing of switch SWpqv corresponds to the timing of the "first intermittent driving".

The opening/closing timing of switch SWs1 will be described. Switch SWs1 corresponds to switch SWs1 illustrated in FIG. 9. Switch SWs1 is in an open state between times t0 and t3. Switch SWs1 is in a closed state between times t3 and t4. Switch SWs1 is in an open state between times t4 and t7. Switch SWs1 is in a closed state between times t7 and t8. Switch SWs1 is in an open state between times t8 and t12. Switch SWs1 is in a closed state between times t12 and t13. Although not illustrated, switch SWs1 becomes in an open state for a while after time t13 and then repeats the opening/closing timing illustrated in FIG. 47.

The opening/closing timing of switch SWs2 will be described. Switch SWs2 corresponds to switch SWs2 illustrated in FIG. 9. Switch SWs2 is in an open state between times t0 and t2. Switch SWs2 is in a closed state between times t2 and t4. Switch SWs2 is in an open state between times t4 and t6. Switch SWs2 is a closed state between times t6 and t8. Switch SWs2 is in an open state between times t8 and t11. Switch SWs2 is in a closed state between times t12 and t13. Switch SWs2 becomes in an open state for a while after time t13 and then repeats the opening/closing timing illustrated in FIG. 47.

The opening/closing timing of switch SWr will be described. Switch SWr corresponds to switch SWr illustrated in FIG. 9. Switch SWr is in a closed state between times t0 and t3. Switch SWr is in an open state between times t3 and t5. Switch SWr is a closed state between times t5 and t7. Switch SWr is in an open state between times t7 and t9. Switch SWr is in a closed state between times t9 and t12. Switch SWr is in an open state between times t12 and t14. Switch SWr becomes in a closed state for a while after time t14 and then repeats the opening/closing timing illustrated in FIG. 47.

The opening/closing timing of switch SWsh will be described. Switch SWsh corresponds to switch SWr illustrated in FIG. 9. Switch SWsh is in an open state between times t0 and t4. Switch SWsh is in a closed state between times t4 and t5. Switch SWsh is in an open state between times t5 and t8. Switch SWsh is in a closed state between times t8 and t9. Switch SWsh is in an open state between times t9 and t13. Switch SWsh is in a closed state between times t13 and t14. Switch SWsh becomes in an open state for a while after time t14 and then repeats the opening/closing timing illustrated in FIG. 47.

Next, opening/closing timings of switches SWc1, SWc2, and SWc3 will be described. For example, switches SWc1, SWc2, and SWc3 correspond to switches SWc1, SWc2, and SWc3 illustrated in FIG. 20.

Switch SWc1 is in an open state between times t0 and t5. Switch SWc1 is in a closed state between times t5 and t10. Switch SWc1 becomes in an open state for a while after time t10 and then repeats the opening/closing timing illustrated in FIG. 47.

Switch SWc2 is in an open state between times t0 and t5. Switch SWc2 is in a closed state between times t5 and t15. Switch SWc2 becomes in an open state for a while after time t15 and then repeats the opening/closing timing illustrated in FIG. 47.

Switch SWc3 is in an open state between times t0 and t10. Switch SWc3 is in a closed state between times t10 and t15. Switch SWc3 becomes in an open state for a while after time t15 and then repeats the opening/closing timing illustrated in FIG. 47.

In the example illustrated in FIG. 47, potential setting can be performed without consuming unnecessary power by extending the preceding stage pause period from time t5 to time t10 to the time required for the rapid potential setting. Alternatively, the rapid potential setting can be completed by performing a plurality of measurements in the state of the switch SWc1=1.

Figure 48:
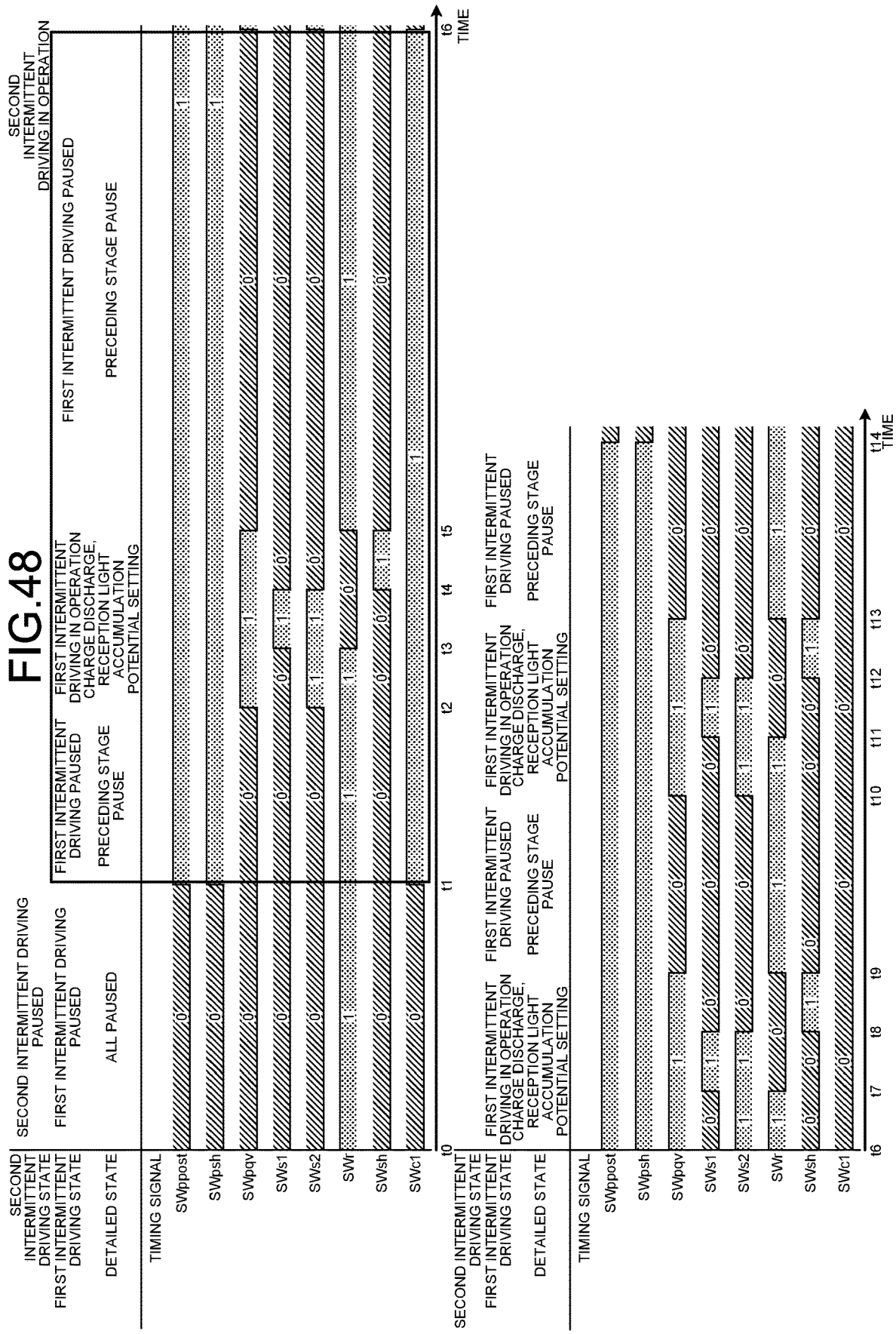
FIG. 48 is a diagram (3) for describing an example of opening/closing timing of each switch according to the second embodiment.

FIG. 48 is a diagram (3) for describing an example of opening/closing timing of each switch according to the second embodiment.

The opening/closing timing of switch SWppost will be described. Switch SWppos is a switch that switches between a pause and an operation of the AC amplifier 280. When switch SWppost is in the closed state, the AC amplifier 280 operates, and when switch SWppost is in the open state, the AC amplifier 280 pauses. Switch SWppost is in an open state between times t0 and t1. Switch SWppost is in a closed state between times t1 and t14. Switch SWppost becomes in an open state for a while after time t14 and then repeats the opening/closing timing illustrated in FIG. 48. The opening/closing timing of switch SWppost corresponds to the timing of the "second intermittent driving".

The opening/closing timing of switch SWpsh will be described. Switch SWpsh corresponds to Switch SWpsh illustrated in FIG. 9. Switch SWpsh is in an open state between times t0 and t1. Switch SWpsh is in a closed state between times t1 and t14. Although not illustrated, switch SWpsh becomes in an open state for a while after time t14 and then repeats the opening/closing timing illustrated in FIG. 48. The opening/closing timing of switch SWpsh corresponds to the timing of the "second intermittent driving".

The opening/closing timing of switch SWpqv will be described. Switch SWpqv corresponds to switch SWpqv illustrated in FIG. 9. Switch SWpqv is in an open state between times t0 and t2. Switch Wpqv is in a closed state between times t2 and t5. Switch SWpqv is in an open state between times t5 and t6. Switch SWpqv is in a closed state between times t6 and t9. Switch SWpqv is in an open state between times t9 and t10. Switch SWpqv is in a closed state between times t10 and t13. Although not illustrated, switch SWpqv becomes in an open state for a while after time t13 and then repeats the opening/closing timing illustrated in FIG. 48. The opening/closing timing of switch SWpqv corresponds to the timing of the "first intermittent driving".

The opening/closing timing of switch SWs1 will be described. Switch SWs1 corresponds to switch SWs1 illustrated in FIG. 9. Switch SWs1 is in an open state between times t0 and t3. Switch SWs1 is in a closed state between times t3 and t4. Switch SWs1 is in an open state between times t4 and t7. Switch SWs1 is in a closed state between times t7 and t8. Switch SWs1 is in an open state between times t8 and t11. Switch SWs1 is in a closed state between times t11 and t12. Although not illustrated, switch SWs1 becomes in an open state for a while after time t12 and then repeats the opening/closing timing illustrated in FIG. 48.

The opening/closing timing of switch SWs2 will be described. Switch SWs2 corresponds to switch SWs2 illustrated in FIG. 9. Switch SWs2 is in an open state between times t0 and t2. Switch SWs2 is in a closed state between times t2 and t4. Switch SWs2 is in an open state between times t4 and t6. Switch SWs2 is a closed state between times t6 and t8. Switch SWs2 is in an open state between times t8 and t10. Switch SWs2 is in a closed state between times t10 and t12. Switch SWs2 becomes in an open state for a while after time t12 and then repeats the opening/closing timing illustrated in FIG. 48.

The opening/closing timing of switch SWr will be described. Switch SWr corresponds to switch SWr illustrated in FIG. 9. Switch SWr is in a closed state between times t0 and t3. Switch SWr is in an open state between times t3 and t5. Switch SWr is a closed state between times t5 and t7. Switch SWr is in an open state between times t7 and t9. Switch SWr is a closed state between times t9 and t11. Switch SWr is in an open state between times t11 and t13. Switch SWr becomes in a closed state for a while after time t13 and then repeats the opening/closing timing illustrated in FIG. 48.

The opening/closing timing of switch SWsh will be described. Switch SWsh corresponds to switch SWr illustrated in FIG. 9. Switch SWsh is in an open state between times t0 and t4. Switch SWsh is in a closed state between times t4 and t5. Switch SWsh is in an open state between times t5 and t8. Switch SWsh is in a closed state between times t8 and t9. Switch SWsh is in an open state between times t9 and t12. Switch SWsh is in a closed state between times t12 and t13. Switch SWsh becomes in an open state for a while after time t13 and then repeats the opening/closing timing illustrated in FIG. 48.

The opening/closing timing of switch SWc1 will be described. Switch SWc1 corresponds to switch SWc1 illustrated in FIG. 16. Switch SWc1 is in an open state between times t0 and t1. Switch SWc1 is in a closed state between times t1 and t6. Switch SWc1 becomes in an open state for a while after time t6 and then repeats the opening/closing timing illustrated in FIG. 48.

In the configuration of only Switch SWc1 illustrated in FIG. 48, the charge of the coupling capacitor is discharged during the pause period of the second intermittent driving. Therefore, there is no problem even when the connection is made before the output of the S & H circuit 260 is determined. In the opening/closing example here, since switch SWc1 is connected during the potential setting period, the output potential stabilizes earlier accordingly.

Figure 49:
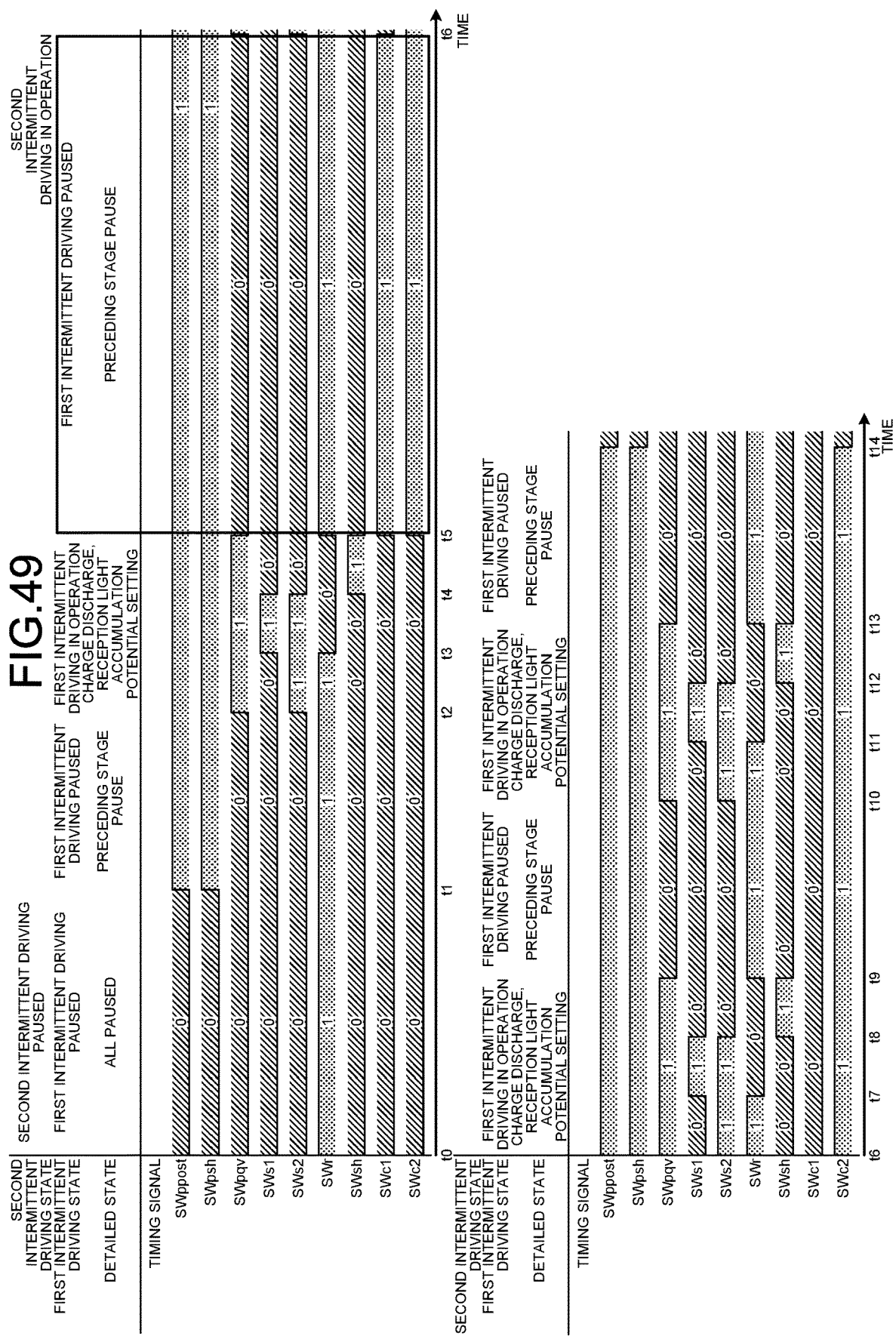
FIG. 49 is a diagram (4) for describing an example of opening/closing timing of each switch according to the second embodiment.

FIG. 49 is a diagram (4) for describing an example of opening/closing timing of each switch according to the second embodiment.

The opening/closing timing of switch SWppost will be described. Switch SWppos is a switch that switches between a pause and an operation of the AC amplifier 280. When switch SWppost is in the closed state, the AC amplifier 280 operates, and when switch SWppost is in the open state, the AC amplifier 280 pauses. Switch SWppost is in an open state between times t0 and t1. Switch SWppost is in a closed state between times t1 and t14. Switch SWppost becomes in an open state for a while after time t14 and then repeats the opening/closing timing illustrated in FIG. 49. The opening/closing timing of switch SWppost corresponds to the timing of the "second intermittent driving".

The opening/closing timing of switch SWpsh will be described. Switch SWpsh corresponds to Switch SWpsh illustrated in FIG. 9. Switch SWpsh is in an open state between times t0 and t1. Switch SWpsh is in a closed state between times t1 and t14. Although not illustrated, switch SWpsh becomes in an open state for a while after time t14 and then repeats the opening/closing timing illustrated in FIG. 49. The opening/closing timing of switch SWpsh corresponds to the timing of the "second intermittent driving".

The opening/closing timing of switch SWpqv will be described. Switch SWpqv corresponds to switch SWpqv illustrated in FIG. 9. Switch SWpqv is in an open state between times t0 and t2. Switch Wpqv is in a closed state between times t2 and t5. Switch SWpqv is in an open state between times t5 and t6. Switch SWpqv is in a closed state between times t6 and t9. Switch SWpqv is in an open state between times t9 and t10. Switch SWpqv is in a closed state between times t10 and t13. Although not illustrated, switch SWpqv becomes in an open state for a while after time t13 and then repeats the opening/closing timing illustrated in FIG. 49. The opening/closing timing of switch SWpqv corresponds to the timing of the "first intermittent driving".

The opening/closing timing of switch SWs1 will be described. Switch SWs1 corresponds to switch SWs1 illustrated in FIG. 9. Switch SWs1 is in an open state between times t0 and t3. Switch SWs1 is in a closed state between times t3 and t4. Switch SWs1 is in an open state between times t4 and t7. Switch SWs1 is in a closed state between times t7 and t8. Switch SWs1 is in an open state between times t8 and t11. Switch SWs1 is in a closed state between times t11 and t12. Although not illustrated, switch SWs1 becomes in an open state for a while after time t12 and then repeats the opening/closing timing illustrated in FIG. 49.

The opening/closing timing of switch SWs2 will be described. Switch SWs2 corresponds to switch SWs2 illustrated in FIG. 9. Switch SWs2 is in an open state between times t0 and t2. Switch SWs2 is in a closed state between times t2 and t4. Switch SWs2 is in an open state between times t4 and t6. Switch SWs2 is a closed state between times t6 and t8. Switch SWs2 is in an open state between times t8 and t10. Switch SWs2 is in a closed state between times t10 and t12. Switch SWs2 becomes in an open state for a while after time t12 and then repeats the opening/closing timing illustrated in FIG. 49.

The opening/closing timing of switch SWr will be described. Switch SWr corresponds to switch SWr illustrated in FIG. 9. Switch SWr is in a closed state between times t0 and t3. Switch SWr is in an open state between times t3 and t5. Switch SWr is a closed state between times t5 and t7. Switch SWr is in an open state between times t7 and t9. Switch SWr is a closed state between times t9 and t11. Switch SWr is in an open state between times t11 and t13. Switch SWr becomes in a closed state for a while after time t13 and then repeats the opening/closing timing illustrated in FIG. 49.

The opening/closing timing of switch SWsh will be described. Switch SWsh corresponds to switch SWsh illustrated in FIG. 9. Switch SWsh is in an open state between times t0 and t4. Switch SWsh is in a closed state between times t4 and t5. Switch SWsh is in an open state between times t5 and t8. Switch SWsh is in a closed state between times t8 and t9. Switch SWsh is in an open state between times t9 and t12. Switch SWsh is in a closed state between times t12 and t13. Switch SWsh becomes in an open state for a while after time t13 and then repeats the opening/closing timing illustrated in FIG. 49.

Next, opening/closing timings of switches SWc1 and SWc2 will be described. For example, switches SWc1 and SWc2 correspond to switches SWc1 and SWc2 illustrated in FIG. 31.

The opening/closing timing of switch SWc1 will be described. Switch SWc1 is in an open state between times t0 and t5. Switch SWc1 is in a closed state between times t5 and t6. Switch SWc1 becomes in an open state for a while after time t6 and then repeats the opening/closing timing illustrated in FIG. 49.

The opening/closing timing of switch SWc2 will be described. Switch SWc2 is in an open state between times t0 and t5. Switch SWc2 is in a closed state between times t5 and t14. Switch SWc2 becomes in an open state for a while after time t14 and then repeats the opening/closing timing illustrated in FIG. 49.

In the example described with reference to FIG. 49, the potential setting can be performed without consuming unnecessary power by extending the time required for the rapid potential setting from time t5 to t6 (preceding stage pause period). Alternatively, the rapid potential setting can also be completed by performing a plurality of measurements in the state of switch SWc1.

Figure 50:
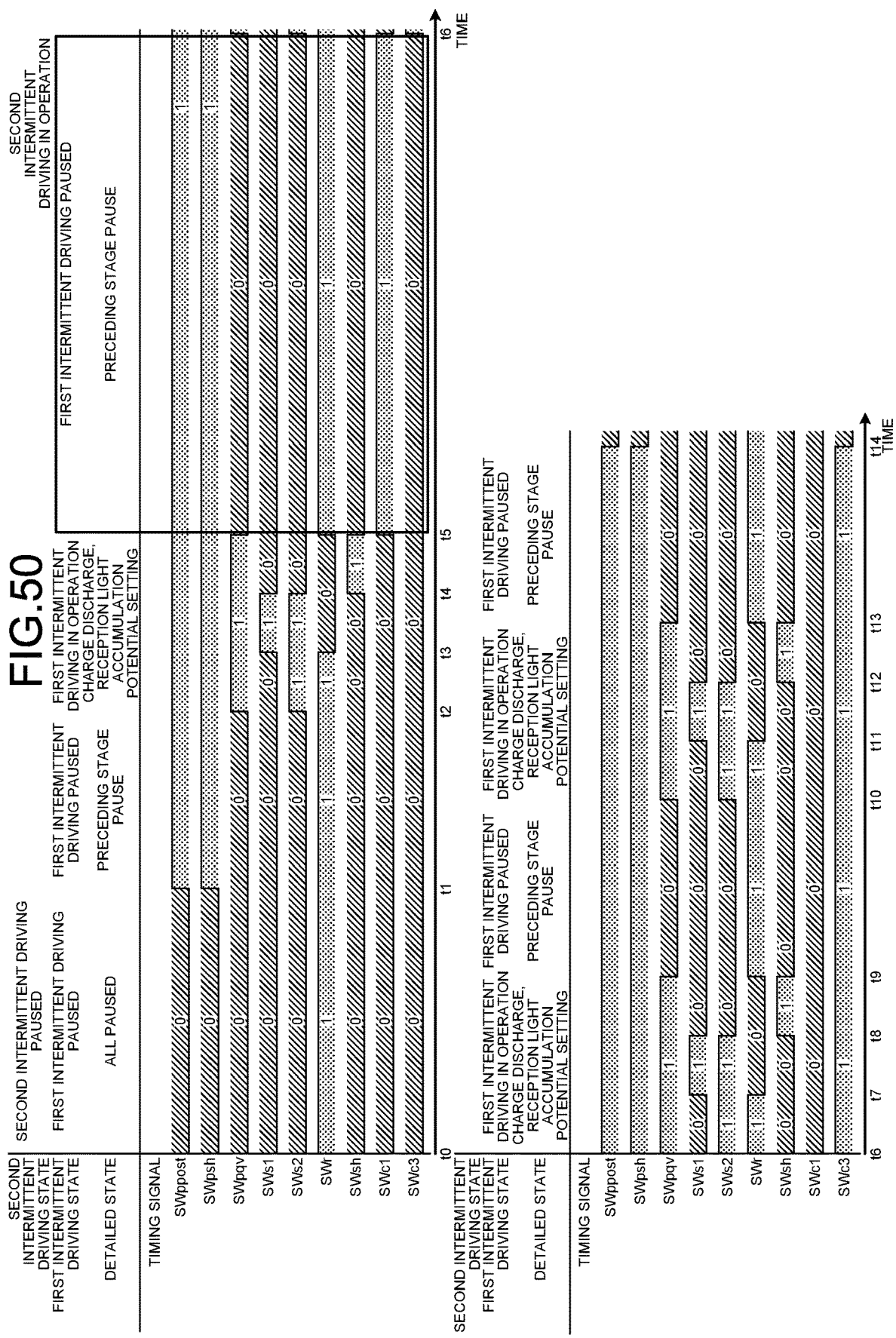
FIG. 50 is a diagram (5) for describing an example of opening/closing timing of each switch according to the second embodiment.

FIG. 50 is a diagram (5) for describing an example of opening/closing timing of each switch according to the second embodiment.

The opening/closing timing of switch SWppost will be described. Switch SWppos is a switch that switches between a pause and an operation of the AC amplifier 280. When switch SWppost is in the closed state, the AC amplifier 280 operates, and when switch SWppost is in the open state, the AC amplifier 280 pauses. Switch SWppost is in an open state between times t0 and t1. Switch SWppost is in a closed state between times t1 and t14. Switch SWppost becomes in an open state for a while after time t14 and then repeats the opening/closing timing illustrated in FIG. 50. The opening/closing timing of switch SWppost corresponds to the timing of the "second intermittent driving".

The opening/closing timing of switch SWpsh will be described. Switch SWpsh corresponds to Switch SWpsh illustrated in FIG. 9. Switch SWpsh is in an open state between times t0 and t1. Switch SWpsh is in a closed state between times t1 and t14. Although not illustrated, switch SWpsh becomes in an open state for a while after time t14 and then repeats the opening/closing timing illustrated in FIG. 50. The opening/closing timing of switch SWpsh corresponds to the timing of the "second intermittent driving".

The opening/closing timing of switch SWpqv will be described. Switch SWpqv corresponds to switch SWpqv illustrated in FIG. 9. Switch SWpqv is in an open state between times t0 and t2. Switch Wpqv is in a closed state between times t2 and t5. Switch SWpqv is in an open state between times t5 and t6. Switch SWpqv is in a closed state between times t6 and t9. Switch SWpqv is in an open state between times t9 and t10. Switch SWpqv is in a closed state between times t10 and t13. Although not illustrated, switch SWpqv becomes in an open state for a while after time t13 and then repeats the opening/closing timing illustrated in FIG. 50. The opening/closing timing of switch SWpqv corresponds to the timing of the "first intermittent driving".

The opening/closing timing of switch SWs1 will be described. Switch SWs1 corresponds to switch SWs1 illustrated in FIG. 9. Switch SWs1 is in an open state between times t0 and t3. Switch SWs1 is in a closed state between times t3 and t4. Switch SWs1 is in an open state between times t4 and t7. Switch SWs1 is in a closed state between times t7 and t8. Switch SWs1 is in an open state between times t8 and t11. Switch SWs1 is in a closed state between times t11 and t12. Although not illustrated, switch SWs1 becomes in an open state for a while after time t12 and then repeats the opening/closing timing illustrated in FIG. 50.

The opening/closing timing of switch SWs2 will be described. Switch SWs2 corresponds to switch SWs2 illustrated in FIG. 9. Switch SWs2 is in an open state between times t0 and t2. Switch SWs2 is in a closed state between times t2 and t4. Switch SWs2 is in an open state between times t4 and t6. Switch SWs2 is a closed state between times t6 and t8. Switch SWs2 is in an open state between times t8 and t10. Switch SWs2 is in a closed state between times t10 and t12. Switch SWs2 becomes in an open state for a while after time t12 and then repeats the opening/closing timing illustrated in FIG. 50.

The opening/closing timing of switch SWr will be described. Switch SWr corresponds to switch SWr illustrated in FIG. 9. Switch SWr is in a closed state between times t0 and t3. Switch SWr is in an open state between times t3 and t5. Switch SWr is a closed state between times t5 and t7. Switch SWr is in an open state between times t7 and t9. Switch SWr is a closed state between times t9 and t11. Switch SWr is in an open state between times t11 and t13. Switch SWr becomes in a closed state for a while after time t13 and then repeats the opening/closing timing illustrated in FIG. 50.

The opening/closing timing of switch SWsh will be described. Switch SWsh corresponds to switch SWsh illustrated in FIG. 9. Switch SWsh is in an open state between times t0 and t4. Switch SWsh is in a closed state between times t4 and t5. Switch SWsh is in an open state between times t5 and t8. Switch SWsh is in a closed state between times t8 and t9. Switch SWsh is in an open state between times t9 and t12. Switch SWsh is in a closed state between times t12 and t13. Switch SWsh becomes in an open state for a while after time t13 and then repeats the opening/closing timing illustrated in FIG. 50.

Next, opening/closing timings of switches SWc1 and SWc3 will be described. For example, switches SWc1 and SWc3 correspond to switches SWc1 and SWc3 illustrated in FIG. 32.

The opening/closing timing of switch SWc1 will be described. Switch SWc1 is in an open state between times t0 and t5. Switch SWc1 is in a closed state between times t5 and t6. Switch SWc1 becomes in an open state for a while after time t6 and then repeats the opening/closing timing illustrated in FIG. 50.

The opening/closing timing of switch SWc3 will be described. Switch SWc3 is in an open state between times t0 and t6. Switch SWc3 is in a closed state between times t6 and t14. Switch SWc3 becomes in an open state for a while after time t14 and then repeats the opening/closing timing illustrated in FIG. 50.

In the example described with reference to FIG. 50, the potential setting can be performed without consuming unnecessary power by extending the time t5 to t6 (preceding stage pause period) to the time required for the rapid potential setting. Alternatively, the rapid potential setting can also be completed by performing a plurality of measurements in the state of switch SWc1.

<<4.6. Coupling of Analog Filter with Rapid Potential Setting Mechanism and Differential Amplifier Circuit>>

Figure 51:
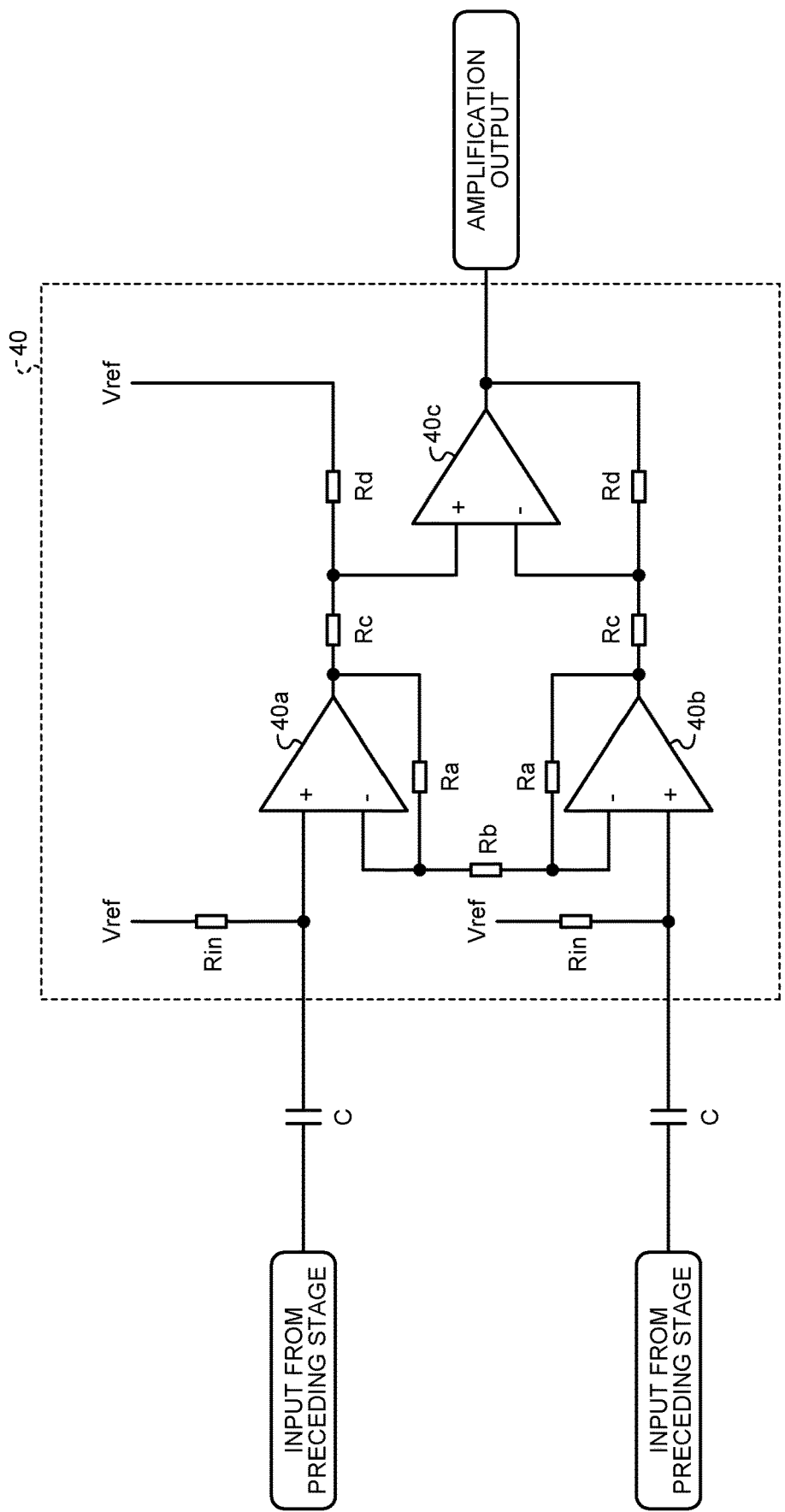
FIG. 51 is a diagram illustrating a configuration in which an analog filter and a differential amplifier circuit according to a comparative example are coupled.

The rapid potential mechanism and the analog filter described above can also be applied to a differential amplifier circuit. First, a configuration in which an analog filter and a differential amplifier circuit are coupled as a comparative example will be described. FIG. 51 is a diagram illustrating a configuration in which an analog filter and a differential amplifier circuit are coupled as a comparative example. In the example illustrated in FIG. 51, two capacitors C corresponding to the analog filter 15 are connected to a differential amplifier circuit 40. Although resistor Rin is included in the differential amplifier circuit 40 as an input resistor that applies a BIAS potential to the input end of the differential amplifier circuit 40, resistor Rin constitutes an analog low cut filter integrated with capacitor C, and is also a part of the analog filter 15. It is assumed that IV amplifiers (first IV amplifier and second IV amplifier) of different sequences are connected to the preceding stage of each analog filter 15. Although not illustrated, a first photoelectric conversion unit is connected to the first IV amplifier at the preceding stage. A second photoelectric conversion unit is connected to the second IV amplifier at the preceding stage.

Each analog filter 15 outputs the electric signal obtained by cutting off the DC component to the differential amplifier circuit 40 at the subsequent stage. The differential amplifier circuit 40 amplifies the electric signal based on the electric signal input from each analog filter 15 and outputs the amplified electric signal. For example, the differential amplifier circuit includes operational amplifiers 40a, 40b, and 40c, and resistors Rin, Ra, Rb, Rc, and Rd. Using the differential amplifier circuit can improve the accuracy of blood flow signal calculation by canceling in-phase noise, but there is a problem that the time constant of the analog filter 15 is long.

Figure 52:
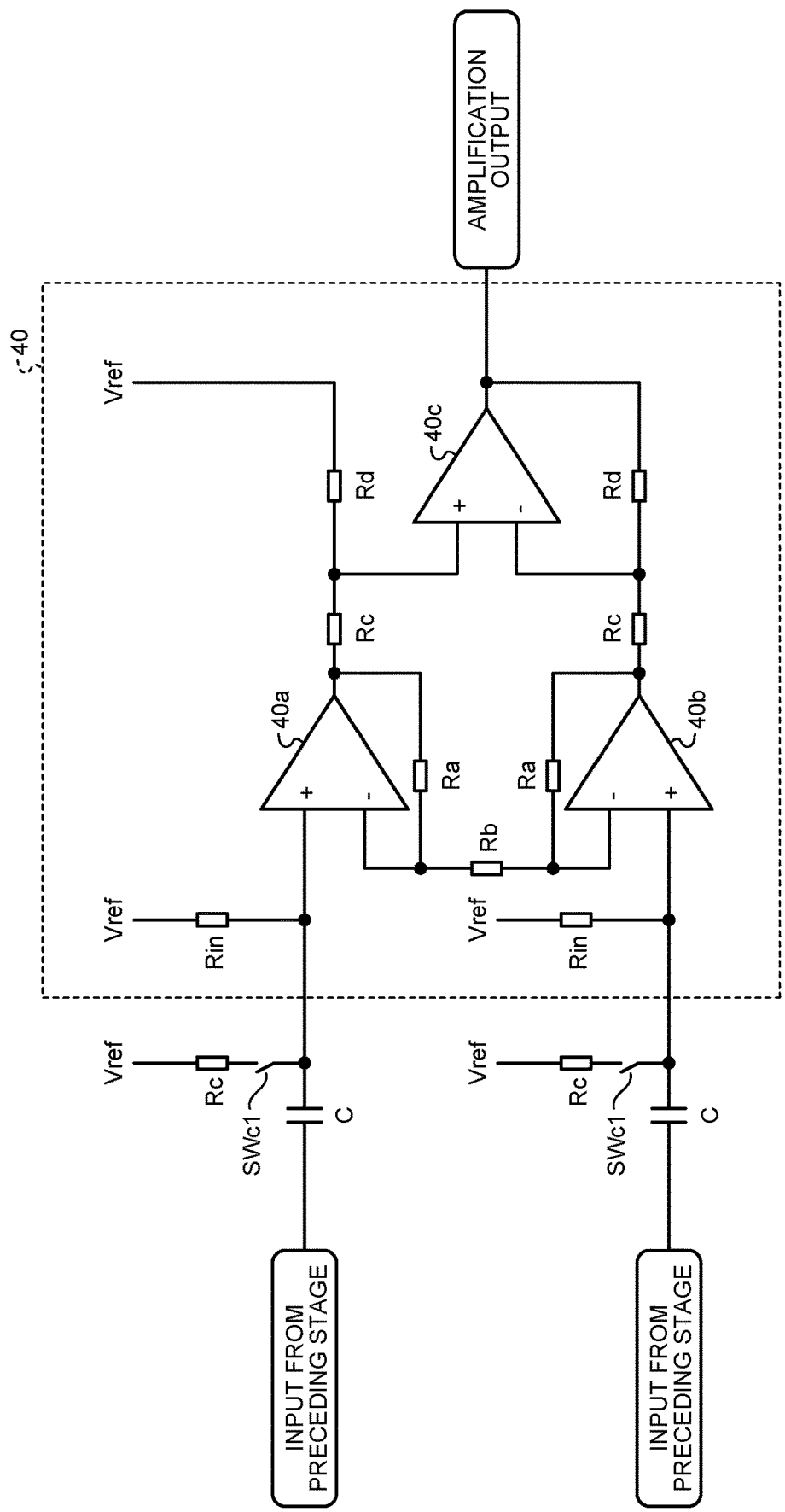
FIG. 52 is a diagram (1) illustrating a configuration in which an analog filter with a rapid potential setting mechanism and a differential amplifier circuit are coupled.

FIG. 52 is a diagram (1) illustrating a configuration in which an analog filter with a rapid potential setting mechanism and a differential amplifier circuit are coupled. In the example illustrated in FIG. 52, two of the analog filters with a rapid potential setting mechanism described in FIG. 16 are connected to the differential amplifier circuit 40. It is assumed that S & H circuits (first S & H circuit, second S & H circuit) of different sequences are connected as a preceding-stage amplifier to the preceding stage of each analog filter with a rapid potential setting mechanism. Although not illustrated, the first photoelectric conversion unit and a first QV amplifier are connected to the preceding stage of the first S & H circuit. The second photoelectric conversion unit and a second QV amplifier are connected to the preceding stage of the second S & H circuit. The rapid potential setting mechanism synchronizes with the recovery from the pause and closes Switch SWc1, which can temporarily reduce the time constant and rapidly stabilize the potential. In addition, using the differential amplifier circuit can improve the accuracy in the case of calculating the blood flow signal by canceling the in-phase noise component.

Figure 53:
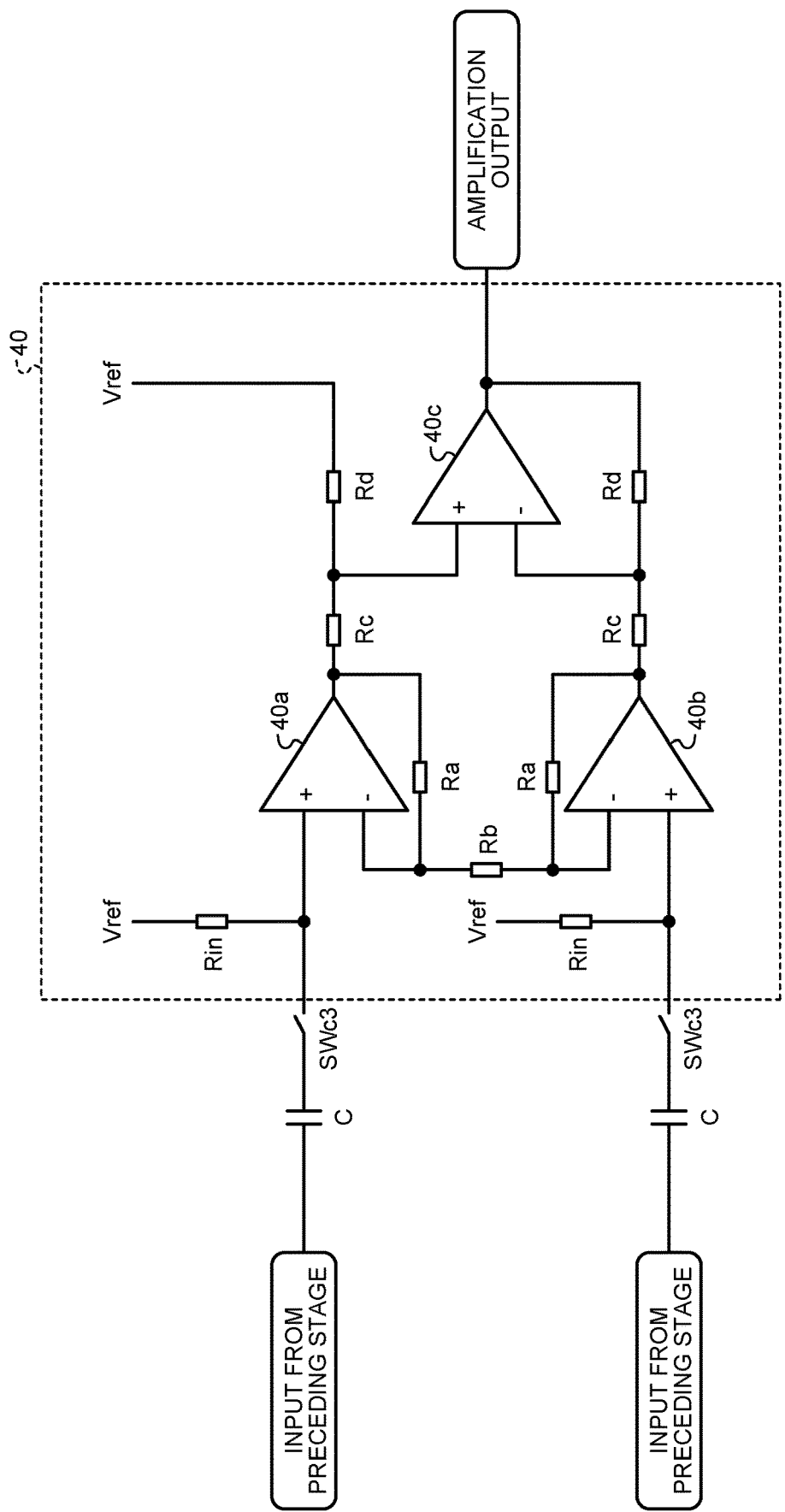
FIG. 53 is a diagram (2) illustrating a configuration in which an analog filter with a rapid potential setting mechanism and a differential amplifier circuit are coupled.

FIG. 53 is a diagram (2) illustrating a configuration in which an analog filter with a rapid potential setting mechanism and a differential amplifier circuit are coupled. In the example illustrated in FIG. 53, two of the analog filters with a rapid potential setting mechanism described in FIG. 18 are connected to the differential amplifier circuit 40. It is assumed that S & H circuits (first S & H circuit, second S & H circuit) of different sequences are connected as a preceding-stage amplifier to the preceding stage of each analog filter with a rapid potential setting mechanism. Although not illustrated, the first photoelectric conversion unit and a first QV amplifier are connected to the preceding stage of the first S & H circuit. The second photoelectric conversion unit and a second QV amplifier are connected to the preceding stage of the second S & H circuit. The rapid potential setting mechanism synchronizes with the pause period of the preceding-stage amplifier or the subsequent-stage amplifier, turns off switch SWc3, and retains the potential difference between both ends of the filter capacitor. Then, the rapid potential setting mechanism turns on switch SWc3 after the pause is released and the potentials of the preceding-stage amplifier and the subsequent-stage amplifier are stabilized.

Figure 54:
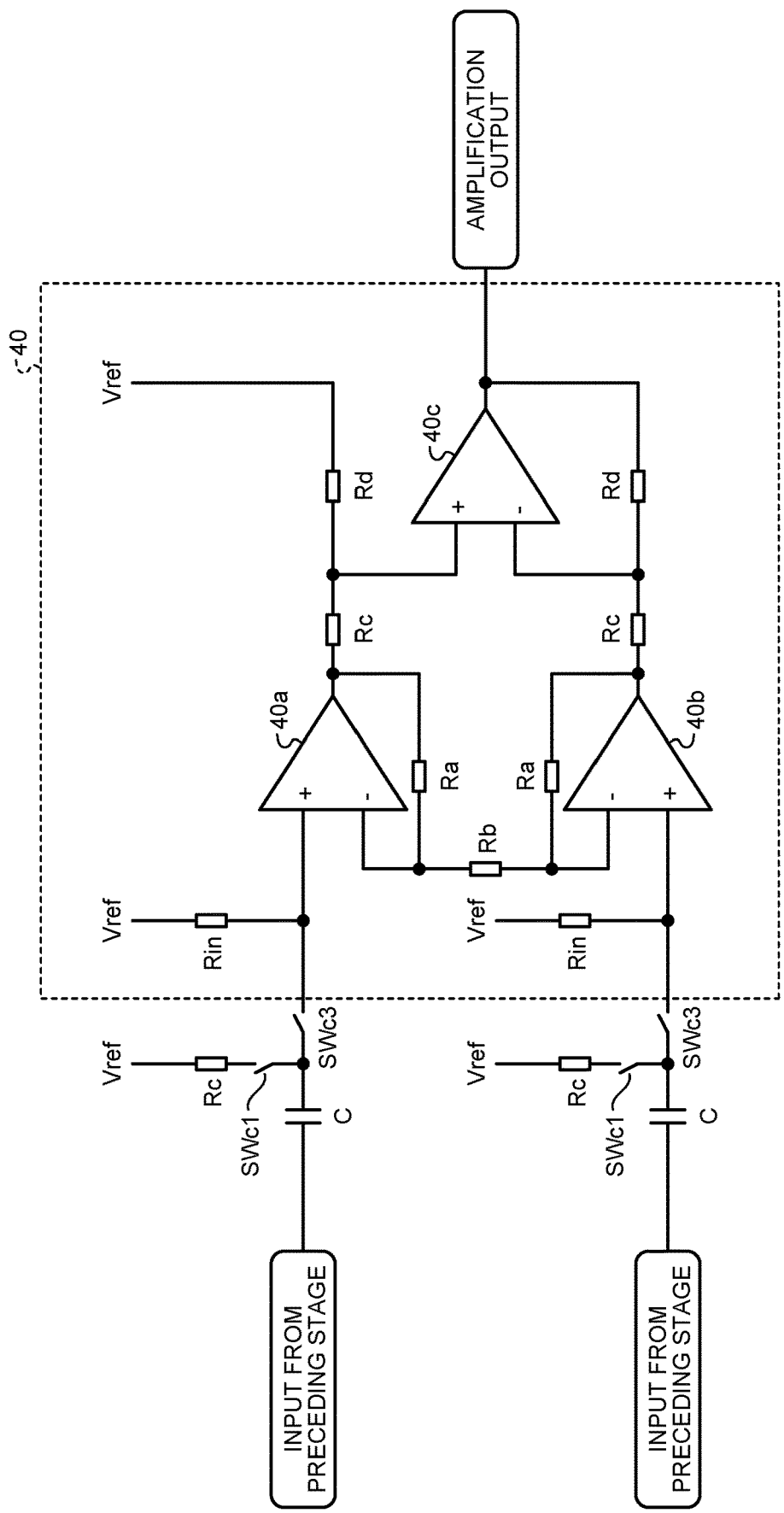
FIG. 54 is a diagram (3) illustrating a configuration in which an analog filter with a rapid potential setting mechanism and a differential amplifier circuit are coupled.

FIG. 54 is a diagram (3) illustrating a configuration in which an analog filter with a rapid potential setting mechanism and a differential amplifier circuit are coupled. In the example illustrated in FIG. 54, two of the analog filters with a rapid potential setting mechanism described in FIG. 20 are connected to the differential amplifier circuit 40. It is assumed that S & H circuits (first S & H circuit, second S & H circuit) of different sequences are connected as a preceding-stage amplifier to the preceding stage of each analog filter with a rapid potential setting mechanism.

Although not illustrated, the first photoelectric conversion unit and a first QV amplifier are connected to the preceding stage of the first S & H circuit. The second photoelectric conversion unit and a second QV amplifier are connected to the preceding stage of the second S & H circuit.

The rapid potential setting mechanism temporarily decreases the time constant by closing switch SWc1 in synchronization with the return from the pause. The rapid potential setting mechanism synchronizes with the pause period of the subsequent-stage amplifier, turns off switch SWc1 and switch SWc3, and retains the potential difference between both ends of the filter capacitor. Then, the rapid potential setting mechanism turns on switch SWc3 and turns off switch SWc1 after the stabilization waiting time shortened by the effect of turning on switch SWc1 has elapsed after the pause is released.

<<4.7. Coupling of Low-Pass Filter with Rapid Potential Setting Mechanism and Non-Inverting Amplifier Circuit>>

Figure 55:
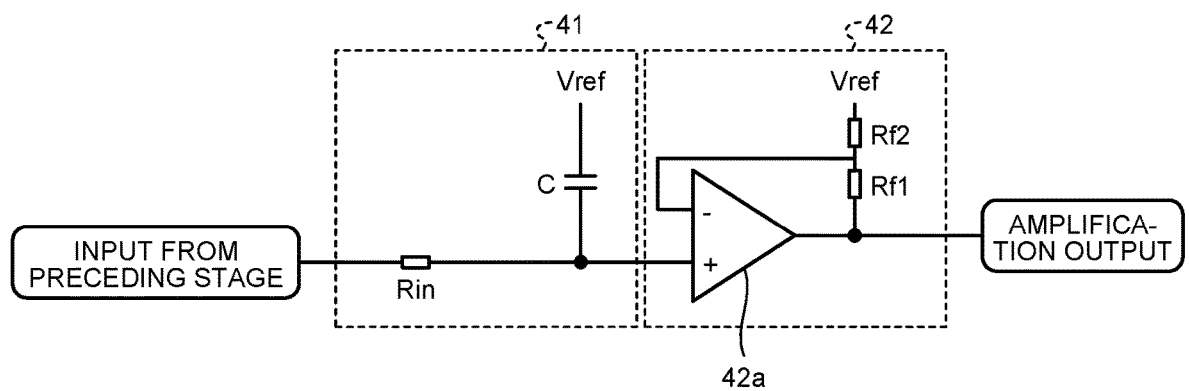
FIG. 55 is a diagram illustrating a configuration in which a low-pass filter and a non-inverting amplifier circuit according to a comparative example are coupled.

The rapid potential mechanism described above can also be applied to a low-pass filter. Although the increase in potential stabilization speed of the low-pass filter does not necessarily contribute to the reduction in power consumption of a blood flow sensor, it is disclosed because it is a function useful for the reduction in power consumption of general sensing. First, a configuration in which an analog filter and a non-inverting amplifier circuit are coupled as a comparative example will be described. FIG. 55 is a diagram illustrating a configuration in which a low-pass filter and a non-inverting amplifier circuit are coupled as a comparative example. In FIG. 55, a low-pass filter 41 includes capacitor C and resistor Rin. The low-pass filter 41 is connected to a potential Vref. A non-inverting amplifier circuit 42 includes operational amplifier 42a and resistors Rf1 and Rf2, and is connected to Vref.

The low-pass filter 41 receives an input of an electric signal from the preceding stage and accumulates charges in capacitor C. The low-pass filter 41 outputs the electric signal obtained by cutting off the high-frequency component to the non-inverting amplifier circuit 42 at the subsequent stage. The non-inverting amplifier circuit 42 amplifies the electric signal and outputs the amplified electric signal.

Hereinafter, a configuration including a low-pass filter with a rapid potential setting mechanism and a non-inverting amplifier circuit will be described.

Figure 56:
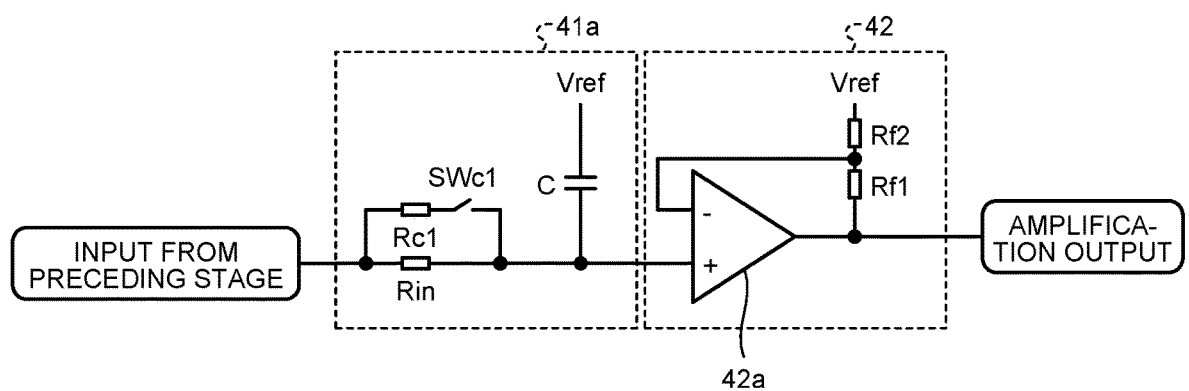
FIG. 56 is a diagram (1) illustrating a configuration including a low-pass filter with a rapid potential setting mechanism and a non-inverting amplifier circuit.

FIG. 56 is a diagram (1) illustrating a configuration including a low-pass filter with a rapid potential setting mechanism and a non-inverting amplifier circuit. In the example illustrated in FIG. 56, a low-pass filter 41a with a rapid potential setting mechanism includes switch SWc1, capacitor C, and resistors Rc1 and Rin. The low-pass filter 41a with a rapid potential setting mechanism temporarily decreases the time constant and rapidly stabilizes the potential by connecting resistor Rc1 to resistor Rin in parallel when switch SWc1 is closed in synchronization with the return from the pause based on the SW control signal output from the timing control unit 210. After the stabilization waiting time shortened by the effect of turning on switch SWc1 has elapsed, switch SWc1 is turned off.

The low-pass filter 41a outputs the electric signal obtained by cutting off the high-frequency component to the non-inverting amplifier circuit 42 at the subsequent stage. The non-inverting amplifier circuit 42 amplifies the electric signal and outputs the amplified electric signal.

Figure 57:
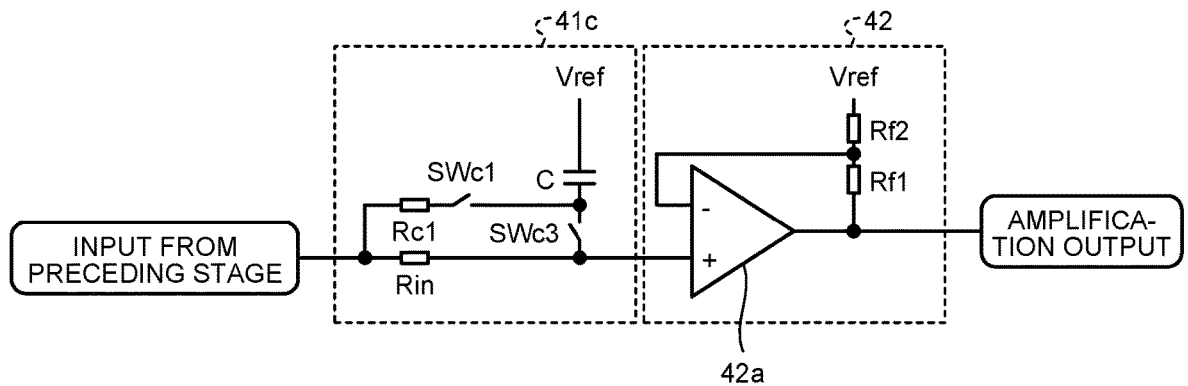
FIG. 57 is a diagram (3) illustrating a configuration including the low-pass filter with a rapid potential setting mechanism and the non-inverting amplifier circuit.

FIG. 57 is a diagram (2) illustrating a configuration including the low-pass filter with a rapid potential setting mechanism and the non-inverting amplifier circuit. In the example illustrated in FIG. 57, a low-pass filter 41c with a rapid potential setting mechanism includes switches SWc1, SWc3, resistors Rc1, Rin, and capacitor C, and is connected to potential Vref. The low-pass filter 41c with a rapid potential setting mechanism temporarily decreases the time constant and rapidly stabilizes the potential by connecting resistor Rc1 to resistor Rin in parallel when switch SWc1 is closed in synchronization with the return from the pause based on the SW control signal output from the timing control unit 210.

The low-pass filter 41c with a rapid potential setting mechanism turns off switches SWc1, SWc3 in synchronization with the input from the preceding stage or the pause period of the subsequent-stage amplifier based on the SW control signal output from the timing control unit 210, and retains the potential difference between both ends of capacitor C. Then, the rapid potential setting mechanism turns on switch SWc1 after the pause is released, and turns on switch SWc3 and turns off switch SWc1 after the stabilization waiting time shortened by the effect of turning on switch SWc1 has elapsed.

The low-pass filter 41c outputs the electric signal obtained by cutting off the high-frequency component to the non-inverting amplifier circuit 42 at the subsequent stage. The non-inverting amplifier circuit 42 amplifies the electric signal and outputs the amplified electric signal.

Figure 58:
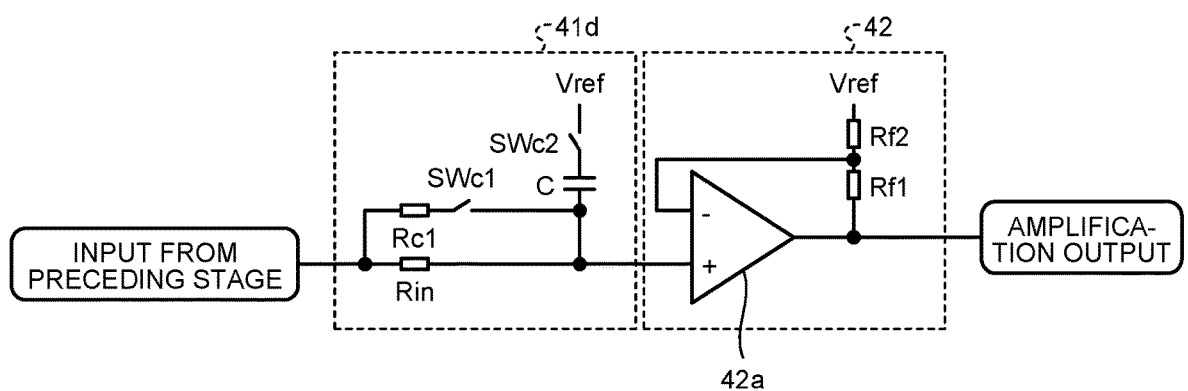
FIG. 58 is a diagram (4) illustrating a configuration including the low-pass filter with a rapid potential setting mechanism and the non-inverting amplifier circuit.

FIG. 58 is a diagram (3) illustrating a configuration including the low-pass filter with a rapid potential setting mechanism and the non-inverting amplifier circuit. In the example illustrated in FIG. 58, a low-pass filter 41d with a rapid potential setting mechanism includes switches SWc1 and SWc2, resistors Rc1 and Rin, and capacitor C, and is connected to potential Vref. The low-pass filter 41d with a rapid potential setting mechanism temporarily decreases the time constant and rapidly stabilizes the potential by connecting resistor Rc1 to resistor Rin in parallel when switch SWc1 is closed in synchronization with the return from the pause based on the SW control signal output from the timing control unit 210.

The low-pass filter 41d with a rapid potential setting mechanism turns off switch SWc2 in synchronization with the pause period of the subsequent-stage amplifier based on the SW control signal output from the timing control unit 210, and retains the potential difference between both ends of capacitor C. Then, the rapid potential setting mechanism turns on switch SWc1 and switch SWc2 after the pause is released and each potential is restored, and then turns off switch SWc1 after the stabilization waiting time shortened by the effect of turning on switch SWc1 has elapsed.

The low-pass filter 41d outputs the electric signal obtained by cutting off the high-frequency component to the non-inverting amplifier circuit 42 at the subsequent stage. The non-inverting amplifier circuit 42 amplifies the electric signal and outputs the amplified electric signal.

Figure 59:
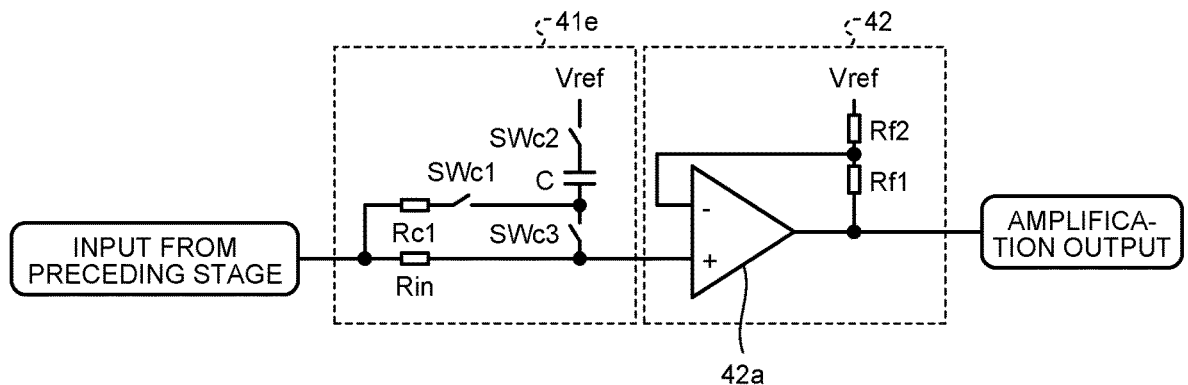
FIG. 59 is a diagram (5) illustrating a configuration including the low-pass filter with a rapid potential setting mechanism and the non-inverting amplifier circuit.

FIG. 59 is a diagram (4) illustrating a configuration including the low-pass filter with a rapid potential setting mechanism and the non-inverting amplifier circuit. In the example illustrated in FIG. 59, a low-pass filter 41e with a rapid potential setting mechanism includes switches SWc1, SWc2, and SWc3, resistors Rc1 and Rin, and capacitor C, and is connected to potential Vref. The low-pass filter 41e with a rapid potential setting mechanism temporarily decreases the time constant and rapidly stabilizes the potential by connecting resistor Rc1 to resistor Rin in parallel when switch SWc1 is closed in synchronization with the return from the pause based on the SW control signal output from the timing control unit 210.

The low-pass filter 41e with a rapid potential setting mechanism turns off switch SWc1, switch SWc2, and switch SWc3 in synchronization with the pause period of the subsequent-stage amplifier based on the SW control signal output from the timing control unit 210 and retains the potential difference between both ends of capacitor C. Then, the rapid potential setting mechanism turns on switch SWc1 and switch SWc2 after the pause is released and each potential is restored, and then turns on switch SWc3 and turns off switch SWc1 after the stabilization waiting time shortened by the effect of turning on switch SWc1 has elapsed.

The low-pass filter 41e outputs the electric signal obtained by cutting off the high-frequency component to the non-inverting amplifier circuit 42 at the subsequent stage. The non-inverting amplifier circuit 42 amplifies the electric signal and outputs the amplified electric signal.

<<4.8. Coupling of Low-Pass Filter with Rapid Potential Setting Mechanism and Inverting Amplifier Circuit>>

Figure 60:
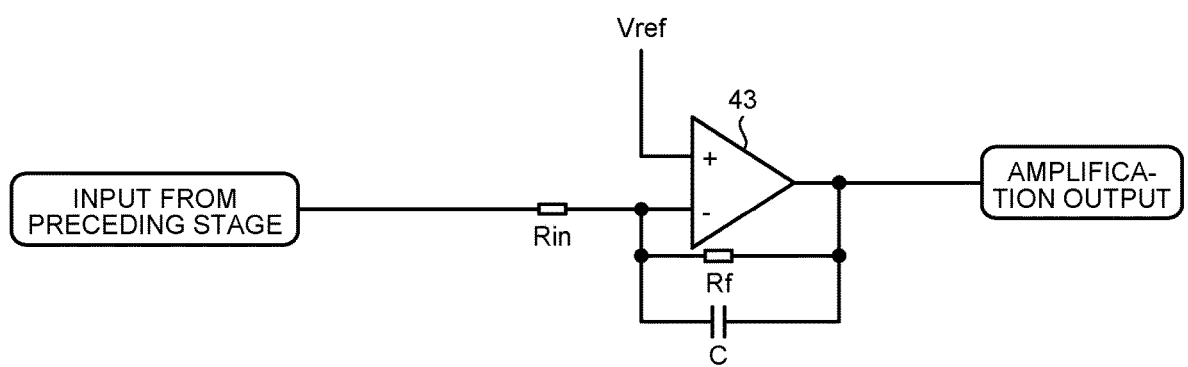
FIG. 60 is a diagram illustrating a configuration in which a low-pass filter and an inverting amplifier circuit according to a comparative example are coupled.

The rapid potential mechanism described above can also be applied to a low-pass filter and an inverting amplifier circuit. First, a configuration in which an analog filter and an inverting amplifier circuit are coupled as a comparative example will be described. FIG. 60 is a diagram illustrating a configuration in which a low-pass filter and an inverting amplifier circuit are coupled as a comparative example. In FIG. 60, the low-pass filter corresponds to capacitor C and resistor Rf. The inverting amplifier circuit corresponds to operational amplifier 43, Rin, capacitor C, and resistor Rf. In the case of the inverting amplifier circuit, the low-pass filter constitutes a part of the inverting amplifier circuit.

The circuit illustrated in FIG. 60 cuts off a high-frequency component of the electric signal input from the preceding stage, amplifies the electric signal, and then outputs the electric signal.

Figure 61:
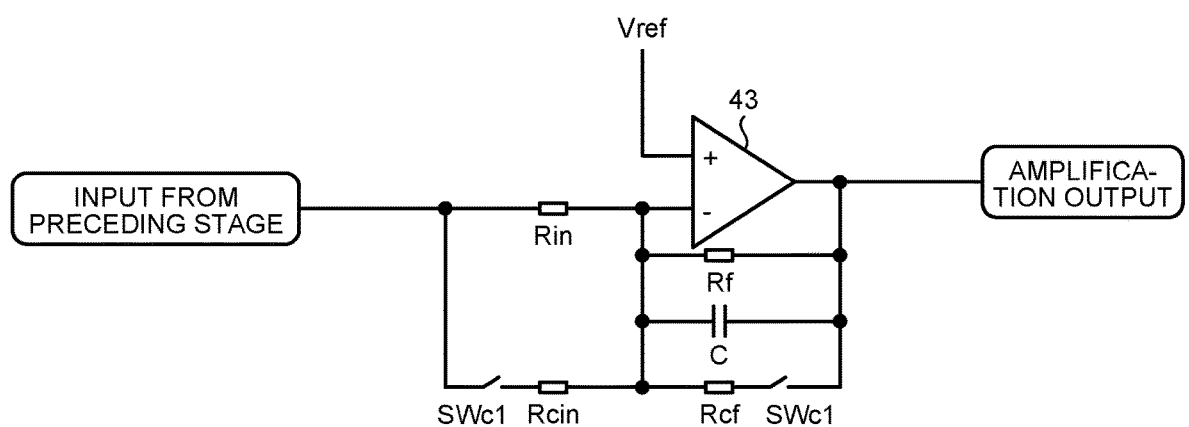
FIG. 61 is a diagram illustrating a configuration including a low-pass filter with a rapid potential setting mechanism and an inverting amplifier circuit.

Next, a configuration including a low-pass filter with a rapid potential setting mechanism and an inverting amplifier circuit will be described. FIG. 61 is a diagram illustrating a configuration including a low-pass filter with a rapid potential setting mechanism and an inverting amplifier circuit. In FIG. 61, the low-pass filter with a rapid potential setting mechanism corresponds to capacitor C, switch SWc1, and resistors Rf, Rcin, and Rcf. The inverting amplifier circuit corresponds to operational amplifier 43, Rin, capacitor C, and resistor Rf.

The circuit of FIG. 61 temporarily decreases the time constant and rapidly stabilizes the potential by synchronizing with the return from the pause based on the SW control signal output from the timing control unit 210, and connecting resistors Rcin and Rcf to resistors Rin and Rf in parallel when switch SWc1 is closed. The potential at the left end of capacitor C is rapidly set to a steady value while the resistance ratio is maintained by the two resistors Rcin and Rcf.

<<4.9. Effects of Measurement Device According to Second Embodiment>>

The measurement device 200 according to the second embodiment is provided with the rapid potential setting mechanism 275A, and the rapid potential setting mechanism 275A rapidly stabilizes the potential of the analog filter 270 by closing a switch that shortens the time constant of the analog filter 270 in synchronization with recovery from the pause based on the SW control signal output from the timing control unit 210. For example, as described with reference to FIG. 13, the time until the potential of the analog filter 270 is stabilized is shortened as compared with the conventional technology, and the minute signal amplifiable period can be lengthened.

Alternatively, the measurement device 200 is provided with the rapid potential setting mechanism 275B, and the rapid potential setting mechanism 275B is provided with a cutoff switch at least one of both ends of the filter capacitor of the analog filter 270, is cut off by the cutoff switch before the S & H circuit 260 or the AC amplifier 280 is powered off, and is connected after the output potential of the S & H circuit 260 and the input BIAS potential of the AC amplifier 280 are stabilized, thereby retaining the potential difference between both ends of the filter capacitor of the analog filter 270. For example, as described with reference to FIG. 14, since the potential difference between both ends of the filter capacitor of the analog filter 270 is kept constant by the same effect as that of the S & H circuit 260, only the potential difference between the samples of the electric signal is generated, and the electric signal having the potential at which the AD conversion can be immediately performed is output, and the minute signal amplifiable period can be lengthened as compared with the conventional technology.

The measurement device 200 can also be provided with the rapid potential setting mechanism 275C in which characteristics of the rapid potential setting mechanism 275A and the rapid potential setting mechanism 275B are combined.

FIG. 62 is a diagram for describing a relationship between types and characteristics of a switch set in the rapid potential setting mechanism. For example, the characteristics include the presence or absence of time constant reduction, the presence or absence of C charge retention, the potential difference between both ends required for charging (charging-requiring potential difference), the presence or absence of glitch noise at the start of output, the level of glitch noise, the length of glitch noise, other advantages, and other disadvantages. The potential difference between both ends is obtained by subtracting the BIAS potential of the subsequent stage from the output DC potential of the measurement period of the preceding stage.

Characteristics of a case where the switch is not used (conventional technology) will be described. Time constant reduction is "absent", C charge retention is "absent", charging-requiring potential difference is "current potential difference between both ends", glitch noise is "present", a level of glitch noise is "large", and length of glitch noise is "short".

Characteristics of a case where "switch SWc1" is used as the rapid potential setting mechanism 275 will be described. Time constant reduction is "present", C charge retention is "absent", charging-requiring potential difference is "current potential difference between both ends", glitch noise is "present", level of glitch noise is "large", and length of glitch noise is "short". In a case where switch SWc1 is used as the rapid potential setting mechanism, a simple circuit is obtained.

Characteristics of a case where "switch SWc2" is used as the rapid potential setting mechanism 275 will be described. Time constant reduction is "absent", C charge retention is "present", charging-requiring potential difference is "previous potential difference between both ends—current potential difference between both ends", glitch noise is "present", level of glitch noise is "small", and length of glitch noise is "slightly short". When switch SWc2 is used as the rapid potential setting mechanism 275, the rapid potential setting mechanism 275 can be integrated with the preceding circuit.

Characteristics of a case where "switch SWc3" is used as the rapid potential setting mechanism 275 will be described. Time constant reduction is "absent", C charge retention is "present", charging-requiring potential difference is "previous potential difference between both ends—current potential difference between both ends", glitch noise is "present", level of glitch noise is "small", and length of glitch noise is "slightly short". When switch SWc3 is used as the rapid potential setting mechanism 275, the rapid potential setting mechanism 275 can be integrated with the circuit at the subsequent stage.

Characteristics of a case where "switches SWc2 and SWc3" are used as the rapid potential setting mechanism 275 will be described. Time constant reduction is "absent", C charge retention is "present (advanced)", charging-requiring potential difference is "previous electric potential difference between both ends—current potential difference between both ends", glitch noise is "present", level of glitch noise is "small", and length of glitch noise is "slightly short". In a case where switches SWc2 and SWc3 are used as the rapid potential setting mechanism 275, since the discharge amount of capacitor C is small, it is possible to cope with a longer pause period as compared with a case where only one of switch SWc2 or switch SWc3 is used. However, it is necessary to set the switches on both sides, and it is necessary to integrate the switches with the circuits of both the preceding and subsequent stages.

Characteristics of a case where "switches SWc1 and SWc2" are used as the rapid potential setting mechanism 275 will be described. Time constant reduction is "present", C charge retention is "present", charging-requiring potential difference is "previous potential difference between both ends—current potential difference between both ends", glitch noise is "present", level of glitch noise is "small", and length of glitch noise is "short". When switches SWc1 and SWc2 are used as the rapid potential setting mechanism 275, it is necessary to set the switches on both sides.

Characteristics of a case where "switches SWc1 and SWc3" are used as the rapid potential setting mechanism 275 will be described. Time constant reduction is "present", C charge retention is "present", charging-requiring potential difference is "previous potential difference between both ends—current potential difference between both ends", glitch noise is "absent", level of glitch noise is "absent", and length of glitch noise is "absent". When switches SWc1 and SWc3 are used as the rapid potential setting mechanism 275, the glitch noise can be eliminated. In addition, it can be integrated with the circuit at the subsequent stage.

Characteristics of a case where "switches SWc1, SWc2, and SWc3" are used as the rapid potential setting mechanism 275 will be described. Time constant reduction is "present", C charge retention is "present (advanced)", charging-requiring potential difference is "previous potential difference between both ends—current potential difference between both ends", glitch noise is "absent", level of glitch noise is "absent", and length of glitch noise is "absent". When switches SWc1, SWc2, and SWc3 are used as the rapid potential setting mechanism 275, it is possible to eliminate glitch noise, and the discharge amount of capacitor C is small, which can cope with a longer pause period as compared with a case where only one of switch SWc2 or switch SWc3 is used. However, it is necessary to install the switches on both sides, and it is necessary to integrate the switches with the circuits of both the preceding and subsequent stages.

5. Third Embodiment

<<5.1. Configuration of Measurement Device According to Third Embodiment>>

Figure 63:
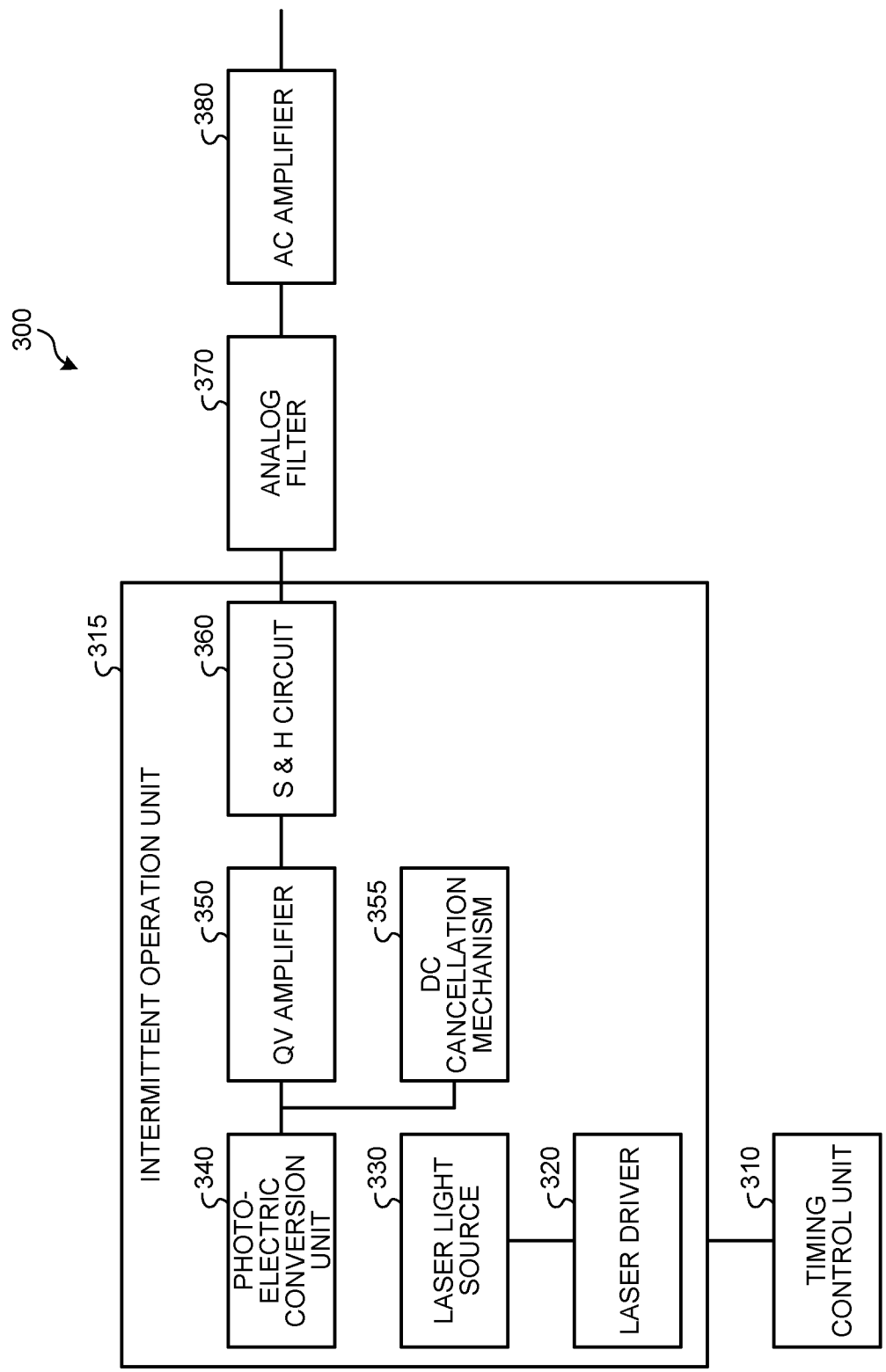
FIG. 63 is a diagram illustrating a configuration example of a measurement device according to a third embodiment.

FIG. 63 is a diagram illustrating a configuration example of a measurement device according to a third embodiment. As illustrated in FIG. 63, a measurement device 300 includes a timing control unit 310, an intermittent driving laser driver 320, a laser light source 330, a photoelectric conversion unit 340, a QV amplifier 350, a DC cancellation mechanism 355, an S & H circuit 360, an analog filter 370, and an AC amplifier 380.

The intermittent driving laser driver 320, the laser light source 330, the photoelectric conversion unit 340, the QV amplifier 350, the DC cancellation mechanism 355, and the S & H circuit 360 are collectively referred to as an intermittent operation unit 315.

The timing control unit 310 is a processing unit that controls a timing at which the intermittent operation unit 315 intermittently operates. For example, the timing control unit 310 outputs each SW control signal to the intermittent driving laser driver 320, the DC cancellation mechanism 355, the QV amplifier 350, and the S & H circuit 360 of the intermittent operation unit 315.

The description of the intermittent driving laser driver 320, the laser light source 330, the photoelectric conversion unit 340, the QV amplifier 350, and the S & H circuit 360 is the same as the description of the intermittent driving laser driver 120, the laser light source 130, the photoelectric conversion unit 140, the QV amplifier 150, and the S & H circuit 160 described in the first embodiment.

The DC cancellation mechanism 355 is a circuit that cancels an intermittent DC component of the electric signal output from the photoelectric conversion unit 340. The DC cancellation mechanism 355 is an example of a "canceling mechanism unit". For example, as described in the first embodiment, the photoelectric conversion unit 340 receives (intermittently receives) light (scattered light) reflected when laser light is intermittently output, converts the light into an electric signal including an intermittent DC component corresponding to the intensity of the intermittently changing light, and outputs the converted electric signal to the QV amplifier 350. Here, the DC cancellation mechanism 355 cancels the DC component of the intermittent electric signal converted in the intermittent light reception by adding an electric signal having an intermittent DC component of an opposite sign. By canceling the DC component, the total amount of the integrated electric signals of the QV amplifier 350 can be greatly reduced, and the amplification factor can be increased.

The analog filter 370 is a filter that cuts off the DC component remaining in the electric signal input from the S & H circuit 360 and not canceled out by the DC cancellation mechanism. The analog filter 370 outputs the electric signal obtained by cutting off the DC component to the AC amplifier 380.

The AC amplifier 380 is an amplifier that amplifies the electric signal input from the analog filter 370. The AC amplifier 380 outputs the amplified electric signal to an external device (not illustrated). The external device calculates a blood flow signal based on the Doppler beat on the basis of the electric signal output from the AC amplifier 380.

<<5.2. Configuration of Photoelectric Conversion Unit and Initial-Stage Amplifier According to Third Embodiment>>

Figure 64:
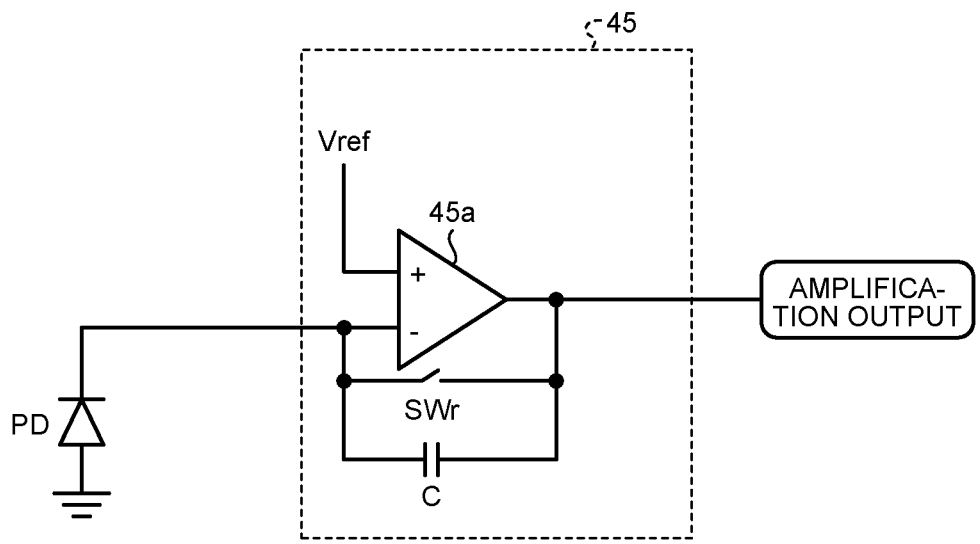
FIG. 64 is a diagram illustrating a configuration including a photoelectric conversion unit and an initial-stage amplifier but not including a DC cancellation mechanism.

First, a configuration including a photoelectric conversion unit and a first-stage amplifier but not including the DC cancellation mechanism 355 will be described. FIG. 64 is a diagram illustrating a configuration including a photoelectric conversion unit and an initial-stage amplifier but not including a DC cancellation mechanism. In FIG. 64, PD converts the received light into a charge of an amount corresponding to the amount of the light, and outputs the generated charge to an initial-stage amplifier 45. The charge amount corresponds to the above-described electric signal. The initial-stage amplifier 45 outputs a potential corresponding to the input charge amount to the subsequent stage as an electric signal. The initial-stage amplifier 45 includes operational amplifier 45a, switch SWr, and capacitor C. For example, switch SWr is a switch for resetting the charge of capacitor C.

Next, a configuration including a photoelectric conversion unit and an initial-stage amplifier according to a third embodiment and including a DC cancellation mechanism will be described.

Figure 65:
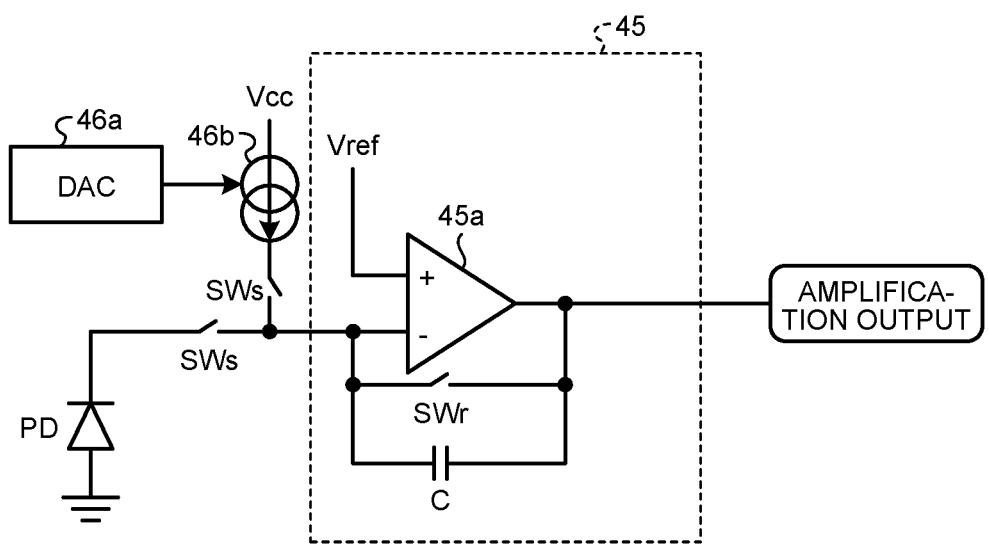
FIG. 65 is a diagram (1) illustrating a configuration including a photoelectric conversion unit and an initial-stage amplifier according to the third embodiment.

FIG. 65 is a diagram (1) illustrating a configuration including a photoelectric conversion unit and an initial-stage amplifier according to the third embodiment. In FIG. 65, PD converts the received light into a charge of an amount corresponding to the amount of the light, and outputs the generated charge to the initial-stage amplifier 45. The DC cancellation mechanism 355 corresponds to switch SWs, a digital analog converter (DAC) 46a, and a current source 46b. The initial-stage amplifier 45 corresponds to the QV amplifier 350.

Switch SWs is a switch that is turned on when the intermittent light reception starts and turned off when the intermittent light reception ends. The DAC 46a and the current source 46b operate in cooperation, and when switch SWs is turned on, a current is input from VCC to the circuit side to cancel the DC current flowing from PD to the ground. The DAC 46a and the current source 46b adjust the magnitude of the current input from the VCC side to the circuit side so that the current is approximately balanced with the amount of charge generated by the PD per unit time determined according to the amount of light incident on PD. By the DC cancellation mechanism 355, a differential current obtained by removing a current of a predefined magnitude (DC component) from a current of a magnitude corresponding to the light amount output from PD during the intermittent operation is input to the initial-stage amplifier 45. As a result, the amount of charge input to the initial-stage amplifier 45 in one intermittent operation can significantly decrease, and the amplification factor of the initial-stage amplifier 45 can increase.

Figure 66:
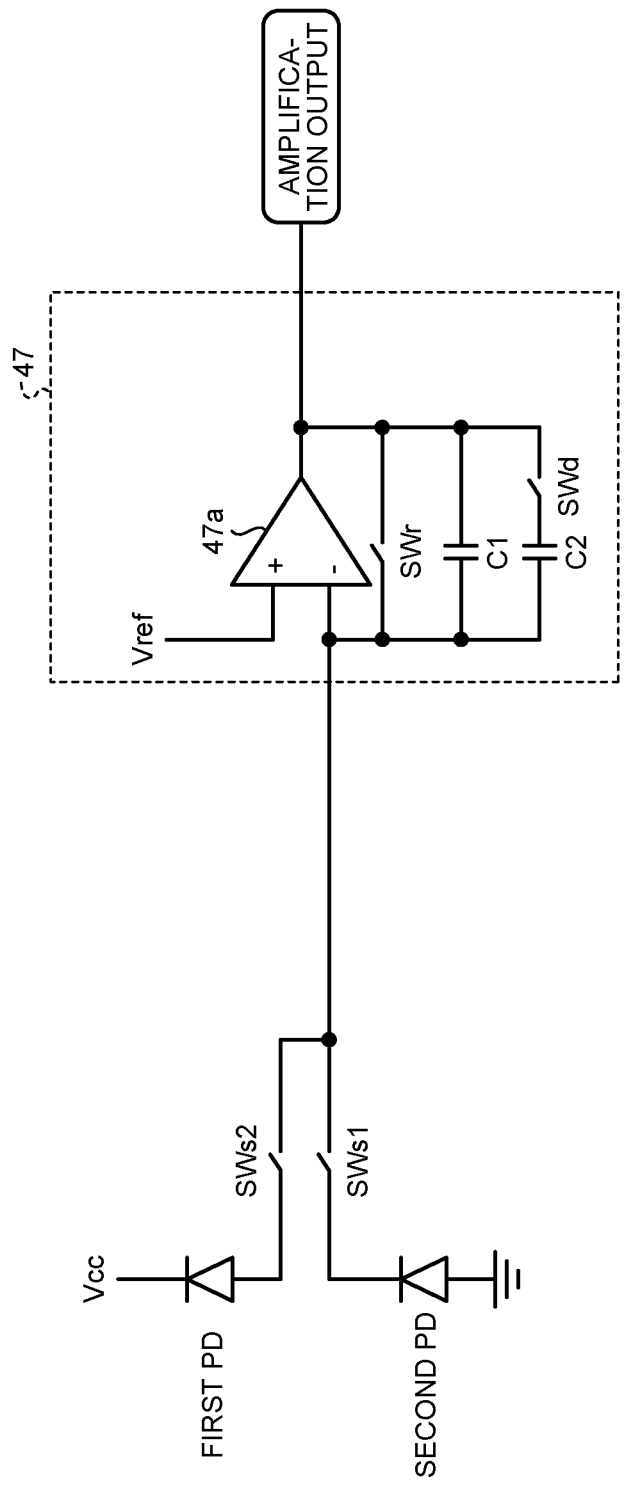
FIG. 66 is a diagram (2) illustrating a configuration including the photoelectric conversion unit and the initial-stage amplifier according to the third embodiment.

FIG. 66 is a diagram (2) illustrating a configuration including a photoelectric conversion unit and an initial-stage amplifier according to a third embodiment. In FIG. 66, first PD, second PD, and switches SWs1 and SWs2 correspond to the photoelectric conversion unit 340 and the DC cancellation mechanism 355.

Switches SWs1 and SWs2 are switches that are turned on when the intermittent light reception starts and turned off when the intermittent light reception ends. When first PD receives light, current flows from Vcc to the circuit side. On the other hand, when second PD receives light, current flows from the circuit to the ground side. When first PD and second PD are disposed close to each other, the received light amounts of both PDs at each time point become substantially equal, and most of the current generated in both PDs flows through both PDs and is not output toward an initial-stage amplifier 47. As a result, the DC component of the electric signal input from photoelectric conversion unit 340 to the initial-stage amplifier 47 is cut off. As a result, the amount of charge input to the initial-stage amplifier 47 in one intermittent operation can significantly decrease, and the amplification factor of the initial-stage amplifier 47 can increase. DC cancel function can be intentionally turned off by turning on only one of switch SWs1 or switch SWs2.

The initial-stage amplifier 47 includes operational amplifier 47a, capacitors C1 and C2, switch SWr, and switch SWd. The initial-stage amplifier 47 corresponds to QV amplifier 350. The initial-stage amplifier 46 amplifies the input electric signal and outputs the amplified electric signal. For example, switch SWr is a switch for resetting the charges of capacitors C1 and C2. Switch SRd is used to increase the capacitance of the capacitor for integration so that operational amplifier 47a does not cause a saturation phenomenon even when a DC component is input when the DC cancellation function is intentionally turned off for the purpose of measuring the amount of incident light. Since the initial-stage amplifier 47 outputs a DC value corresponding to the amount of received light by intentionally turning off the DC cancel function and turning on switch SWd, the amount of received light of the sensor can be measured by measuring the voltage value using an external circuit (not illustrated).

Figure 67:
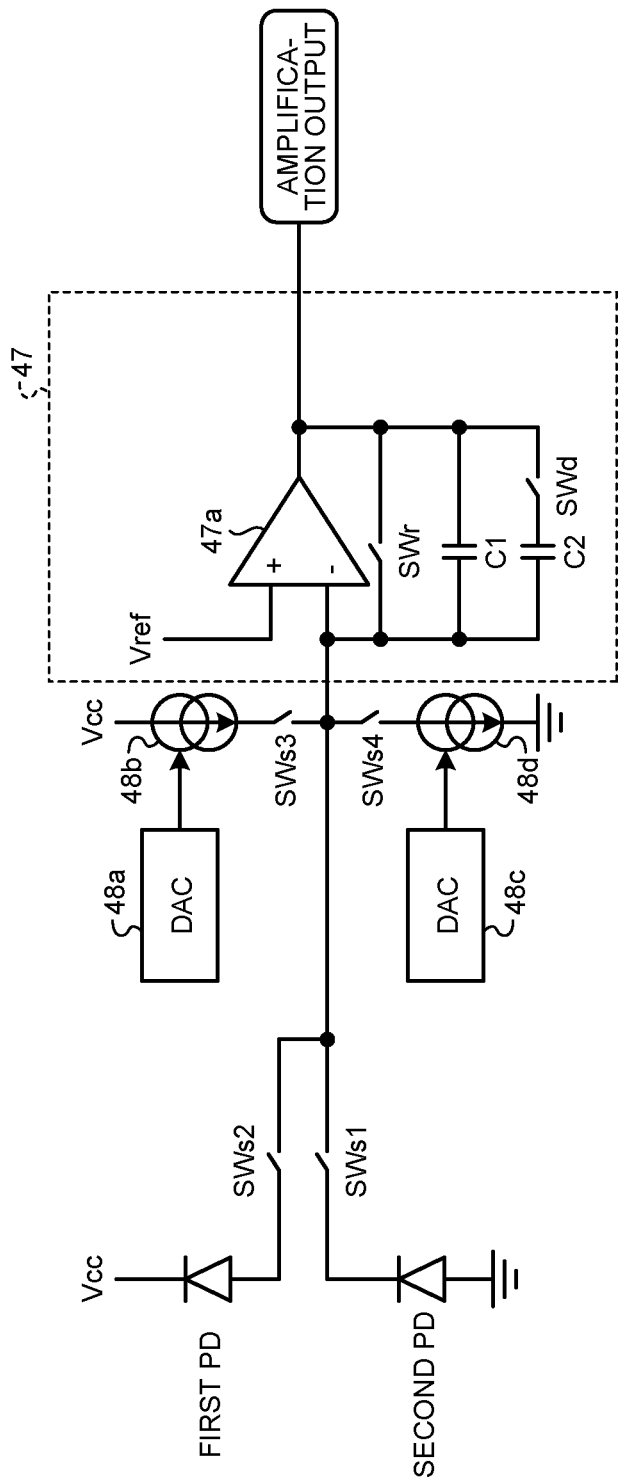
FIG. 67 is a diagram (3) illustrating a configuration including the photoelectric conversion unit and the initial-stage amplifier according to the third embodiment.

FIG. 67 is a diagram (3) illustrating a configuration including a photoelectric conversion unit and an initial-stage amplifier according to the third embodiment. In FIG. 67, first PD, second PD, switches SWs1, SWs2, SWs3, and SWs4, DACs 48a and 48c, and current sources 48b and 48d correspond to photoelectric conversion unit 340 and DC cancellation mechanism 355.

Switches SWs1, SWs2, SWs3, and SWs4 are switches that are turned on when the intermittent light reception starts and turned off when the intermittent light reception ends. When first PD receives light, current flows from Vcc to the circuit side. On the other hand, when second PD receives light, current flows from the circuit to the ground side.

DAC 48a and current source 48b operate in cooperation, and when switch SWs3 is turned on, a current is input from VCC to the circuit side to cancel the current flowing from second PD to the ground. DAC 48a and current source 48b adjust the magnitude of the current input from the VCC side to the circuit side according to a predefined relationship between time and current value.

Further, DAC 48c and current source 48d operate in cooperation, and when switch SWs4 is turned on, first PD releases the current of the circuit to the ground to cancel the current flowing from VCC to the circuit. DAC 48c and current source 48d adjust the magnitude of the current that is released to the ground according to a predefined relationship between time and current value. It is sufficient that either of switch SWs3 or switch SWs4 is turned on based on whether the current of first PD is larger or the current of second PD is larger. This can perform DC cancellation even when the current of either first PD or second PD is large.

As described above, by operating first PD, second PD, switches SWs1, SWs2, SWs3, and SWs4, DACs 48a and 48c, and current sources 48b and 48d, the DC component is canceled from the electric signal input to the initial-stage amplifier 47, and the amplification factor of the initial-stage amplifier 47 can be increased. The description of the initial-stage amplifier 47 is the same as the description made with reference to FIG. 66.

Figure 68:
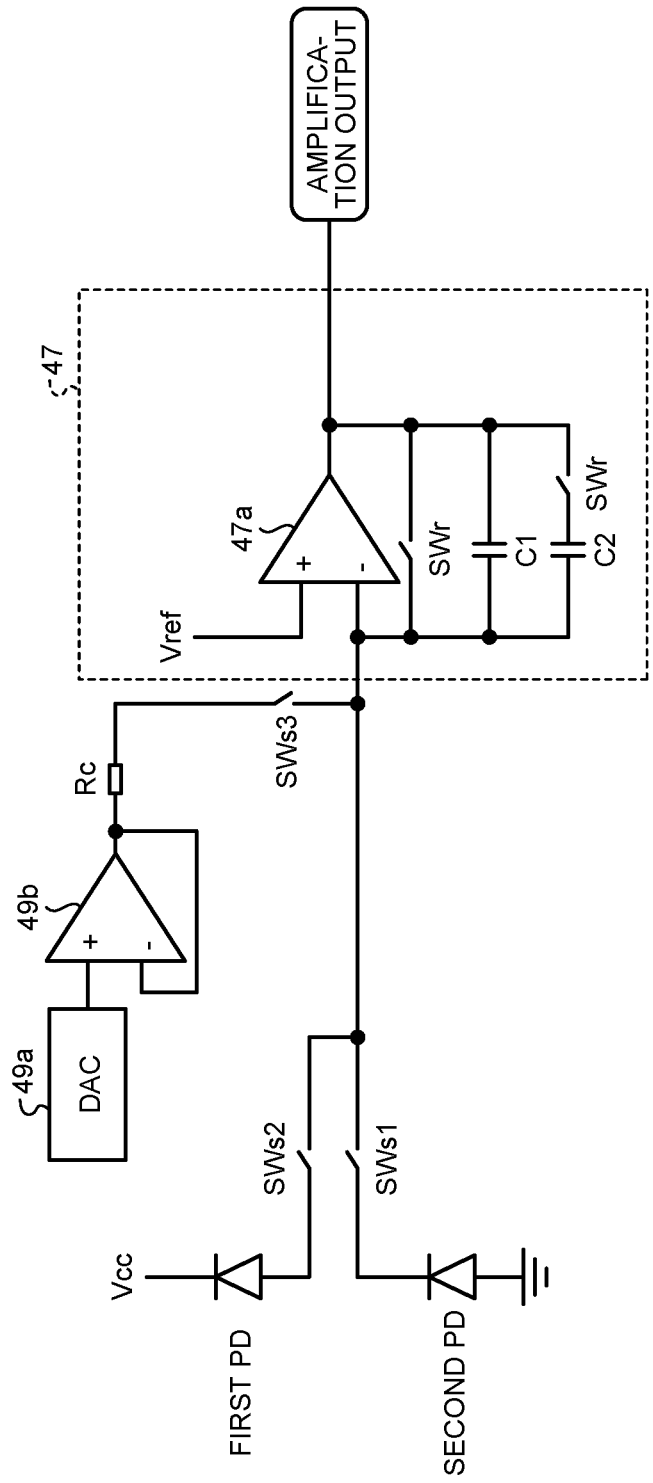
FIG. 68 is a diagram (4) illustrating a configuration including the photoelectric conversion unit and the initial-stage amplifier according to the third embodiment.

FIG. 68 is a diagram (4) illustrating a configuration including a photoelectric conversion unit and an initial-stage amplifier according to the third embodiment. In FIG. 68, first PD, second PD, switches SWs1, SWs2, and SWs3, DAC 49*a*, operational amplifier 49*b*, and Rc correspond to photoelectric conversion unit 340 and DC cancellation mechanism 355.

Switches SWs1, SWs2, and SWs3 are switches that are turned on when the intermittent light reception starts and turned off when the intermittent light reception ends. When first PD receives light, current flows from Vcc to the circuit side. On the other hand, when second PD receives light, current flows from the circuit to the ground side.

DAC 49*a* and operational amplifier 49*b* operate in cooperation, and when switch SWs3 is turned on, the current corresponding to the difference between the potential output from Vref and the potential output from DAC 49*a* flows from operational amplifier 49*b* to Rc and is input to operational amplifier 49*b* to cancel the current of the difference between the current input from the first PD to the circuit and the current flowing from the second PD to the ground.

As described above, by operating first PD, second PD, switches SWs1, SWs2, and SWs3, DAC 49*a*, and operational amplifier 49*b*, the DC component is canceled from the electric signal input to the initial-stage amplifier 47, and the amplification factor of the initial-stage amplifier 47 can be increased. The description of the initial-stage amplifier 47 is the same as the description made with reference to FIG. 66.

<<5.3. Effect of Measurement Device According to Third Embodiment>>

Measurement device 300 according to the third embodiment is provided with DC cancellation mechanism 355. DC cancellation mechanism 355 is a circuit that cancels an intermittent DC component of the electric signal output from a photoelectric conversion unit 240. For example, the photoelectric conversion unit 340 receives (intermittently receives) light (scattered light) reflected when laser is intermittently output, converts the light into an electric signal, and outputs the converted electric signal to the QV amplifier 350. Here, DC cancellation mechanism 355 cancels the DC component of the intermittent electric signal converted in the intermittent light reception. By canceling the DC component, the amplification factor of the QV amplifier 350 can be increased.

6. Conclusion

A measurement device includes a light source that irradiates a subject with light, a drive control unit that intermittently drives the light source, a light receiving element that receives scattered light of the light from the subject and generates an electric signal, and an amplifier that amplifies the electric signal with an integration circuit. This can improve external light resistance and achieve low power consumption.

The light source can emit light with a driving current that maximizes light emission efficiency even when allowable output optical power has an upper limit. This can minimize the power consumption of the laser light source.

The amplifier connects to the light receiving element to acquire the electric signal in a period in which the light receiving element receives the scattered light, and includes a disconnection unit that releases connection with the light receiving element in a period in which the light receiving element does not receive the scattered light. This can discard an electric signal due to external light other than light emission and improve external light resistance.

The measurement device further includes a potential retention circuit that retains a potential of an electric signal output from the amplifier and outputs an electric signal retaining the potential. This can stably amplify a minute signal of $\frac{1}{1000}$ or less of the DC signal and can suppress generation of noise even when intermittent driving is performed.

The drive control unit further intermittently drives the amplifier and the potential retention circuit. The drive control unit further intermittently drives the subsequent-stage amplifier. This can suppress power consumption.

The measurement device further includes an analog filter that removes a low-frequency component of the electric signal output from the potential retention circuit. The measurement device further includes a potential setting mechanism unit that applies a potential in a transition period of the analog filter. The potential setting mechanism unit connects a potential setting resistor to a resistor of the analog filter in parallel to temporarily decrease a time constant and rapidly stabilize a potential of the analog filter. The potential setting mechanism cuts off the analog filter from the amplifier before the amplifier is powered off, and connects the analog filter and the amplifier after a potential of the amplifier stabilizes. As a result, the time until the potential of the analog filter stabilizes is shortened, and the minute signal amplifiable period can be lengthened.

The measurement device further includes a canceling mechanism unit that cancels an intermittent DC component of an electric signal input from the light receiving element to the amplifier. The canceling mechanism unit uses a current source that inputs a current to the amplifier to cancel an intermittent DC component of an electric signal input from the light receiving element to the amplifier. The canceling mechanism unit uses a plurality of light receiving elements to cancel an intermittent DC component of an electric signal input from the plurality of light receiving elements to the amplifier. This suppresses saturation of the amplifier amplified by the integration circuit due to the DC component and can increase the amplification factor of the amplifier amplified by the integration circuit.

A measurement device includes a first analog filter that removes a low-frequency component of a first electric signal, a second analog filter that removes a low-frequency component of a second electric signal, a first potential setting mechanism that applies a potential in a transition period of the first analog filter, a second potential setting mechanism that applies a potential in a transition period of the second analog filter, a differential amplifier circuit that amplifies a difference between the first electric signal output from the first analog filter from which the low frequency component has been removed and the second electric signal output from the second analog filter from which the low frequency component has been removed, and outputs an amplified electric signal. This cancels the noise component and can improve the accuracy in the case of calculating the blood flow signal using the electric signal output from the differential amplifier circuit.

The effects described in the present specification are merely examples and are not restrictive of the disclosure herein, and other effects may be achieved.

The present technology can also have the following configurations.

REFERENCE SIGNS LIST

100, 200, 300 MEASUREMENT DEVICE
110, 210, 310 TIMING CONTROL UNIT 115, 215, 315 INTERMITTENT OPERATION UNIT
120, 220, 320 INTERMITTENT DRIVING LASER DRIVER
130, 230, 330 LASER LIGHT SOURCE
140, 240, 340 PHOTOELECTRIC CONVERSION UNIT
150, 250, 350 QV AMPLIFIER
160, 260, 360 S & H CIRCUIT
170, 270, 370 ANALOG FILTER
180, 280, 380 AC AMPLIFIER
275 RAPID POTENTIAL SETTING MECHANISM
355 DC CANCELLATION MECHANISM

The invention claimed is:

1. A measurement device, comprising:
a light source configured to:
    intermittently emit light with a driving current with which light emission efficiency improves as compared with constant light emission; and
    irradiate a subject with the light;
a drive control unit configured to intermittently drive the light source;
a light receiving element configured to:
    receive scattered light of the light from the subject; and
    generate a first generates an electric signal based on the received scattered light; and
an amplifier configured to amplify the first electric signal with an integration circuit.

2. The measurement device according to claim 1, wherein
the amplifier is further configured to connect to the light receiving element to acquire the first electric signal in a first period in which the light receiving element receives the scattered light, and
the amplifier includes a disconnection unit configured to release the connection with the light receiving element in a second period in which the light receiving element does not receive the scattered light.

3. The measurement device according to claim 1, further comprising a potential retention circuit configured to:
retain a potential of a second electric signal output from the amplifier; and
output a third electric signal having the retained potential.

4. The measurement device according to claim 3, wherein the drive control unit is further configured to intermittently drive the amplifier and the potential retention circuit.

5. The measurement device according to claim 4, further comprising an analog filter configured to:
remove a low-frequency component of the third electric signal output from the potential retention circuit, to generate a fourth electric signal; and
output the fourth electric signal.

6. The measurement device according to claim 5, further comprising a subsequent-stage amplifier configured to amplify the fourth electric signal output from the analog filter.

7. The measurement device according to claim 6, wherein the subsequent-stage amplifier is one of a non-inverting amplifier circuit or an inverting amplifier circuit.

8. The measurement device according to claim 7, wherein the drive control unit is further configured to intermittently drive the subsequent-stage amplifier.

9. The measurement device according to claim 5, further comprising a potential setting mechanism unit configured to apply a potential to the analog filter in a transition period of the analog filter.

10. The measurement device according to claim 9, wherein the potential setting mechanism unit is further configured to connect potential setting resistor to a resistor of the analog filter in parallel, to temporarily decrease a time constant and stabilize the potential of the analog filter.

11. The measurement device according to claim 9, wherein the potential setting mechanism unit is further configured to:
cut off the analog filter from the amplifier before the amplifier is powered off; and
connect the analog filter and the amplifier based on a stabilization of a potential of the amplifier.

12. The measurement device according to claim 1, further comprising a canceling mechanism unit configured to cancel an intermittent DC component of the first electric signal input from the light receiving element to the amplifier.

13. The measurement device according to claim 12, wherein
the canceling mechanism unit is further configured to use a current source, and
the current source inputs a current to the amplifier to cancel the intermittent DC component of the first electric signal input from the light receiving element to the amplifier.

14. The measurement device according to claim 13, wherein
the canceling mechanism unit is further configured to use a plurality of light receiving elements to cancel an intermittent DC component of a second electric signal input from the plurality of light receiving elements to the amplifier, and
the plurality of light receiving elements includes the light receiving element.

15. A measurement method, comprising:
intermittently emitting, by a light source, light with a driving current with which light emission efficiency improves as compared with constant light emission;
irradiating, by the light source, a subject with the light;
intermittently driving, by a drive control unit, the light source that irradiates the subject with the light;
receiving, by a light receiving element, scattered light of the light from the subject;
generating, by the light receiving element, an electric signal based on the received scattered light; and
amplifying the electric signal, generated by the light receiving element, with an integration circuit.

16. A measurement device, comprising:
a first analog filter configured to remove a low-frequency component of a first electric signal;
a second analog filter configured to remove a low-frequency component of a second electric signal;
a first potential setting mechanism configured to apply a first potential to the first analog filter in a transition period of the first analog filter;
a second potential setting mechanism configured to apply a second potential to the second analog filter in a transition period of the second analog filter; and
a differential amplifier circuit configured to:
amplify a difference between the first electric signal output from the first analog filter from which the low-frequency component is removed and the second electric signal output from the second analog filter from which the low-frequency component is removed; and
output amplified electric signal based on the amplified difference.

* * * * *